(12) United States Patent
Klee et al.

(10) Patent No.: US 8,709,811 B2
(45) Date of Patent: Apr. 29, 2014

(54) MATERIALS AND METHODS FOR SYNTHESIS OF A FLAVOR AND AROMA VOLATILE IN PLANTS

(75) Inventors: Harry J. Klee, Gainesville, FL (US); Denise Tieman, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1679 days.

(21) Appl. No.: 10/574,124

(22) PCT Filed: Oct. 1, 2004

(86) PCT No.: PCT/US2004/032599
§ 371 (c)(1),
(2), (4) Date: Apr. 23, 2007

(87) PCT Pub. No.: WO2005/035752
PCT Pub. Date: Apr. 21, 2005

(65) Prior Publication Data
US 2012/0083024 A1 Apr. 5, 2012

Related U.S. Application Data

(60) Provisional application No. 60/508,568, filed on Oct. 3, 2003, provisional application No. 60/558,504, filed on Mar. 31, 2004.

(51) Int. Cl.
*C12N 5/04* (2006.01)
*C12N 1/00* (2006.01)
*C12N 15/00* (2006.01)
*C12N 15/05* (2006.01)
*A01H 5/00* (2006.01)
*C07H 21/04* (2006.01)
*C12P 1/00* (2006.01)

(52) U.S. Cl.
USPC ............. 435/419; 435/41; 435/468; 800/287; 800/298; 800/316; 800/317; 536/23.2; 536/24.1

(58) Field of Classification Search
None
See application file for complete search history.

(56) References Cited

U.S. PATENT DOCUMENTS

| | | |
|---|---|---|
| 5,034,322 A | 7/1991 | Rogers et al. |
| 5,106,739 A | 4/1992 | Comai et al. |
| 5,589,610 A | 12/1996 | De Beuckeleer et al. |
| 5,625,136 A | 4/1997 | Koziel et al. |
| 5,639,948 A | 6/1997 | Michiels et al. |
| 5,652,354 A | 7/1997 | Mariani et al. |
| 5,859,328 A | 1/1999 | Nasrallah et al. |
| 6,011,199 A | 1/2000 | Speirs et al. |
| 6,054,574 A | 4/2000 | Quail et al. |
| 6,118,049 A | 9/2000 | Bestwick et al. |
| 6,127,179 A | 10/2000 | DellaPenna et al. |
| 6,340,748 B1 | 1/2002 | Ro et al. |
| 6,455,760 B1 | 9/2002 | Zhao et al. |
| 6,462,185 B1 | 10/2002 | Takakura et al. |
| 6,528,701 B1 | 3/2003 | Wang et al. |
| 6,696,623 B1 | 2/2004 | Doerner et al. |
| 2003/0084486 A1 | 5/2003 | Bruce et al. |
| 2003/0177536 A1 | 9/2003 | Grundler et al. |
| 2004/0019934 A1 | 1/2004 | Ekramoddoullah et al. |
| 2004/0067506 A1 | 4/2004 | Scheres et al. |
| 2004/0078841 A1 | 4/2004 | Atkinson et al. |
| 2004/0123349 A1 | 6/2004 | Xie et al. |

OTHER PUBLICATIONS

Wang J. et al. In Biosci. Biotecnol. Biochem. 1999 vol. 63, No. 12: pp. 2216-2218.*
Tieman et al. Proc Natl Acad Sci U S A. May 23, 2006; 103(21): pp. 8287-8292.*
Guillet G., et al. Plant Physiology, Mar. 2000; vol. 122, pp. 933-943.*
Maldonado-Mendoza, I. et al. Plant Physiology (1996) vol. 110: pp. 43-49.*
Aharoni, A. et al. "Identification of the SAAT gene involved in strawberry flavor biogenesis by use of DNA microarrays" *Plant Cell*, May 2000, pp. 647-661, vol. 12.
Altschul, S. F. et al. "Gapped BLAST and PSI-BLAST: A new generation of protein database search programs" *Nucleic Acids Research*, 1997, pp. 3389-3402, vol. 25, No. 17.
Beltz, G.A., et al. "Isolation of multigene families and determination of homologies by filter hybridization methods" *Methods of Enzymology* (ed. by Wu, R. et al.), 1983, pp. 266-285, vol. 100, Academic Press, New York.
Blume, B. et al. "Expression of ACC oxidase promoter-GUS fusions in tomato and *Nicotiana plumbaginifolia* regulated by developmental and environmental stimuli" *The Plant Journal*, 1997, pp. 731-746, vol. 12, No. 4.
Buttery, R.G. et al. "Quantitative studies on origins of fresh tomato aroma volatiles" *J. Agric. Food Chem.*, 1988, pp. 1247-1250, vol. 36, No. 6.
Ciardi, J.A. et al. "Response to *Xanthomonas campestris* pv. *vesicatoria* in tomato involves regulation of ethylene receptor gene expression" *Plant Physiol.*, May 2000, pp. 81-92, vol. 123.
Clancy, M. et al. "Splicing of the maize Sh1 first intron is essential for enhancement of gene expression, and a T-Rich motif increases expression without affecting splicing" *Plant Physiol.*, Oct. 2002, pp. 918-929, vol. 130.
De Boer, H.A. et al. "The *tac* promoter: a functional hybrid derived from the *trp* and *lac* promoters" *Proc. Natl. Acad. Sci. U.S.A.*, Jan. 1983, pp. 21-25, vol. 80, No. 1.

(Continued)

*Primary Examiner* — Russell Kallis
*Assistant Examiner* — Matthew Keogh
(74) *Attorney, Agent, or Firm* — Saliwanchik, Lloyd & Eisenschenk

(57) ABSTRACT

The subject invention concerns polynucleotides encoding a plant 2-phenylethanol dehydrogenase enzyme. In one embodiment, the polynucleotide encodes a tomato 2-phenylethanol dehydrogenase. The subject invention also concerns polynucleotides encoding a plant phenylalanine decarboxylase enzyme. In one embodiment, the polynucleotide encodes a tomato phenylalanine decarboxylase. The subject invention also concerns 2-phenylethanol dehydrogenase polypeptides and phenylalanine decarboxylase polypeptides encoded by polynucleotides of the present invention. The subject invention also concerns methods for providing a plant with an increased flavor and aroma volatile. Plants can be transformed with one or more polynucleotide of the present invention. The subject invention also concerns these transformed plant cells, plant tissue, and plants and transgenic progeny thereof.

41 Claims, 25 Drawing Sheets

(56) References Cited

OTHER PUBLICATIONS

Deikman, J. et al. Organization of ripening and ethylene regulatory regions in a fruit-specific promoter from tomato (*Lycopersicon esculentum*), *Plant Physiol.*, 1992, pp. 2013-2017, vol. 100.

Eshed, Y. et al. "A genomic library of *Lycopersicon pennellii* in *L. esculentum*: A tool for fine mapping of genes" *Euphytica*, 1994, pp. 175-179, vol. 79, No. 3.

Fray, R. et al. "Identification and genetic analysis of normal and mutant phytoene synthase genes of tomato by sequencing, complementation and co-suppression" *Plant Molecular Biology*, 1993, pp. 589-602, vol. 22, No. 4.

Giovannoni, J. "Molecular biology of fruit maturation and ripening" *Annual Review of Plant Physiology and Plant Molecular Biology*, 2001, pp. 725-749, vol. 52, No. 1.

Giovannoni, J. et al. "A MADS-Box gene necessary for fruit ripening at the tomato ripening-inhibitor (Rin) locus" *Science*, Apr. 2002, pp. 343-346, vol. 296, No. 5566.

Giovannoni, J.J. et al. "Expression of a chimeric polygalacturonase gene in transgenic rin (Ripening Inhibitor) tomato fruit results in polyuronide degradation but not fruit softening" *Plant Cell*, Jan. 1989, pp. 53-63, vol. 1.

Giovannoni, J. et al. "Genetic mapping of ripening and ethylene-related loci in tomato" *Theoretical and Applied Genetics*, May 1999, pp. 1005-1013, vol. 98, No. 6-7.

Good, X. et al. "Reduced ethylene synthesis by transgenic tomatoes expressing S-adenosylmethionine hydrolase" *Plant Molecular Biology*, 1994, pp. 781-790, vol. 26, No. 3.

Gray, J.E. et al. "The use of transgenic and naturally occurring mutants to understand and manipulate tomato fruit ripening" *Plant, Cell and Environment*, May 1994, pp. 557-571, vol. 17.

Hamilton, A. et al. "Antisense gene that inhibits synthesis of the hormone ethylene in transgenic plants" *Nature*, 1990, pp. 284-287, vol. 346, No. 6281.

Karlin, S. et al. "Methods for assessing the statistical significance of molecular sequence features by using general scoring schemes" *Proc. Natl. Acad. Sci. U.S.A.*, Mar. 1990, pp. 2264-2268, vol. 87.

Karlin, S. et al. "Applications and statistics for multiple high-scoring segments in molecular sequences" *Proc. Natl. Acad. Sci. U.S.A.*, Jun. 1993, pp. 5873-5877, vol. 90.

Klee, H.J. et al. "Control of ethylene synthesis by expression of a bacterial enzyme in transgenic tomato plants" *Plant Cell*, Nov. 1991, pp. 1187-1193, vol. 3.

Lanahan, M. B. et al. "The never ripe mutation blocks ethylene perception in tomato" *Plant Cell*, Apr. 1994, pp. 521-530, vol. 6.

Larroy, C. et al. "Characterization of the *Saccharomyces cerevisiae* YMR318C (ADH6) gene product as a broad specificity NADPH-dependent alcohol dehydrogenase: relevance in aldehyde reduction" *Biochemistry Journal*, Jan. 2002, pp. 163-172, vol. 361.

Lashbrook, C. et al. "Transgenic analysis of tomato endo-β-1,4-glucanase gene function. Role of *cel1* in floral abscission" *Plant Journal*, Feb. 1998, pp. 303-310, vol. 13, No. 3.

Lelievre, J.M et al. "Ethylene and fruit ripening" *Physiologia Plantarum*, 1997, pp. 727-739, vol. 101, No. 4.

Lincoln, J.E. et al. "Regulation of gene expression by ethylene during *Lycopersicon esculentum* (tomato) fruit development" *Proc. Natl. Acad. Sci. U.S.A.*, May 1987, 2793-2797, vol. 84.

Maunders, M.J. et al. "Ethylene stimulates the accumulation of ripening-related mRNAs in tomatoes" *Plant Cell and Environment*, 1987, pp. 177-184, vol. 10.

Moore, S. et al. "Use of genomics tools to isolate key ripening genes and analyse fruit maturation in tomato" *Journal of Experimental Botany*, Oct. 2002, pp. 2023-2030, vol. 53, No. 377.

Nakatsuka, A. et al. "Differential expression and internal feedback regulation of 1-aminocyclopropane-1-carboxylate synthase, 1-aminocyclopropane-1-carboxylate oxidase, and ethylene receptor genes in tomato fruit during development and ripening" *Plant Physiology*, Dec. 1998, pp. 1295-1305, vol. 118.

Oeller, P.W. et al. "Reversible inhibition of tomato fruit senescence by antisense RNA" *Science*, Oct. 1991, pp. 427-439, vol. 254, No. 5030.

Payton, S. et al. "Ethylene receptor expression is regulated during fruit ripening, flower senescence and abscission" *Plant Molecular Biology*, Sep. 1996, pp. 1227-1231, vol. 31, No. 6.

Richins, R.D. et al. "Sequence of figwort mosaic virus DNA (*Caulimovirus* group)" *Nucl. Acids Res.*, Oct. 1987, pp. 8451-8466, vol. 15, No. 20.

Ronen, G. et al. "Regulation of carotenoid biosynthesis during tomato fruit development: Expression of the gene for lycopene epsilon-cyclase is down-regulated during ripening and is elevated in the mutant *Delta*" *Plant Journal*, Feb. 1999, pp. 341-351, vol. 17.

Rontein, D. et al. "Plants synthesize ethanolamine by direct decarboxylation of serine using a pyridoxal phosphate enzyme" *J. Biol. Chem.*, Sep. 2001, pp. 35523-35529, vol. 276, No. 38.

Saliba-Colombani, V. et al. "Genetic analysis of organoleptic quality in fresh market tomato. 1. Mapping QTLs for physical and chemical traits" *Theoretical and Applied Genetics*, Feb. 2001, pp. 259-272, vol. 102, No. 2-3.

Schmelz, E. A. et al. "The influence of intact-plant and excised-leaf bioassay designs on volicitin- and jasmonic acid-induced sesquiterpene volatile release in *Zea mays*" *Planta*, Dec. 2001, pp. 171-179, vol. 214.

Schmelz, E. A. et al. "Quantitative relationships between induced jasmonic acid levels and volatile emission in *Zea mays* during *Spodoptera exigua* herbivory" *Planta*, Feb. 2003, pp. 665-673, vol. 216.

Schwartz, S.H. et al. "Characterization of a novel carotenoid cleavage dioxygenase from plants" *J. Biol. Chem.*, Jul. 2001, pp. 25208-25211, vol. 276, No. 27.

Stark, D. et al. "Inhibition aspects of the bioconversion of L-phenylalanine to 2-phenylethanol by *Saccharomyces cerevisiae*" *Enzyme and Microbial Technology*, Feb. 2003, pp. 212-223, vol. 32, No. 2.

Tadmor, Y. et al. "Identification of malodorous, a wild species allele affecting tomato aroma that was selected against during domestication" *Journal of Agricultural and Food Chemistry*, Mar. 2002, pp. 2005-2009, vol. 50, No. 7.

Tan, B.C. et al. "Genetic control of abscisic acid biosynthesis in maize" *Proc. Natl. Acad. Sci. U.S.A.*, Oct. 1997, pp. 12235-12240, vol. 94.

Tanksley, S.D. et al. "High density molecular linkage maps of the tomato and potato genomes" *Genetics*, 1992, pp. 1141-1160, vol. 132.

Tieman, D. "Identification of genes involved in tomato volatile synthesis" From the American Society of Biologists, No. 258, XP002339006, http://abstracts.aspb.org/pb2004/public/M03/9103.html. (Abstract only).

Vrebalov, J. et al. "A MADS-Box gene necessary for fruit ripening at the tomato ripening-inhibitor (Rin) locus." *Science*, Apr. 2002, pp. 343-346, vol. 296, No. 5566.

Wilkinson, J.Q. et al. "An ethylene-inducible component of signal transduction encoded by never-ripe" *Science*, Dec. 1995, pp. 1807-1809, vol. 270, No. 5243.

Xu, D. et al. "Systemic induction of a potato pin2 promoter by wounding, methyl jasmonate, and abscisic acid in transgenic rice plants" *Plant Molecular Biology*, Jul. 1993, pp. 573-588, vol. 22, No. 4.

Yang, T.T. et al. "Optimized codon usage and chromophore mutations provide enhanced sensitivity with the green fluorescent protein" *Nucleic Acids Research*, Nov. 1996, pp. 4592-4593, vol. 24, No. 22.

Yen, H.C. et al. "The tomato high-pigment (hp) locus maps to chromosome 2 and influences plastome copy number and fruit quality" *Theoretical and Applied Genetics*, Nov. 1997, pp. 1069-1079, vol. 95, No. 7.

Yen, H.C. et al. "The tomato never-ripe locus regulates ethylene-inducible gene expression and is linked to a homolog of the *arabidopsis* ETR1 gene" *Plant Physiology*, Apr. 1995, pp. 1343-1353, vol. 107, No. 4.

\* cited by examiner

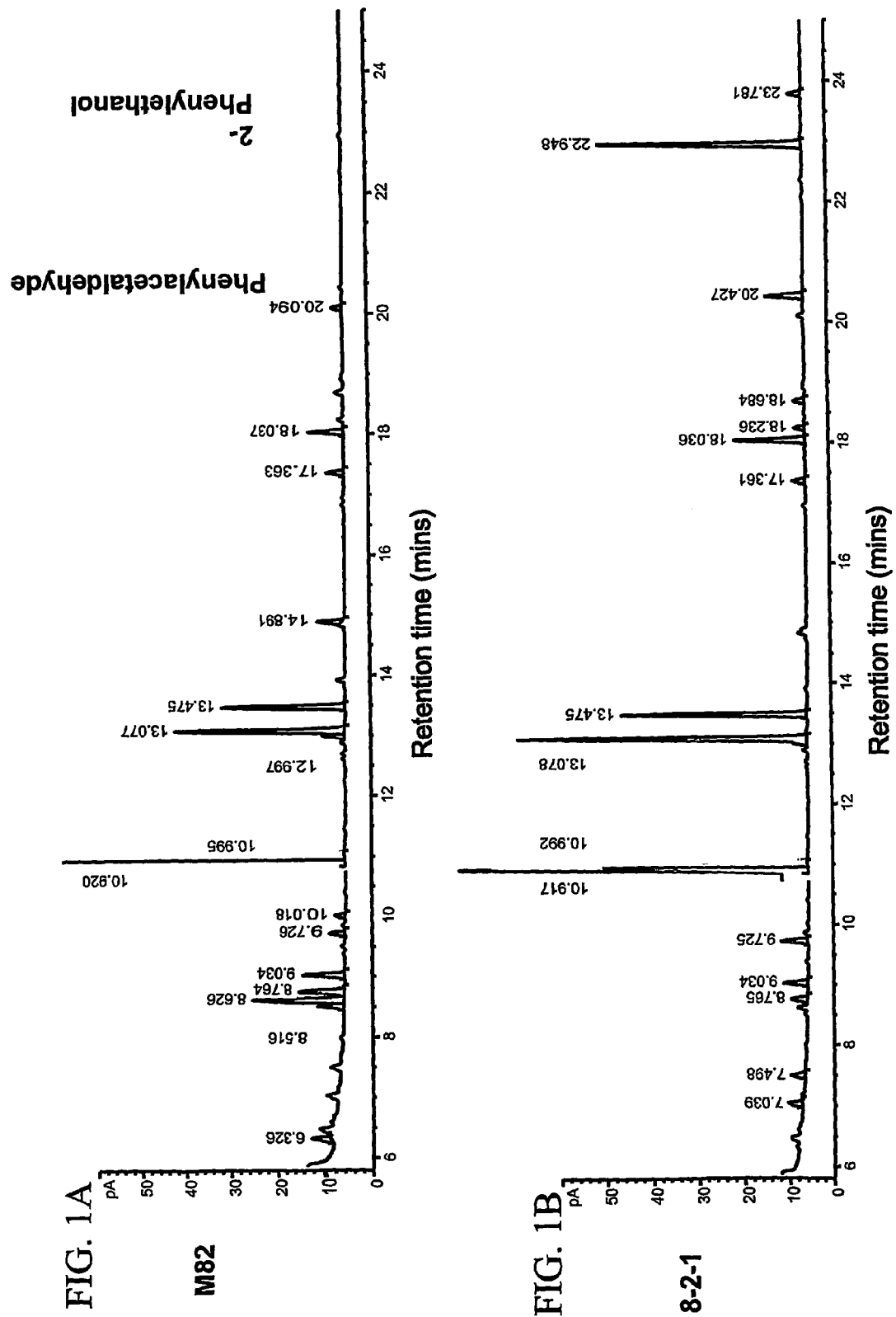
FIG. 1A  M82
FIG. 1B  8-2-1

```
   1  GCCCTTCTAA TACGACTCAC TATAGGGCAA GCAGTGGTAA CAACGCAGAG
  51  TACGCGGGGG AAGGATAATC TCTCAAATTA CTTTCTTTTT TTTTCCTATC
 101  AATTCTTTAT ACCAAATAA  TATTATTGTT TTTTTCTCCT CTGTTTCTGC
 151  TTCGTATTTT TGCTGAGAGA AATGAGTGTG ACAGCGAAAA CAGTGTGTGT
 201  AACAGGAGCT TCAGGTTACA TAGCTTCATG GCTTCTGTTC GCTAGTCAAA TTCTTGCTAC
 251  ATAGTGGTTA CAATGTGAAG GCTTCTGTTC GTGATCCAAA TGATCCCAAG
 301  AAAACGCAGC ACTTGCTTTC TCTTGGTGGG GCCAAGGAGA GGCTTCACTT
 351  GTTCAAAGCA AACCTATTAG AAGAAGGTTC ATTTGATGCT GTAGTTGATG
 401  GATGTGAAGG TGTATTCCAT ACAGCGTCTC CTTTTACTA  CTCTGTTACA
 451  GACCCACAGG CTGAATTACT TGATCCTGCT GTTAAGGGAA CACTCAATCT
 501  TCTCGGGTCA TGTGCCAAAG CACCATCAGT AAAACGAGTT GTTTTAACGT
 551  CTTCCATAGC TGCAGTTGCT TACAGTGGTC AGCCTCGGAC ACCTGAGGTT
 601  GTGGTTGATG AGAGCTGGTG GACCAGTCCA GACTACTGCA AAGAAAAACA
 651  GCTCTGGTAT GTCCCTCTCAA AGACATTGGC TGAGGATGCT GCGTGGAAGT
 701  TTGTGAAGGA GAAAGGCATT GATATGGTTG TAGTAAACCC TGCTATGGTT
 751  ATTGGTCCTC TGTTACAGCC TACACTTAAT ACCAGTTCTG CTGCAGTCTT
 801  GAGCTTGGTA AATGGTGCTG AGACATACCC AAATTCCTCT TTTGGGTGGG
 851  TTAACGTGAA AGATGTTGCA AATGCACATA TTCTTGCATT TGAGAACCCT
 901  TCAGCTAATG GGAGATACTT AATGGTTGAG AGGGTTGCAC ACTATTCTGA
 951  TATATTGAAG ATATTGCGTG ACCTTTATCC TACTATGCAA CTTCCAGAAA
1001  AGTGTGCTGA TGACAACCCA TTGATGCAA  ATTATCAAGT ATCAAAGGAG
1051  AAGGCAAAAA GCTTGGGTAT TGAGTTTACT ACCCTTGAAG AAAGCATCAA
1101  AGAAACTGTT GAAAGTTTGA AGGAAAAGAA GTTTTTTGGA GGTTCATCTT
1151  CTATGTAAAA GGCTTCTCAA AGCTTTTATG GTTTTGTTGA ACAATACTAC
1201  CCACCCCACC CTACCCCTACA CACTTTTTTT TTTTACTTCT TTTAGCTAAT
1251  TATAGAATCA AGAAGTCGAA TGGTATATCC GTTAATAAAT TTCGATCAGA
1301  TGAGGTTGAA ATTTGTTCTA TATCTAGAGA TTTTTACAGA CTGGTTTGAT
1351  AGAAAAAAA  AAAAAAA    (SEQ ID NO: 1)
```

FIG. 3A

```
  1  MSVTAKTVCV TGASGYIASW LVKFLLHSGY NVKASVRDPN DPKKTQHLLS
 51  LGGAKERLHL FKANLLEEGS FDAVVDGCEG VFHTASPFYY SVTDPQAELL
101  DPAVKGTLNL LGSCAKAPSV KRVVLTSSIA AVAYSGQPRT PEVVVDESWW
151  TSPDYCKEKQ LWYVLSKTLA EDAAWKFVKE KGIDMVVVNP AMVIGPLLQP
201  TLNTSSAAVL SLVNGAETYP NSSFGWVNVK DVANAHILAF ENPSANGRYL
251  MVERVAHYSD ILKILRDLYP TMQLPEKCAD DNPLMQNYQV SKEKAKSLGI
301  EFTTLEESIK ETVESLKEKK FFGGSSSM (SEQ ID NO: 2)
```

FIG. 3B

```
   1 ATGGGAAGTT TATCATTTGA GAAGGATTTT GAGCCATCAG CAATTACTCC
  51 AAGAGGATTA GCACCACCTG GATTAATTGT AAATGGTGAT TTTGGTGAAA
 101 TGATGAGACT TAAGGTGTCA TCAACACCAA CAACACCAAG AAAAAACTTG
 151 AATCTTTCAG TGACGGAGCC AGGAAAAAAT GATGGACCTA GTTTGGATTG
 201 TACATTGATG AATTATATTG ATACACTCAC CCAACGTATC AACTATCATA
 251 TCGGTTATCC AGTTAACATA TGTTATGAGC ACTATGCTAA TTTAGCCCCA
 301 CTTTTACAAT TTCATTAAAA TAATTGTGGT GATCCATTTC TTCAAAATAC
 351 TGTGGATTTT CATTCAAAGG ATTTTGAAGT GGCTGTTTTA AATTGGTTTG
 401 CTGATTTATG GGAAAATTGA AGAGATCAAT ATGGGGCTA TGTAACAAAT
 451 GGTGGTACTG AAGGAAATTT ACATGGCATT TTGGTTGGGA GAGAATTGTT
 501 TCCAGATGGA ATTTTATATG CATCAAAAGA CTCTCATTAC TCAGTGGCTA
 551 AGGCAGCAAT GATGTATAGA ATGGATTTTG AAAATATTAA CGCATCAATA
 601 AATGGAGAAA TCGATTATTC TGATTTGAAA GTTAAATTAC TTCAAAACAA
 651 GGGAAAACCA GCGATAATTA ATGTTACAAT TGGCACTACT TTTAAAGGAG
 701 CTGTTGATGA TCTTGATGTT ATTCTTCAAA TACTTGAAGA GTGTGGTTAC
 751 ACACGAGATC AATTTATAT TCATTGTGAT GCAGCACTAA ATGGACTTAT
 801 TATTCCTTTT ATTAAAAATA TGATTACTTT CAAGAAGCCA ATTGGAAGTG
 851 TGACAATTTC TGGTCACAAG TTTTTGGGAT GTCCAATGCC TTGTGGAGTT
 901 CAAATAACAA GGAAAAGTTA CATTAATAAC CTTTCGAGAA GAGTCGAATA
 951 TATTGCTTCT GTGGATGCTA CAATTTCTGG AAGTCGAAAT GGTTTGACTC
1001 CGATCTTCTT ATGGTACAGT ATAAGTGCTA AAGTACTTGA AAGACCGTCT
1051 AAAGACGTTA AGAGATGTTT TGACAATGCT AAGTACTTGA AAGACCGTCT
1101 TCAGCAAGCA GGAATCAGCG TCATGCTGAA TGAGCTTAGC ATCATAGTTG
1151 TCCTCGAGAG GCCTCGTGAC CATGAATTCG TTCGTCGTTg GCAATTATCT
1201 TGTGTGAGAG ATATGGCACA TGTTATTGTT ATGCCAGGCA TAACTAGAGA
1251 AACTCTTGAT GGTTTTATTA ATGATTGCT TCAACAAAGG AAAAAATGGT
1301 ATCAAGATGG AAGAATTAGC CCTCCTTGTG TTGCAAATGA TATTGGTGCT
1351 CAAAATTGTG CTTGCTCTTA TCATAAAATT GATTACATTA TTGCTTAG (SEQ ID NO: 4)
```

FIG. 8A

```
  1  MGSLSFEKDF EPSAITPRGL APPGLIVNGD FGEMMRLKVS STPTTPRKNL
 51  NLSVTEPGKN DGPSLDCTLM NYIDTLTQRI NYHIGYPVNI CYEHYANLAP
101  LLQFHLNNCG DPFLQNTVDF HSKDFEVAVL NWFADLWEIE RDQYWGYVTN
151  GGTEGNLHGI LVGRELFPDG ILYASKDSHY SVAKAAMMYR MDFENINASI
201  NGEIDYSDLK VKLLQNKGKP AINVTIGTT  FKGAVDDLDV ILQILEECGY
251  TRDQFYIHCD AALNGLIIPF IKNMITFKKP IGSVTISGHK FLGCPMPCGV
301  QITRKSYINN LSRRVEYIAS VDATISGSRN GLTPIFLWYS ISAKGQIGFQ
351  KDVKRCFDNA KYLKDRLQQA GISVMLNELS IIVVLERPRD HEFVRRWQLS
401  CVRDMAHVIV MPGITRETLD GFINDLLQQR KKWYQDGRIS PPCVANDIGA
451  QNCACSYHKI DYIIA (SEQ ID NO: 5)
```

FIG. 8B

```
   1 ATGGGTAGTC TCTCACTTGA AATGGATTTT GAGCCATCAC CCATGACACC
  51 CAGAAGTTTA GCAGCGATGA CACCTAGAAG TTTAGCGCGA CGACGATTGT
 101 TTCCGAACGT GGACAACAAG AAACAGAAAA TGGCACAACC AGGTGCAGGA
 151 CCAAGGAAGA ACTTGGAACT TGAGGTCATG GAGCCTGCAT TGAAGAATGA
 201 TGGTCCTTCT TTGGACACTA TCTTGGTTAA TTATTGGAC ACACTTACAC
 251 AACGAGTCAA TTATCATTTA GGTTATCCAG TCAACATATG TTATGATCAC
 301 TATGCAACGC TAGCACCACT TTTGCAGTTT CACCTAAACA ATGTGGTGA
 351 TCCTTTCCTA CAAATACTG TCGATTTCCA TTCTAAAGAC TTTGAAGTGG
 401 CTGTTTTGAA TTGGTTTGCA AAACTTTGGG AAATTGAAAA GGATCAATAT
 451 TGGGGATATG TTACCAATGG TGGCACCGAA GGCAATCTCC ATGTATTTT
 501 GTTAGGGAGA GAGCTACTTC CTGAAGGAAT ATTATATGCA TCAAAAGACT
 551 CTCATTACTC AGTATTCAAA GCTGCAAGAA TGTATAGAAT GGATTCAGAA
 601 ACAATCAACA CATCAGTAAA TGGAGAGATG GATTATTCAG ATTTAAGAGC
 651 AAAGTTACTT CAAAATAAGG ATAAACCAGC TATTATAAAT GTCACAATTG
 701 GAACTACATT CAAAGGAGCA ATCGATGACC TGGATGTTAT TCTTGAAATA
 751 CTCAAAGAAT GTGGCTATTC ACAAGATCGA TTTTACATTC ACTGTGATGC
 801 AGCACTATGT GGTCTTATGA CCCCTTTAT AACAATATG ATTAGTTCA
 851 AGAAGCCAAT TGGAAGTGTC ACAATTCTG GACACAAGTT TTTGGATGT
 901 CCAATGCCTT GTGGTGTCCA AATAACAAGA AAAAGCTACA TCAATAATCT
 951 CTCAACAAAT GTGGAATACA TTGCTTCTGT GGATGCCACT ATTTCTGGTA
1001 GCCGTAACGG TTTAACTCCA ATTTTCTTAT GGTATAGCTT GAGCGCAAAA
1051 GGTCAAGTTG GACTTCAAAA GGATGTTAAA AGATGTCTCG ACAATGCCAA
1101 ATATTTGAAA GATCGTCTTC AACAAGCAGG GATAAGTGTC ATGCTGAATG
1151 AGCTAAGCAT CATAGTTGTA CTTGAAAGGC CTCGTGACCA TGAATTGTG
1201 CGTCGTTGGC AACTCTCATG CGTCAAGGAT ATGGCACATG TTATTGTGAT
1251 GCCAGGAATC ACACGAGAAA TGCTTGACAA CTTCATGAGT GAATTAGTGC
1301 AACAAAGAAA AGTATGGTAT CAAAATGGAA AGACTGATCC TCCTTGTGTT
1351 GGAGAGGATA TTGGTGCTCA AAATTGTGCA TGCTCTTATC ATAAGATTGA
1401 CTACATCTGT CCTTAG (SEQ ID NO: 6)
```

FIG. 9A

```
  1 MGSLSLEMDF EPSPMTPRSL AAMTPRSLAR RRLFPNVDNK KQKMAQPGAG
 51 PRKNLELEVM EPALKNDGPS LDTILVNYLD TLTQRVNYHL GYPVNICYDH
101 YATLAPLLQF HLNNCGDPFL QNTVDFHSKD FEVAVLNWFA KLWEIEKDQY
151 WGYVTNGGTE GNLHGILLGR ELLPEGILYA SKDSHYSVFK AARMYRMDSE
201 TINTSVNGEM DYSDLRAKLL QNKDKPAIIN VTIGTTFKGA IDDLDVILEI
251 LKECGYSQDR FYIHCDAALC GLMTPFINNM ISFKKPIGSV TISGHKFLGC
301 PMPCGVQITR KSYINNLSTN VEYIASVDAT ISGSRNGLTP IFLWYSLSAK
351 GQVGLQKDVK RCLDNAKYLK DRLQQAGISV MLNELSIIVV LERPRDHEFV
401 RRWQLSCVKD MAHVIVMPGI TREMLDNFMS ELVQQRKVWY QNGKTDPPCV
451 GEDIGAQNCA CSYHKIDYIC P (SEQ ID NO: 7)
```

FIG. 9B

```
   1  ATGGGTAGTC TCTCACTTGA AATGGATTTT GAGCCATCAC CTATGACACC
  51  CAGAAGTTTA GCAGCGATGA CACCTAGAAG TTTAGCGCGG CGAAGATTGT
 101  TTCCCAATGT GGACAACAAA AAACAAAAGG TGCAACAATC AGGTGCAGGG
 151  CCAAGGAAGA ACTTACAACT TGAAGTCATG GAACCTGCAT TGAACAATGC
 201  TGGTCCCTCT TTGGACACTA TATTGGTCAA TTATTAGAC  ACACTTACAC
 251  AACGAGTCAA TTATCATTTA GGTTATCCAG TCAACATTTG TTATGATCAC
 301  TATGCAACTT TAGCACCACT TTTACAGTTT CACCTAAACA ATTGTGGTGA
 351  TCCTTTCCTA CAAAACACTG TCGATTTCCA TTCTAAAGAC TTTGAAGTGG
 401  CTGTTTTGAA TTGGTTTGCA AAACTATGGG AAATTGAAAA GGATCAATAC
 451  TGGGGATATG TTACCAATGG TGGCACCGAA GGCAATCTCC ATGGTATTTT
 501  GTTAGGGAGA GAGCTACTTC CTGATGGAAT ATTATATGCG TCAAAAGACT
 551  CTCACTATTC GGTCTTCAAA GCTGCAAGAA TGTATAGAAT GGATTCAGAA
 601  ACAATCAACA CATCAGTAAA CGGAGAGATG GATTATTCAG ATTAAGAGC
 651  AAAGTTACTT CAAAATAAGG ATAAACCAGC TATTATAAAT GTCACAATTG
 701  GAACTACGTT CAAAGGAGCA ATCGATGACC TGGATGTTAT TCTTGAAACA
 751  CTCAAAGAAT GTGGCTATTC GCAAGATAGG TTTTACATCC ACTGTGATGC
 801  TGCACTATGT GGTCTTATGA CCCCTTTTAT AAACAATATG ATTAGTTTCA
 851  AGAAGCCAAT TGGAAGTGTC ACAATTCTG  GACACAAGTT TTTGGATGT
 901  CCAATGCCTT GTGGTGTGCA AATTACAAGA AAGAGTTACA TCAATAATCT
 951  CTCAACAAAT GTGGAATACA TTGCTTCTGT CGATGCCACT ATTTCTGGCA
1001  GCCGTAACGG TTTAACTCCA ATTTTCTTGT GGTATAGCTT GAGCGCAAAA
1051  GGTCAAGTTG GACTTCAAAA GGATGTTAAA AGATGTCTCG ACAATGCCAA
1101  ATATTTGAAA GATCGTCTTC AAAAAGCAGG AATAAGTGTC ATGTTAAATG
1151  AGCTTAGCAT CATAGTTGTA CTTGAAAGGC CTCGTGACCA TGAATTGTC
1201  CGTCGTTGGC AACTCTCATG CGTCAAGGAT ATGGCACATG TTATTGTAAT
1251  GCCAGGCATC ACACGAGAAA TGCTTGACAA TTTCACGAGT GAATTAGTGC
1301  AACAAAGAAA AGTATGGTAT CAAAATGGAC AGACCAATCC TCCTTGTGTT
1351  GGAGAGGATA TTGGTGCTCA AAATTGTGCA TGCTCTCTTATC ATAAGATTGA
1401  CTACATCTGT CCTTAG (SEQ ID NO: 8)
```

FIG. 11A

```
  1  MGSLSLEMDF EPSPMTPRSL AAMTPRSLAR RRLFPNVDNK KQKVQQSGAG
 51  PRKNLQLEVM EPALNNAGPS LDTILVNYLD TLTQRVNYHL GYPVNICYDH
101  YATLAPLLQF HLNNCGDPFL QNTVDFHSKD FEVAVLNWFA KLWEIEKDQY
151  WGYVTNGGTE GNLHGILLGR ELLPDGILYA SKDSHYSVFK AARMYRMDSE
201  TINTSVNGEM DYSDLRAKLL QNKDKPAIIN VTIGTTFKGA IDDLDVILET
251  LKECGYSQDR FYIHCDAALC GLMTPFINNM ISFKKPIGSV TISGHKFLGC
301  PMPCGVQITR KSYINNLSTN VEYIASVDAT ISGSRNGLTP IFLWYSLSAK
351  GQVGLQKDVK RCLDNAKYLK DRLQKAGISV MLNELSIIVV LERPRDHEFV
401  RRWQLSCVKD MAHVIVMPGI TREMLDNFTS ELVQQRKVWY QNGQTNPPCV
451  GEDIGAQNCA CSYHKIDYIC P (SEQ ID NO: 9)
```

FIG. 11B

```
1                                                                                    50
Lp-cLEC73K23  MGSLSLEMDF  EPSPMTPRSL  AAMTPRSLAR  RRLFPNVDNK  KQKVQQSGAG
Le-cLEC73K23  MGSLSLEMDF  EPSPMTPRSL  AAMTPRSLAR  RRLFPNVDNK  KQKMAQPGAG
Le-cLEC75E21  MGSLSFEKDF  EPSAITPRGL  A...PPGLIV  NGDFGEM..M  RLKVSSTPTT 51                                                                                   100
Lp-cLEC73K23  PRKNLQLEVM  EPALNNAGPS  LDTILVNYLD  TLTQRVNYHL  GYPVNICYDH
Le-cLEC73K23  PRKNLELEVM  EPALKNDGPS  LDTILVNYLD  TLTQRVNYHL  GYPVNICYDH
Le-cLEC75E21  PRKNLNLSVT  EPG.KNDGPS  LDCTLMNYID  TLTQRINYHI  GYPVNICYEH 101                                                                                  150
Lp-cLEC73K23  YATLAPLIQF  HLNNCGDPFL  QNTVDFHSKD  FEVAVLNWFA  KLWEIEKDQY
Le-cLEC73K23  YATLAPLIQF  HLNNCGDPFL  QNTVDFHSKD  FEVAVLNWFA  KLWEIEKDQY
Le-cLEC75E21  YANLAPLIQF  HLNNCGDPFL  QNTVDFHSKD  FEVAVLNWFA  DLWEIERDQY 151                                                                                  200
Lp-cLEC73K23  WGYVTNGGTE  GNLHGILLGR  ELLPDGILYA  SKDSHYSVFK  AARMYRMDSE
Le-cLEC73K23  WGYVTNGGTE  GNLHGILLGR  ELLPEGILYA  SKDSHYSVFK  AARMYRMDSE
Le-cLEC75E21  WGYVTNGGTE  GNLHGILVGR  ELFPDGILYA  SKDSHYSVAK  AAMYRMDFE 201                                                                                  250
Lp-cLEC73K23  TINTSVNGEM  DYSDLRAKLL  QNKDKPAIIN  VTIGTTFKGA  IDDLDVILET
Le-cLEC73K23  TINTSVNGEM  DYSDLRAKLL  QNKDKPAIIN  VTIGTTFKGA  IDDLDVILEI
Le-cLEC75E21  NINASINGEI  DYSDLKVKLL  QNKGKPAIIN  VTIGTTFKGA  VDDLDVILQI
```

FIG. 12A

```
         251
Lp-cLEC73K23  LKECGYSQDR  FYIHCDAALC  GLMTPFINNM  ISFKKPIGSV  TISGHKFLGC
Le-cLEC73K23  LKECGYSQDR  FYIHCDAALC  GLMTPFINNM  ISFKKPIGSV  TISGHKFLGC
Le-cLEC75E21  LEECGYTRDQ  FYIHCDAALN  GLIIPFIKNM  ITFKKPIGSV  TISGHKFLGC 301                                                      350
Lp-cLEC73K23  PMPCGVQITR  KSYINNLSTN  VEYIASVDAT  ISGSRNGLTP  IFLWYSLSAK
Le-cLEC73K23  PMPCGVQITR  KSYINNLSTN  VEYIASVDAT  ISGSRNGLTP  IFLWYSLSAK
Le-cLEC75E21  PMPCGVQITR  KSYINNLSRR  VEYIASVDAT  ISGSRNGLTP  IFLWYSISAK 351                                                      400
Lp-cLEC73K23  GQVGLQKDVK  RCLDNAKYLK  DRLQKAGISV  MLNELSIIVV  LERPRDHEFV
Le-cLEC73K23  GQVGLQKDVK  RCLDNAKYLK  DRLQQAGISV  MLNELSIIVV  LERPRDHEFV
Le-cLEC75E21  GQIGFQKDVK  RCFDNAKYLK  DRLQQAGISV  MLNELSIIVV  LERPRDHEFV 401                                                      450
Lp-cLEC73K23  RRWQLSCVKD  MAHVIVMPGI  TREMLDNFTS  ELVQQRKVWY  QNGQTNPPCV
Le-cLEC73K23  RRWQLSCVKD  MAHVIVMPGI  TREMLDNFMS  ELVQQRKVWY  QNGKTDPPCV
Le-cLEC75E21  RRWQLSCVRD  MAHVIVMPGI  TRETLDGFIN  DLLQQRKKWY  QDGRISPPCV 451              472
Lp-cLEC73K23  GEDIGAQNCA  CSYHKIDYIC  P    (SEQ ID NO: 9)
Le-cLEC73K23  GEDIGAQNCA  CSYHKIDYIC  P    (SEQ ID NO: 7)
Le-cLEC75E21  ANDIGAQNCA  CSYHKIDYII  A    (SEQ ID NO: 5)
```

FIG. 12B

```
  1  ATGAGTAGTG TGGCAGCGAC AAAAACAGTA TGTGTAACAG GAGCATCAGG
 51  ATACATAGCA TCATGGCTTG TCAATTTCTT GCTTCAACGT GGTTACACTG
101  TTAAAGCCTC CGTTCGTGAC CCCAATGATC CCAAGAAAAC ACAGCATTTG
151  ATCTCGTTAG GTGGGGCCAA GGAGAGGCTT CACTTGTTCA AAGCAAACCT
201  TTTAGAAGAG GGTTCCTTTG ATGCTGTGGT TGATGGATGT GAAGGTGTAT
251  TCCATACAGC ATCACCTTTT TACTACTCTG TTACAGACCC ACAGGCTGAA
301  TTACTTGATC CAGCTGTTAA GGGGACACTC AATCTTCTCG GTTCATGTGC
351  CAAAGCACCA TCAGTAAAAC GTGTGGTTTT AACATCTTCC ATAGCTGCAG
401  TTGCTTATAG TGGTGAGCCT CGGACACCTG AGGTTGTGGT TGATGAGAGT
451  TGGTGGACTA GTCCAGACTA CTGCAGAGAA AAGCAGCTCT GGTATGTTCT
501  CTCAAAGACA TTAGCTGAGG ATGCTGCCTG GAAGTTTGTG AAGGAGAAAG
551  GCATTGATAT GGTTGCAATA AATCCTGCTA TGGTTATTGG TCCTTTGTTA
601  CAGCCTACCC TTAATACCAG TTCTGCTGCA GTCTTGAACT TGGTAAATGG
651  TGCCGAGACA TACCCAAATG CTACCTTTGG GTGGGTTAAT GTCAAAGATG
701  TTGCAAATGC ACATATTCTT GCATTTGAGA ACCCTTCAGC TAATGGGAGA
751  TATTTGATGG TTGAGAGAGT TGCACACTAT TCTGATATAC TGAAGATATT
801  ACGTGAACTT TATCCTACAA TGCCGACTTCC AGAAAAGTGT GCTGATGACA
851  ATCCATTGAT GCAAAACTAT CAAGTATCAA AAGAAAGGGC AAAAAGCTTG
901  GGCGTTGAAT TTACTCCCCT TGAAGAAAAGC ATCAAAGAAA CTGTTGAAAG
951  CTTGAAGGAA AAGAAGTTTT TTGGAGGCTC ATCTGCTATG TGA (SEQ ID NO: 10)
```

FIG. 14A

```
  1  MSSVAATKTV CVTGASGYIA SWLVNFLLQR GYTVKASVRD PNDPKKTQHL
 51  ISLGGAKERL HLFKANLLEE GSFDAVVDGC EGVFHTASPF YYSVTDPQAE
101  LLDPAVKGTL NLLGSCAKAP SVKRVVLTSS IAAVAYSGEP RTPEVVDES
151  WWTSPDYCRE KQLWYVLSKT LAEDAAWKFV KEKGIDMVAI NPAMVIGPLL
201  QPTLNTSSAA VLNLVNGAET YPNATFGWVN VKDVANAHIL AFENPSANGR
251  YLMVERVAHY SDILKILREL YPTMRLPEKC ADDNPLMQNY QVSKERAKSL
301  GVEFTPLEES IKETVESLKE KKFFGGSSAM (SEQ ID NO: 11)
```

FIG. 14B

MATERIALS AND METHODS FOR SYNTHESIS OF A FLAVOR AND AROMA VOLATILE IN PLANTS

CROSS-REFERENCE TO RELATED APPLICATIONS

This application is the U.S. national stage application of International patent application No. PCT/US2004/032599, filed Oct. 1, 2004, which claims the benefit of U.S. Provisional Application Ser. No. 60/508,568, filed Oct. 3, 2003 and U.S. Provisional Application Ser. No. 60/558,504, filed Mar. 31, 2004.

This invention was made with government support under National Science Foundation grant number 7223426-12. The government has certain rights in the invention.

BACKGROUND OF THE INVENTION

Fruits are major components of the human diet contributing a large portion of vitamins, minerals, antioxidants, and fiber. While flavor and nutrition composition have clear and profound potential for positive human benefit, they have proven to be difficult traits to modify via either traditional breeding or transgenic approaches due to their generally complex biosynthetic and regulatory pathways. In fact, the biochemical descriptors that comprise flavor are poorly defined. What is typically perceived as flavor in many fruits is the product of a complex interaction among sugars, acids and multiple volatile secondary metabolites (Buttery et al., 1988; Baldwin et al., 2000). Synthesis and accumulation of these compounds is the result of coordinated activity of many genes that may also impact additional aspects of plant growth and development. Effective manipulation of these traits for human benefit will therefore require greater knowledge of the pathways involved and the regulatory systems which control them. Prior to the advent of genomics, researchers could focus on the activity of only one to several genes important in a process of interest and could view their respective effects in relative isolation. From a practical perspective, flavor and nutrition are intimately related and equally important as flavor directly impacts the choice of foods for consumption which, in turn, has positive nutritional consequences on the human diet.

Fruit-bearing crop plants are taxonomically diverse (e.g., pepper, tomato, melons, apples, bananas, grapes). However, they do share common features; most, though not all, fruits are enlarged ovaries. While our knowledge of how domesticated plants came to bear fruit or the mechanisms by which they ripen is still rudimentary, more is known about these processes in tomato (*Lycopersicon esculentum*) than in any other species (see Giovannoni (2001) for review). Furthermore, a diverse set of Near Isogenic Lines (NILs), single gene ripening mutants, and transgenic lines represent portals through which genetic regulation of fruit development and ripening can be studied (Gray et al., 1994; Giovannoni et al., 1999). The diversity of genetically well characterized tomato germplasm described below (Table 1) is unparalleled in other fruiting species. Nevertheless, it is important to realize that while fruit ripening is a complex sum of coordinately regulated biochemical events that vary from species to species, key regulatory components are likely to be maintained (Hobson and Grierson, 1993). For example, one group has recently identified two genes that are essential for fruit ripening, RIN and NOR (Giovannoni, 2001; Vrebalov et al., 2002). Fruit-specific, ripening-induced homologues of these genes have been identified from strawberry and banana (Vrebalov et al., 2002). Strawberry undergoes a very different ripening program as compared to tomato in that strawberry is non-climacteric (i.e. no increase in respiration or ethylene biosynthesis during ripening) and accumulates high levels of anthocyanins rather than carotenoids during fruit maturation. Further, it is anatomically a receptacle, whereas most fruits are ovaries. Banana is interesting in that while its fruit are also expanded carpels, it is a monocot. Apparently similar ripening control shared among monocots and dicots indicates that basic ripening regulation is likely conserved through evolution. In summary, these results suggest that while specific nutritional and flavor components may vary among fruit species they are likely due to regulated metabolic flux through similar pathways with similar genetic control systems. Thus, regulatory and biosynthetic genes identified in tomato will allow for modification of the same or related compounds in a wide range of agriculturally important fruit species.

Tomato has long served as a model system for plant genetics, development, physiology and fruit ripening resulting in the accumulation of substantial information regarding the biology of this economically important plant. Many experimental tools and features of tomato make it ideal for study of fruit ripening; these include extensive germplasm collections, numerous natural, induced, and transgenic mutants, routine transformation technology, a dense and expanding RFLP map, numerous cDNA and genomic libraries, a small genome, relatively short life-cycle and ease of growth and maintenance. In addition, numerous genomic tools that have and continue to be developed include: a) over 140,000 EST sequences (~30,000 non-redundant) from 23 different tomato tissues/treatments (with one-third of the ESTs derived from fruit), b) EST expression arrays being developed and utilized (see bti.cornell.edu/CGEP/CGEP.html) and c) recent initiation of activities toward development of a tomato physical map anchored to the genetic map to facilitate gene isolation and eventual genome sequencing (Tanksley et al., NSF tomato genome project, 1992). The intense research effort in tomato fruit biology has resulted in many important discoveries that have had a broad impact on the field of plant biology, including control of gene expression by antisense technology, characterization of numerous genes influencing fruit development and ripening, characterization of genes for ethylene synthesis and perception, and the recent connection of ripening regulation and ethylene response to the molecular regulation of floral development (Vrebalov et al., 2002).

Fruit maturation and ripening is the summation of biochemical and physiological changes occurring at the terminal stage of development rendering the organ edible and valuable as an agricultural commodity. These changes frequently include modification of cell wall ultrastructure and texture, conversion of starch to sugars, alterations in pigment and nutrient biosynthesis/accumulation, and heightened levels of flavor and aromatic volatiles (Rhodes, 1980; Hobson and Grierson, 1993). While some ripening effects, such as carotenoid and vitamin C synthesis and accumulation, have direct impact on the nutritive value of mature fruit, others impacting flavor and texture (e.g., volatiles, sugars and acids) can have an indirect impact on human nutrition via their contributions to total consumption levels. In short, "if it tastes better" consumption will increase. This is especially critical as poor food choices exert a disproportional impact on children and members of society on lower rungs of the socio-economic ladder.

Although most fruits display modifications in color, texture, flavor and nutrient composition during maturation, two major classifications of ripening, climacteric and non-climacteric, have been utilized to distinguish fruit on the basis of respiration and ethylene synthesis rates. Climacteric fruits such as tomato, avocado, banana, peaches and apples, are distinguished from non-climacteric fruits such as strawberry, grape and citrus, by their increased respiration and ethylene synthesis rates during ripening (Lelievre et al., 1998). In tomato, ethylene has been shown to be necessary for the coordination and completion of ripening (Yang, 1985; Tucker and Brady, 1987; Klee et al., 1991; Picton et al., 1993; Lanahan et al., 1994). The critical role of ethylene in coordinating climacteric ripening at the molecular level was first observed via analysis of ethylene inducible ripening-related gene expression in tomato (Lincoln et al., 1987; Maunders et al., 1987). Numerous fruit development-related genes have since been isolated via differential expression patterns and biochemical function (reviewed in Gray et al., 1994). The in vivo functions of many fruit development- and ripening-related genes have been tested via antisense repression and/or mutant complementation in tomato. As examples, polygalacturonase was shown to be necessary for ripening-related pectin depolymerization and pathogen susceptibility, yet to have little effect on fruit softening (Smith et al., 1988, Giovannoni et al., 1989, Kramer et al., 1990). Inhibition of phytoene synthase resulted in reduced carotenoid biosynthesis and reduction in fruit and flower pigmentation (Fray and Grierson, 1993). Reduced ethylene evolution resulted in ripening inhibition of ACC synthase (ACS) and ACC oxidase (ACO) antisense lines (Oeller et al., 1991; Hamilton et al., 1990) while introduction of a dominant mutant allele of the NR ethylene receptor resulted in plants inhibited in virtually every measurable ethylene response including fruit ripening (Wilkinson et al., 1995; Yen et al., 1995).

Expression analysis of multiple tomato ripening-related genes indicates that a subset exhibit developmentally-controlled ethylene inducibility, i.e., they are ethylene inducible only in ripening fruits. Examples include members of the ACO and ACS gene families (Theologis et al., 1993; Blume and Grierson, 1997; Nakatsuka et al., 1998), the NR ethylene receptor (Wilkinson et al., 1995; Payton et al., 1996; Lashbrook et al., 1998) and E8 (Deikman et al., 1992). Additional evidence for non-ethylene mediated ripening control comes from analysis of gene expression in ripening impaired mutants such as rin (ripening-inhibitor) and nor (non-ripening) that fail to ripen in response to exogenous ethylene yet display signs of ethylene sensitivity and signaling including induction of some ethylene-regulated genes (Yen et al., 1995). These results suggest that regulatory constraints are placed on climacteric fruit maturation in addition to general ethylene biosynthesis and signaling. Such mechanisms could include fruit-specific regulation of certain subsets of ethylene regulated genes or factors that operate separate from and in addition to ethylene as seems to be the case for both the RIN (Vrebalov et al., 2002) and NOR transcription factors. This is particularly interesting as a greater understanding of the relationship between ethylene, developmental, and environmental signals will likely reveal the impact of various signaling systems on pathways impacting flavor and human nutrition. Indeed numerous environmental factors such as light and temperature can dramatically influence the degree and rate of fruit ripening with significant impacts on the accumulation of carotenoids and flavor compounds (Hobson and Grierson, 1993; Yen et al., 1997).

Numerous plant metabolites can be listed when the net of "nutritive compounds" is cast. These include various antioxidants, vitamins, minerals, fiber, lipids, and amino acids, to name just a few. In addition, as noted above, one can rationally argue that modification of flavor and additional quality attributes may lead to improved health via increased fruit or vegetable consumption.

Tomato fruits are among the highest source of lycopene, β-carotene, and vitamin C (ascorbate) in the diets of humans in the US, South America, and Europe, with steadily increasing prominence in Asia and the Middle East. In addition to direct nutritive value, carotenoids in particular are metabolized to compounds that impact flavor and aroma of fruit and thus have a significant impact on resulting fresh and processed products. Genes encoding the synthetic steps from phytoene through β-carotene (Bartley et al., 1994; Ronen et al., 1999) are potential regulatory points for modification of carotenoid levels. Indeed, available data indicate that accumulation of lycopene is due to coordinated up-regulation of the genes preceding its synthesis and down-regulation of genes that further metabolize it during ripening (Ronen et al., 1999). Numerous mutant, transgenic, RI and breeding lines that display a wide range of levels of lycopene and β-carotene are available (Table 1). While specific mutants represent some of the catalytic steps (e.g., r=phytoene synthase and cr and B=lycopene cyclase; Hamilton et al., 1990; Ronen et al., 1999) others such as hp-1 and hp-2 represent regulators of environmental response. Antisense phytoene synthase tomato lines are greatly reduced in all of the carotenoid-derived volatiles (Baldwin et al., 2000). Furthermore, transgenic and mutant lines altered in ethylene synthesis or perception display variation in carotenoid levels (Table 1).

TABLE 1

Tomato germplasm altered in carotenoids, flavonoids, vitamin C.

| Genotype | Carotenoids | Vit. C | Volatiles | Function |
|---|---|---|---|---|
| rin; ripening-inhibitor* | very low | low | NA | MADS-box protein |
| nor; non-ripening* | low | low | NA | transcription factor |
| Nr: Never-ripe* | low | NA | NA | ethylene receptor |
| hp-2; high-pigment-2 | high | high | NA | DET1 (light signaling) |
| cr; crimson | low B, high L | high | NA | lycopene cyclase |
| B; Beta | high B, low L | NA | NA | lycopene cyclase |
| r; Phytoene Synthase | low | NA | low | phytoene synthase |
| hp-1; high-pigment-1** | high | high | NA | Not cloned (light signaling) |
| Nr-2: Never-ripe-2 | low | NA | NA | Not cloned |
| Gr: Green-ripe | low | NA | NA | Not cloned |
| t; tangerine | low | NA | NA | Not cloned |
| at; apricot | low | NA | NA | Not cloned |
| Cnr; Clear non-ripening | low | NA | NA | Not cloned |
| L. esculentum × L. pennellii | low-high | low-high | low-high | |

TABLE 1-continued

Tomato germplasm altered in carotenoids, flavonoids, vitamin C.

| | Carotenoids | Vit. C | Volatiles | Function |
|---|---|---|---|---|
| Recombinant Inbreds | | | | |
| ACO; ACC oxidase* | low | NA | NA | ethylene Biosynthesis |
| ACS; ACC synthase* | low | NA | NA | ethylene Biosynthesis |
| ACD; ACC deaminase* | low | NA | NA | ethylene Biosynthesis |
| TCTR1; tomato CTR1* | low-high | NA | NA | ethylene signaling MAPKKK |

The dashed line separates mutants for which the corresponding gene has been cloned (1st tier) from those which have not (2nd tier). The last tier indicates transgenic lines altered in ethylene synthesis or response and with corresponding changes in carotenoid accumulation. Genotypes indicated with an (*) represent those for which multiple independent transgenic lines are available demonstrating a range of carotenoid accumulation levels.
**Three different mutant alleles of hp-1 each having varying degrees of effect on carotenoid and flavonoid accumulation were provided by M. Koornneef.
B = β-carotene.
L = lycopene.
While quantitative data for vitamin C and volatiles are unknown for many of these lines (NA), their respective phenotypes suggest they are likely to be altered in one or both.

In the case of flavor volatiles, the pathways for synthesis are in many cases not well established. For example, synthesis of apocarotenoids such as β-ionone and β-damascenone is not at all understood. Only recently has an *Arabidopsis* enzyme, CCD1 (Carotenoid Cleavage Dioxygenase), that synthesizes apocarotenoids such as β-ionone in vitro been identified (Schwartz et al., 2001). This gene is part of a multigene family, some of which are responsible for synthesis of other apocarotenoids such as ABA (Tan et al., 1997). CCD 1 cleaves multiple carotenoid substrates at the 9-10 and 9'-10' bonds, potentially releasing volatiles such as β-ionone, although this has not been established in vivo. Similarly, several different volatiles are derived from lipid breakdown (Table 2). The likely first step in their syntheses is the action of a lipoxygenase (LOX) (Riley and Thompson, 1997; Baldwin et al., 2000). Currently there are 14 different EST contigs in the tomato database putatively identified as LOX. Any LOX exhibiting correlation with the lipid-derived volatiles would be a candidate sequence for analyses. It is exactly this sort of correlative biochemical and expression approach that resulted in identification of a key enzyme in strawberry volatile synthesis (Aharoni et al., 2000).

TABLE 2

The 16 most significant flavor volatiles of tomato

| Volatile | Conc. (ppb) | Log odor units | Precursor | Odor Characteristics |
|---|---|---|---|---|
| cis-3-Hexenal | 12,000 | 3.7 | lipid | Tomato/green |
| β-ionone | 4 | 2.8 | carotenoid | fruity/floral |
| Hexanal | 3,100 | 2.8 | lipid | green/grassy |
| β-Damascenone | 1 | 2.7 | carotenoid | Fruity |
| 1-Penten-3-one | 520 | 2.7 | lipid | fruity floral/green |
| 2 + 3-Methylbutanal | 27 | 2.1 | ILE/LEU | Musty |
| trans-2-Hexenal | 270 | 1.2 | lipid | Green |
| 2-Isobutylthiazole | 36 | 1.0 | LEU | Tomato vine |
| 1-nitro-2-Phenylethane | 17 | 0.9 | PHE | musty, earthy |
| trans-2-Heptenal | 60 | 0.7 | lipid | Green |
| Phenylacetaldehyde | 15 | 0.6 | PHE | floral/alcohol |
| 6-Methyl-5-hepten-2-one | 130 | 0.4 | carotenoid | fruity, floral |
| cis-3-Hexenol | 150 | 0.3 | lipid | Green |
| 2-Phenylethanol | 1,900 | 0.3 | PHE | Nutty |
| 3-Methylbutanol | 380 | 0.2 | LEU | earthy, musty |
| Methyl salicylate | 48 | 0.08 | PHE | wintergreen |

Volatiles are ranked by importance based on Odor Units (concentration X humans' ability to detect). Concentrations are average values from typical commercial tomatoes. Odor characteristics were determined by a trained expert panel.

BRIEF SUMMARY OF THE INVENTION

The subject invention concerns polynucleotides encoding a plant 2-phenylethanol dehydrogenase enzyme. In one embodiment, a polynucleotide encodes a tomato 2-phenylethanol dehydrogenase. In another embodiment, a polynucleotide encodes a petunia 2-phenylethanol dehydrogenase. The subject invention also concerns 2-phenylethanol dehydrogenase polypeptides encoded by polynucleotides of the present invention.

The subject invention concerns polynucleotides encoding a plant phenylalanine decarboxylase enzyme. In one embodiment, a polynucleotide encodes a tomato phenylalanine decarboxylase. The subject invention also concerns phenylalanine decarboxylase polypeptides encoded by polynucleotides of the present invention.

The subject invention also concerns methods for providing a plant with increased flavor and aroma volatiles. Plants can be transformed with one or more polynucleotides of the present invention. The subject invention also concerns these transformed plant cells, plant tissues, and plants and transgenic progeny thereof.

BRIEF DESCRIPTION OF THE FIGURES

FIGS. 1A and 1B show the results of GC profiles of volatiles collected from M82 or introgression line 8-2-1 ripe fruit. Introgression line 8-2-1 fruit have higher levels of phenylacetaldehyde and 2-phenylethanol than control M82 fruit.

FIGS. 3A and 3B show a full-length cDNA (SEQ ID NO: 1) and amino acid sequence (SEQ ID NO: 2) of a 2-phenylethanol dehydrogenase of the present invention.

FIGS. 8A and 8B show a full-length coding sequence (SEQ ID NO: 4) and amino acid sequence (SEQ ID NO: 5) of tomato phenylalanine decarboxylase cLEC75E21 of the present invention.

FIGS. 9A and 9B show a full-length coding sequence (SEQ ID NO: 6) and amino acid sequence (SEQ ID NO: 7) of tomato phenylalanine decarboxylase cLEC73K23 of the present invention.

FIGS. 11A and 11B show a full-length coding sequence (SEQ ID NO: 8) and amino acid sequence (SEQ ID NO: 9) of an L. pennellii phenylalanine decarboxylase similar to cLEC73K23 of the present invention.

FIGS. 12A and 12B show an amino acid sequence alignment of L. esculentum cLEC73K23 (SEQ ID NO: 7), L. esculentum cLEC75E21 (SEQ ID NO: 5) and the L. pennellii cLEC73K23 homolog (SEQ ID NO: 9).

FIGS. 14A-14B show the nucleotide (SEQ ID NO: 10) and amino acid sequence (SEQ ID NO: 11) of a petunia homolog of the tomato phenylethanol dehydrogenase. The E. coli expressed protein exhibits phenylethanol dehydrogenase activity in vitro.

BRIEF DESCRIPTION OF THE SEQUENCES

Figure 2:
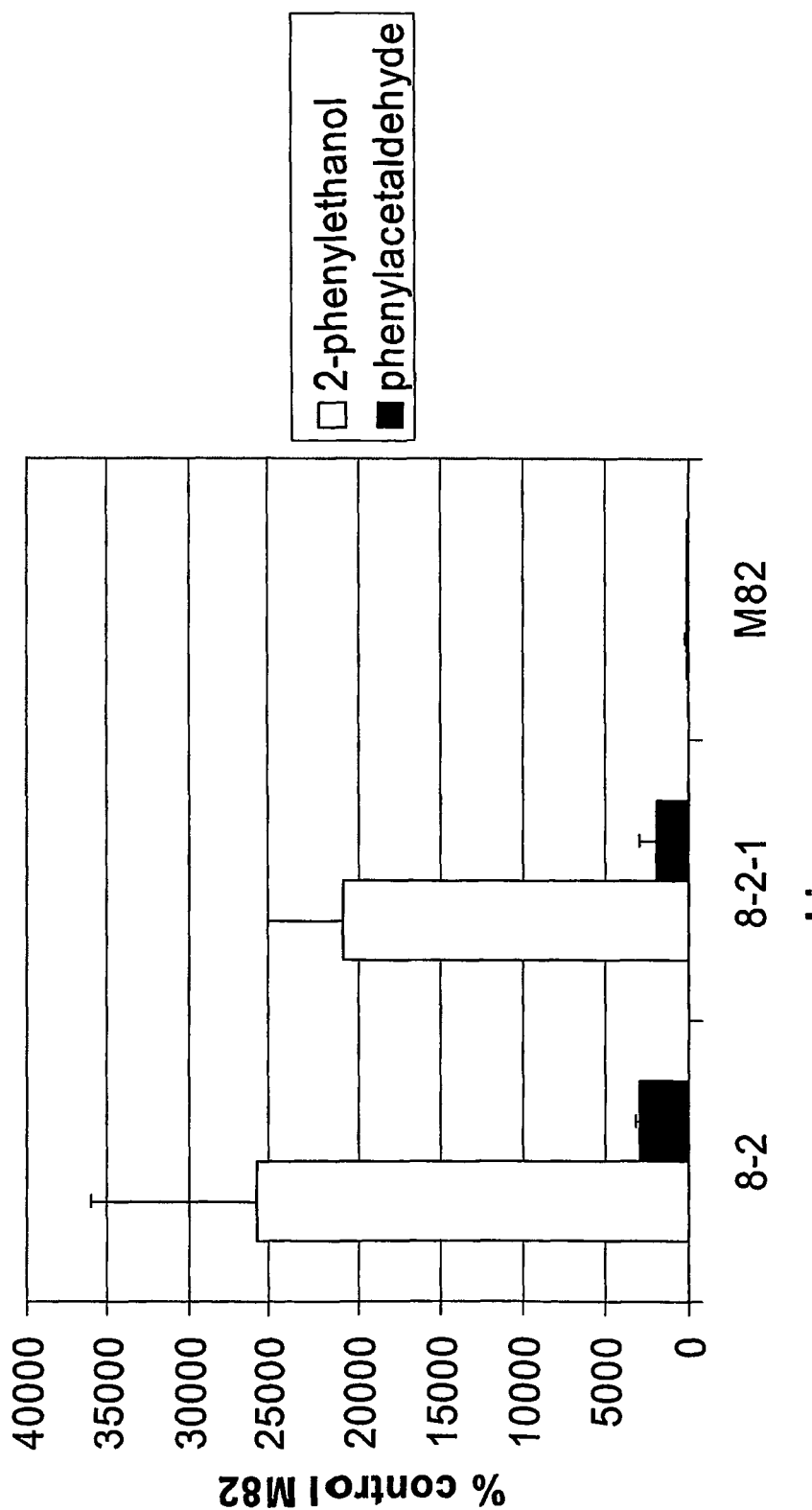
FIG. 2 is a graph of phenylacetaldehyde and 2-phenylethanol levels in control M82 and *L. pennellii* introgression line 8-2-1 fruit. Data are presented as % of control M82 fruit.

SEQ ID NO: 1 shows a nucleotide sequence encoding a 2-phenylethanol dehydrogenase according to the present invention.

SEQ ID NO: 2 shows an amino acid sequence of a 2-phenylethanol dehydrogenase encoded by SEQ ID NO: 1 of the present invention.

SEQ ID NO: 3 shows an oligonucleotide PCR primer that can be used according to the present invention.

SEQ ID NO: 4 shows a nucleotide sequence encoding a phenylalanine decarboxylase according to the present invention.

SEQ ID NO: 5 shows an amino acid sequence of a phenylalanine decarboxylase encoded by SEQ ID NO: 4 of the present invention.

SEQ ID NO: 6 shows a nucleotide sequence encoding a phenylalanine decarboxylase according to the present invention.

SEQ ID NO: 7 shows an amino acid sequence of a phenylalanine decarboxylase encoded by SEQ ID NO: 6 of the present invention.

SEQ ID NO: 8 shows a nucleotide sequence encoding a phenylalanine decarboxylase according to the present invention.

SEQ ID NO: 9 shows an amino acid sequence of a phenylalanine decarboxylase encoded by SEQ ID NO: 8 of the present invention.

SEQ ID NO: 10 shows a nucleotide sequence encoding a petunia homolog of a tomato 2-phenylethanol dehydrogenase according to the present invention.

SEQ ID NO: 11 shows an amino acid sequence of a 2-phenylethanol dehydrogenase encoded by SEQ ID NO: 10 of the present invention.

SEQ ID NO: 12 shows a nucleotide sequence encoding a phenylalanine decarboxylase according to the present invention.

SEQ ID NO: 13 shows an amino acid sequence of a phenylalanine decarboxylase encoded by SEQ ID NO: 12 of the present invention.

DETAILED DISCLOSURE OF THE INVENTION

The subject invention concerns polynucleotides encoding a plant 2-phenylethanol dehydrogenase enzyme. In one embodiment, the polynucleotide encodes a 2-phenylethanol dehydrogenase of tomato; however, polynucleotides encoding homologous 2-phenylethanol dehydrogenase polypeptides of other plant species are also contemplated within the scope of the present invention. In another embodiment, the polynucleotide encodes a 2-phenylethanol dehydrogenase of petunia. In an exemplified embodiment, the polynucleotide encodes a tomato 2-phenylethanol dehydrogenase polypeptide having an amino acid sequence shown in SEQ ID NO: 2, or an enzymatically active fragment or variant thereof. In another exemplified embodiment, the polynucleotide encodes a petunia 2-phenylethanol dehydrogenase polypeptide having an amino acid sequence shown in SEQ ID NO: 11, or an enzymatically active fragment or variant thereof. In a specific embodiment, the polynucleotide encoding the amino acid sequence shown in SEQ ID NO: 2 comprises the nucleotide sequence shown in SEQ ID NO: 1, or a sequence encoding an enzymatically active fragment or variant of SEQ ID NO: 2. In a further specific embodiment, the polynucleotide encoding the amino acid sequence shown in SEQ ID NO: 11 comprises the nucleotide sequence shown in SEQ ID NO: 10, or a sequence encoding an enzymatically active fragment or variant of SEQ ID NO: 11. Thus, the subject invention concerns polynucleotide sequences comprising the nucleotide sequence shown in SEQ ID NO: 1 or SEQ ID NO: 11, or a variant, including a degenerate variant, of SEQ ID NO: 1 or SEQ ID NO: 11. In one embodiment, the polynucleotide encoding the amino acid sequence shown in SEQ ID NO: 2 comprises nucleotides 172 to 1155 of the nucleotide sequence shown in SEQ ID NO: 1. In one embodiment, the polynucleotide encoding the amino acid sequence shown in SEQ ID NO: 11 comprises nucleotides 1 to 990 of the nucleotide sequence shown in SEQ ID NO: 10.

The subject invention concerns polynucleotides encoding a plant phenylalanine decarboxylase enzyme. In one embodiment, the polynucleotide encodes a phenylalanine decarboxylase of tomato; however, polynucleotides encoding homologous phenylalanine decarboxylase polypeptides of other plant species are also contemplated within the scope of the present invention. In an exemplified embodiment, the polynucleotide encodes a tomato phenylalanine decarboxylase polypeptide having an amino acid sequence shown in SEQ ID NO: 5, 7, 9, or 13, or an enzymatically active fragment or variant thereof. In a specific embodiment, the polynucleotide encoding the amino acid sequence shown in SEQ ID NO: 5, 7, 9, or 13 comprises the nucleotide sequence shown in SEQ ID NO: 4, 6, 8, or 12, respectively, or a sequence encoding an enzymatically active fragment or variant of SEQ ID NO: 5, 7, 9, or 13. Thus, the subject invention concerns polynucleotide sequences comprising the nucleotide sequence shown in SEQ ID NO: 4, SEQ ID NO: 6, SEQ ID NO: 8, or SEQ ID NO: 12, or a variant, including a degenerate variant, of SEQ ID NO: 4, SEQ ID NO: 6, SEQ ID NO: 8, or SEQ ID NO: 12. In one embodiment, the polynucleotide encoding the amino acid sequence shown in SEQ ID NO: 5 comprises nucleotides 1 to 1395 of the nucleotide sequence shown in SEQ ID NO: 4. In another embodiment, the polynucleotide encoding the amino acid sequence shown in SEQ ID NO: 7, 9, or 13 comprises nucleotides 1 to 1413 of the nucleotide sequence shown in SEQ ID NO: 6, 8, or 12, respectively.

The subject invention also concerns polynucleotide expression constructs comprising a polynucleotide sequence of the present invention encoding a plant 2-phenylethanol dehydrogenase. In one embodiment, an expression construct of the invention comprises a polynucleotide sequence encoding a tomato 2-phenylethanol dehydrogenase comprising an amino acid sequence shown in SEQ ID NO: 2, or an enzymatically active fragment or variant thereof. In another exemplified embodiment, an expression construct of the invention comprises a polynucleotide sequence encoding a petunia 2-phenylethanol dehydrogenase polypeptide having an amino acid sequence shown in SEQ ID NO: 11, or an enzymatically active fragment or variant thereof. In a specific embodiment, the polynucleotide sequence comprises a polynucleotide sequence shown in SEQ ID NO: 1, or a sequence encoding an enzymatically active fragment or variant of SEQ ID NO: 2. In a further specific embodiment, the polynucleotide encoding the amino acid sequence shown in SEQ ID NO: 11 comprises the nucleotide sequence shown in SEQ ID NO: 10, or a sequence encoding an enzymatically active fragment or variant of SEQ ID NO: 11. In one embodiment, the polynucleotide encoding the amino acid sequence shown in SEQ ID NO: 2 comprises nucleotides 172 to 1155 of the nucleotide sequence shown in SEQ ID NO: 1. In one embodiment, the polynucleotide encoding the amino acid sequence shown in SEQ ID NO: 11 comprises nucleotides 1 to 990 of the nucleotide sequence shown in SEQ ID NO: 10.

The subject invention also concerns polynucleotide expression constructs comprising a polynucleotide sequence of the present invention encoding a plant phenylalanine decarboxylase. In one embodiment, an expression construct of the invention comprises a polynucleotide sequence encoding a tomato phenylalanine decarboxylase comprising an amino acid sequence shown in SEQ ID NO: 5, 7, 9, or 13, or an enzymatically active fragment or variant thereof. In a specific embodiment, the polynucleotide sequence comprises a polynucleotide sequence shown in SEQ ID NO: 4, 6, 8, or 12, or a sequence encoding an enzymatically active fragment or variant of SEQ ID NO: 5, 7, 9, or 13. In one embodiment, the polynucleotide encoding the amino acid sequence shown in SEQ ID NO: 5 comprises nucleotides 1 to 1395 of the nucleotide sequence shown in SEQ ID NO: 4. In another embodiment, the polynucleotide encoding the amino acid sequence shown in SEQ ID NO: 7, 9, or 13 comprises nucleotides 1 to 1413 of the nucleotide sequence shown in SEQ ID NO: 6, 8, or 12, respectively.

Expression constructs of the invention generally include regulatory elements that are functional in the intended host cell in which the expression construct is to be expressed. Thus, a person of ordinary skill in the art can select regulatory elements for use in bacterial host cells, yeast host cells, plant host cells, insect host cells, mammalian host cells, and human host cells. Regulatory elements include promoters, transcription termination sequences, translation termination sequences, enhancers, and polyadenylation elements. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

An expression construct of the invention can comprise a promoter sequence operably linked to a polynucleotide sequence encoding a 2-phenylethanol dehydrogenase or phenylalanine decarboxylase of the invention. In one embodiment, the promoter is one that provides for overexpression of a polynucleotide of the present invention. Promoters useful for overexpression of an operably linked nucleic acid sequence are known in the art. Promoters can be incorporated into a polynucleotide sequence or an expression construct using standard techniques known in the art. Multiple copies of promoters or multiple promoters can be used in an expression construct of the invention. In a preferred embodiment, a promoter can be positioned about the same distance from the transcription start site in the expression construct as it is from the transcription start site in its natural genetic environment. Some variation in this distance is permitted without substantial decrease in promoter activity. A transcription start site is typically included in the expression construct.

If the expression construct is to be provided in or introduced into a plant cell, then plant viral promoters, such as, for example, a cauliflower mosaic virus (CaMV) 35S (including the enhanced CaMV 35S promoter (see, for example U.S. Pat. No. 5,106,739)) or a CaMV 19S promoter can be used. In an exemplified embodiment, the promoter is a figwort mosaic virus 35S promoter. Other promoters that can be used for expression constructs in plants include, for example, prolifera promoter, Ap3 promoter, heat shock promoters, T-DNA 1'- or 2'-promoter of A. tumefaciens, polygalacturonase promoter, chalcone synthase A (CHS-A) promoter from petunia, tobacco PR-1a promoter, ubiquitin promoter (U.S. Pat. Nos. 6,528,701 and 6,054,574), actin promoter, alcA gene promoter, pin2 promoter (Xu et al., 1993), maize WipI promoter, maize trpA gene promoter (U.S. Pat. No. 5,625,136), maize CDPK gene promoter, and RUBISCO SSU promoter (U.S. Pat. No. 5,034,322) can also be used. Tissue-specific promoters, for example fruit-specific promoters, such as the E8 promoter of tomato (accession number: AF515784; Good et al. (1994)), a hybrid E4/E8 promoter (U.S. Pat. No. 6,118,049), the LeExp-1 promoter (U.S. Pat. No. 6,340,748), and the polygalacturonase-β subunit promoter of tomato (U.S. Pat. No. 6,127,179) can be used. Flower organ-specific promoters can be used with an expression construct of the present invention for expressing a polynucleotide of the invention in the flower organ of a plant. Examples of flower organ-specific promoters include any of the promoter sequences described in U.S. Pat. Nos. 6,462,185; 5,859,328; 5,652,354; 5,639, 948; and 5,589,610. Seed-specific promoters such as the promoter from a (1-phaseolin gene (e.g., of kidney bean) or a glycinin gene (e.g., of soybean), and others, can also be used. Root-specific promoters, such as any of the promoter sequences described in U.S. Pat. No. 6,455,760 or U.S. Pat. No. 6,696,623, or in published U.S. patent application Nos. 20040078841; 20040067506; 20040019934; 20030177536; 20030084486; or 20040123349, can be used with an expression construct of the invention. Constitutive promoters (such as an CaMV, ubiquitin, actin, or NOS promoter), developmentally-regulated promoters, and inducible promoters (such as those promoters than can be induced by heat, light, hormones, or chemicals) are also contemplated for use with polynucleotide expression constructs of the invention.

For expression in animal cells, an expression construct of the invention can comprise suitable promoters that can drive transcription of the polynucleotide sequence. If the cells are mammalian cells, then promoters such as, for example, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, TRP-1 promoter, murine mammary tumor virus long terminal repeat promoter, STAT promoter, or an immunoglobulin promoter can be used in the expression construct. The baculovirus polyhedrin promoter can be used with an expression construct of the invention for expression in insect cells.

For expression in prokaryotic systems, an expression construct of the invention can comprise promoters such as, for example, alkaline phosphatase promoter, tryptophan (trp) promoter, lambda $P_L$, promoter, β-lactamase promoter, lactose promoter, phoA promoter, T3 promoter, T7 promoter, or tac promoter (de Boer et al., 1983).

Promoters suitable for use with an expression construct of the invention in yeast cells include, but are not limited to, 3-phosphoglycerate kinase promoter, glyceraldehyde-3-phosphate dehydrogenase promoter, metallothionein promoter, alcohol dehydrogenase-2 promoter, and hexokinase promoter.

Expression constructs of the invention may optionally contain a transcription termination sequence, a translation termination sequence, a sequence encoding a signal peptide, and/or enhancer elements. Transcription termination regions can typically be obtained from the 3' untranslated region of a eukaryotic or viral gene sequence. Transcription termination sequences can be positioned downstream of a coding sequence to provide for efficient termination. A signal peptide sequence is a short amino acid sequence typically present at the amino terminus of a protein that is responsible for the relocation of an operably linked mature polypeptide to a wide range of post-translational cellular destinations, ranging from a specific organelle compartment to sites of protein action and the extracellular environment. Targeting gene products to an intended cellular and/or extracellular destination through the use of an operably linked signal peptide sequence is contemplated for use with the polypeptides of the invention. Classical enhancers are cis-acting elements that increase gene transcription and can also be included in the expression construct. Classical enhancer elements are known in the art, and include, but are not limited to, the CaMV 35S enhancer element, cytomegalovirus (CMV) early promoter enhancer element, and the SV40 enhancer element. Intron-mediated enhancer elements that enhance gene expression are also known in the art. These elements must be present within the transcribed region and are orientation dependent. Examples include the maize shrunken-1 enhancer element (Clancy and Hannah, 2002).

DNA sequences which direct polyadenylation of mRNA transcribed from the expression construct can also be included in the expression construct, and include, but are not limited to, an octopine synthase or nopaline synthase signal.

The expression constructs of the invention can also include a polynucleotide sequence that directs transposition of other genes, i.e., a transposon.

Expression constructs can also include one or more dominant selectable marker genes, including, for example, genes encoding antibiotic resistance and/or herbicide-resistance for selecting transformed cells. Antibiotic-resistance genes can provide for resistance to one or more of the following antibiotics: hygromycin, kanamycin, bleomycin, G418, streptomycin, paromomycin, neomycin, and spectinomycin. Kanamycin resistance can be provided by neomycin phosphotransferase (NPT II). Herbicide-resistance genes can provide for resistance to phosphinothricin acetyltransferase or glyphosate. Other markers used for cell transformation screening include genes encoding β-glucuronidase (GUS), β-galactosidase, luciferase, nopaline synthase, chloramphenicol acetyltransferase (CAT), green fluorescence protein (GFP), or enhanced GFP (Yang et al., 1996).

The subject invention also concerns polynucleotide vectors comprising a polynucleotide sequence of the invention that encodes a 2-phenylethanol dehydrogenase or phenylalanine decarboxylase of the invention. Unique restriction enzyme sites can be included at the 5' and 3' ends of an expression construct or polynucleotide of the invention to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.).

The subject invention also concerns oligonucleotide probes and primers, such as polymerase chain reaction (PCR) primers, that can hybridize to a coding or non-coding sequence of a polynucleotide of the present invention. Oligonucleotide probes of the invention can be used in methods for detecting nucleic acid sequences encoding a 2-phenylethanol dehydrogenase or a phenylalanine decarboxylase. Oligonucleotide primers of the invention can be used in PCR methods and other methods involving nucleic acid amplification. In a preferred embodiment, a probe or primer of the invention can hybridize to a polynucleotide of the invention under stringent conditions. Probes and primers of the invention can optionally comprise a detectable label or reporter molecule, such as fluorescent molecules, enzymes, radioactive moiety (e.g., $^3$H, $^{35}$S, $^{125}$I, etc.), and the like. Probes and primers of the invention can be of any suitable length for the method or assay in which they are being employed. Typically, probes and primers of the invention will be 10 to 500 or more nucleotides in length. Probes and primers that are 10 to 20, 21 to 30, 31 to 40, 41 to 50, 51 to 60, 61 to 70, 71 to 80, 81 to 90, 91 to 100 or more nucleotides in length are contemplated within the scope of the invention. Probes and primers of the invention can have complete (100%) nucleotide sequence identity with the polynucleotide sequence, or the sequence identity can be less than 100%. For example, sequence identity between a probe or primer and a sequence can be 99%, 98%, 97%, 96%, 95%, 90%, 85%, 80%, 75%, 70% or any other percentage sequence identity so long as the probe or primer can hybridize under stringent conditions to a nucleotide sequence of a polynucleotide of the invention. Exemplified probes and primers of the invention include those having the nucleotide sequence of SEQ ID NO: 3, or a functional fragment or variant of SEQ ID NO. 3.

Polynucleotides of the present invention can be composed of either RNA or DNA. Preferably, the polynucleotides are composed of DNA. The subject invention also encompasses those polynucleotides that are complementary in sequence to the polynucleotides disclosed herein. Polynucleotides and polypeptides of the invention can be provided in purified or isolated form.

Because of the degeneracy of the genetic code, a variety of different polynucleotide sequences can encode 2-phenylethanol dehydrogenase and phenylalanine decarboxylase enzymes of the present invention. A table showing all possible triplet codons (and where U also stands for T) and the amino acid encoded by each codon is described in Lewin (1985). In addition, it is well within the skill of a person trained in the art to create alternative polynucleotide sequences encoding the same, or essentially the same, 2-phenylethanol dehydrogenase or phenylalanine decarboxylase enzymes of the subject invention. These degenerate variant or alternative polynucleotide sequences are within the scope of the subject invention. As used herein, references to "essentially the same" sequence refers to sequences which encode amino acid substitutions, deletions, additions, or insertions which do not materially alter the functional activity of the polypeptide encoded by the polynucleotides of the present invention. Allelic variants of the nucleotide sequences encoding a 2-phenylethanol dehydrogenase or phenylalanine decarboxylase of the invention are also encompassed within the scope of the invention.

The subject invention also concerns an isolated plant 2-phenylethanol dehydrogenase. In one embodiment, the 2-phenylethanol dehydrogenase is a 2-phenylethanol dehydrogenase of tomato. In another embodiment, the 2-phenylethanol dehydrogenase is a 2-phenylethanol dehydrogenase of petunia. In a specific embodiment, a 2-phenylethanol dehydrogenase has an amino acid sequence as shown in SEQ ID NO: 2 or SEQ ID NO: 11, or an enzymatically active fragment or variant of SEQ ID NO: 2 or SEQ ID NO: 11. A 2-phenylethanol dehydrogenase enzyme of the invention can be purified using standard techniques known in the art. In one embodiment, a polynucleotide of the invention encoding a 2-phenylethanol dehydrogenase is incorporated into a microorganism, such as *E. coli*, and the 2-phenylethanol dehydrogenase expressed in the microorganism and then isolated therefrom.

The subject invention also concerns an isolated plant phenylalanine decarboxylase. In one embodiment, the phenylalanine decarboxylase is a phenylalanine decarboxylase of tomato. In a specific embodiment, a phenylalanine decarboxylase has an amino acid sequence as shown in SEQ ID NO: 5, 7, 9, or 13, or an enzymatically active fragment or variant thereof. A phenylalanine decarboxylase enzyme of the invention can be purified using standard techniques known in the art. In one embodiment, a polynucleotide of the invention encoding a phenylalanine decarboxylase is incorporated into a microorganism, such as *E. coli*, and the phenylalanine decarboxylase expressed in the microorganism and then isolated therefrom.

Polypeptides of the invention, and peptide fragments thereof, can be used to generate antibodies that bind specifically to a polypeptide of the invention, and such antibodies are contemplated within the scope of the invention. The antibodies of the invention can be polyclonal or monoclonal and can be produced and isolated using standard methods known in the art.

Polypeptide fragments according to the subject invention typically comprise a contiguous span of about or at least 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193; 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, or 327 amino acids of SEQ ID NO: 2; or a contiguous span of about or at least 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, or 464 amino acids of SEQ ID NO: 5; or a contiguous span of about or at least 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, or 470 amino acids of SEQ ID NO: 7, 9, or 13; or a contiguous span of about or at least 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, or 329 amino acids of SEQ ID NO: 11.

Polypeptide fragments of the subject invention can be any integer in length from at least about 25 consecutive amino acids to 1 amino acid less than the sequence shown in SEQ ID NO: 2, 5, 7, 9, 11, or 13. Thus, for SEQ ID NO: 2, a polypeptide fragment can be any integer of consecutive amino acids from about 25 to 327 amino acids; for SEQ ID NO: 5, a polypeptide fragment can be any integer of consecutive amino acids from about 25 to 464 amino acids; for SEQ ID NO: 7, 9, or 13, a polypeptide fragment can be any integer of consecutive amino acids from about 25 to 470 amino acids; for SEQ ID NO: 11, a polypeptide fragment can be any integer of consecutive amino acids from about 25 to 329 amino acids. The term "integer" is used herein in its mathematical sense and thus representative integers include: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, and/or 470.

Each polypeptide fragment of the subject invention can also be described in terms of its N-terminal and C-terminal positions. For example, combinations of N-terminal to C-terminal fragments of about 25 contiguous amino acids to 1 amino acid less than the full length polypeptide of SEQ ID NO: 2, 5, 7, 9, 11, and 13 are included in the present invention. Thus, using SEQ ID NO: 2 as an example, a 25 consecutive amino acid fragment could correspond to amino acids of SEQ ID NO: 2 selected from the group consisting of 1-25, 2-26, 3-27, 4-28, 5-29, 6-30, 7-31, 8-32, 9-33, 10-34, 11-35, 12-36, 13-37, 14-38, 15-39, 16-40, 17-41, 18-42, 19-43, 20-44, 21-45, 22-46, 23-47, 24-48, 25-49, 26-50, 27-51, 28-52, 29-53, 30-54, 31-55, 32-56, 33-57, 34-58, 35-59, 36-60, 37-61, 38-62, 39-63, 40-64, 41-65, 42-66, 43-67, 44-68, 45-69, 46-70, 47-71, 48-72, 49-73, 50-74, 51-75, 52-76, 53-77, 54-78, 55-79, 56-80, 57-81, 58-82, 59-83, 60-84, 61-85, 62-86, 63-87, 64-88, 65-89, 66-90, 67-91, 68-92, 69-93, 70-94, 71-95, 72-96, 73-97, 74-98, 75-99, 76-100, 77-101, 78-102, 79-103, 80-104, 81-105, 82-106, 83-107, 84-108, 85-109, 86-110, 87-111, 88, -112, 89-113, 90-114, 91-115, 92-116, 93-117, 94-118, 95-119, 96-120, 97-121, 98422, 99-123, 100-124, 101-125, 102-126, 103-127, 104-128, 105-129, 106-130, 107-131, 108-132, 109-133, 110-134, 111-135, 112-136, 113-137, 114-138, 115-139, 116-140, 117-141, 118-142, 119-143, 120-144, 121-145, 122-146, 123-147, 124-148, 125-149, 126-150, 127-151, 128-152, 129-153, 130-154, 131-155, 132-156, 133-157, 134-

158, 135-159, 136-160, 137-161, 138-162, 139-163, 140-164, 141-165, 142-166, 143-167, 144-168, 145-169, 146-170, 147-171, 148-172, 149-173, 150-174, 151-175, 152-176, 153-177, 154-178, 155-179, 156-180, 157-181, 158-182, 159-183, 160-184, 161-185, 162-186, 163-187, 164-188, 165-189, 166-190, 167-191, 168-192, 169-193, 170-194, 171-195, 172-196, 173-197, 174-198, 175-199, 176-200, 177-201, 178-202, 179-203, 180-204, 181-205, 182-206, 183-207, 184-208, 185-209, 186-210, 187-211, 188-212, 189-213, 190-214, 191-215, 192-216, 193-217, 194-218, 195-219, 196-220, 197-221, 198-222, 199-223, 200-224, 201-225, 202-226, 203-227, 204-228, 205-229, 206-230, 207-231, 208-232, 209-233, 210-234, 211-235, 212-236, 213-237, 214-238, 215-239, 216-240, 217-241, 218-242, 219-243, 220-244, 221-245, 222-246, 223-247, 224-248, 225-249, 226-250, 227-251, 228-252, 229-253, 230-254, 231-255, 232-256, 233-257, 234-258, 235-259, 236-260, 237-261, 238-262, 239-263, 240-264, 241-265, 242-266, 243-267, 244-268, 245-269, 246-270, 247-271, 248-272, 249-273, 250-274, 251-275, 252-276, 253-277, 254-278, 255-279, 256-280, 257-281, 258-282, 259-283, 260-284, 261-285, 262-286, 263-287, 264-288, 265-289, 266-290, 267-291, 268-292, 269-293, 270-294, 271-295, 272-296, 273-297, 274-298, 275-299, 276-300, 277-301, 278-302, 279-303, 280-304, 281-305, 282-306, 283-307, 284-308, 285-309, 286-310, 287-311, 288-312, 289-313, 290-314, 291-315, 292-316, 293-317, 294-318, 295-319, 296-320, 297-321, 298-322, 299-323, 300-324, 301-325, 302-326, 303-327, and 304-328. Similarly, the amino acids corresponding to all other fragments of sizes between 26 consecutive amino acids and 327 consecutive amino acids of SEQ ID NO: 2 are included in the present invention and can also be immediately envisaged based on these examples. Therefore, additional examples, illustrating various fragments of the polypeptides of SEQ ID NO: 2 are not individually listed herein in order to avoid unnecessarily lengthening the specification. Fragment embodiments as described above are also contemplated for the polypeptides of SEQ ID NO: 5, 7, 9, 11, and 13 taking into account that the polypeptides are 465, 471, 471, 330, and 471 amino acids in length, respectively, and are not individually listed herein in order to avoid unnecessarily lengthening the specification.

Polypeptide fragments comprising:

a) 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, or 327 consecutive amino acids of SEQ ID NO: 2;

b) 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, and 464 consecutive amino acids of SEQ ID NO: 5;

c) 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, and 470 consecutive amino acids of SEQ ID NO: 7, 9, or 13; and d) 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, and 329 consecutive amino acids of SEQ ID NO: 11 may alternatively be described by the formula "n to c" (inclusive), where "n" equals the N-terminal amino acid position and "c" equals the C-terminal amino acid position of the polypeptide. In this embodiment of the invention, "n" is an integer having a lower limit of 1 and an upper limit of the total number of amino acids of the full length polypeptide minus 24 (e.g., 328−24=304 for SEQ ID NO: 2). "c" is an integer between 25 and the number of amino acids of the full length polypeptide sequence (328 for SEQ ID NO: 2) and "n" is an integer smaller then "c" by at least 24. Therefore, for SEQ ID NO: 2, "n" is any integer selected from the list consisting of: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, and 304; and "c" is any integer selected from the group consisting of: 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, and 328 provided that "n" is a value less than "c" by at least 24. Every combination of "n" and "c" positions are included as specific embodiments of polypeptide fragments of the invention. Fragment embodiments as described above are also contemplated for the polypeptides of SEQ ID NO: 5, 7, 9, 11, and 13 taking into account that the polypeptides are 465, 471, 471, 330, and 471 amino acids in length, respectively, and are not individually listed herein in order to avoid unnecessarily lengthening the specification. All ranges used to describe any polypeptide fragment embodiment of the present invention are inclusive unless specifically set forth otherwise.

Fragments of a plant 2-phenylethanol dehydrogenase or phenylalanine decarboxylase of the invention, as described herein, can be obtained by cleaving the polypeptides of the invention with a proteolytic enzyme (such as trypsin, chymotrypsin, or collagenase) or with a chemical reagent, such as cyanogen bromide (CNBr). Alternatively, polypeptide fragments can be generated in a highly acidic environment, for example at pH 2.5. Polypeptide fragments can also be prepared by chemical synthesis or using host cells transformed with an expression vector comprising a polynucleotide encoding a fragment of a 2-phenylethanol dehydrogenase or phenylalanine decarboxylase enzyme of the invention, for example, a 2-phenylethanol dehydrogenase that is a fragment of the amino acid sequence shown in SEQ ID NO: 2 or SEQ ID NO: 11, or a phenylalanine decarboxylase that is a fragment of the amino acid sequence shown in SEQ ID NO: 5, 7, 9, or 13.

Substitution of amino acids other than those specifically exemplified or naturally present in a plant 2-phenylethanol dehydrogenase or phenylalanine decarboxylase enzyme of the invention are also contemplated within the scope of the present invention. For example, non-natural amino acids can be substituted for the amino acids of 2-phenylethanol dehydrogenase or phenylalanine decarboxylase, so long as the 2-phenylethanol dehydrogenase or phenylalanine decarboxylase enzyme having the substituted amino acids retains substantially the same biological activity as the 2-phenylethanol dehydrogenase or phenylalanine decarboxylase in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of 2-phenylethanol dehydrogenase and phenylalanine decarboxylase enzymes of the present invention are also encompassed within the scope of the invention.

Amino acids can be generally categorized in the following classes: non-polar, uncharged polar, basic, and acidic. Conservative substitutions whereby an 2-phenylethanol dehydrogenase or phenylalanine decarboxylase enzyme of the present invention having an amino acid of one class is replaced with another amino acid of the same class fall within the scope of the subject invention so long as the 2-phenylethanol dehydrogenase or phenylalanine decarboxylase enzyme having the substitution still retains substantially the same biological activity as the 2-phenylethanol dehydrogenase or phenylalanine decarboxylase enzyme that does not have the substitution. Polynucleotides encoding a 2-phenylethanol dehydrogenase or phenylalanine decarboxylase enzyme having one or more amino acid substitutions in the sequence are contemplated within the scope of the present invention. Table 3 below provides a listing of examples of amino acids belonging to each class.

TABLE 3

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Single letter amino acid abbreviations are defined in Table 4.

TABLE 4

| Letter Symbol | Amino Acid |
| --- | --- |
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

The subject invention also concerns variants of the polynucleotides of the present invention that encode enzymatically active 2-phenylethanol dehydrogenase or phenylalanine decarboxylase enzymes of the invention. Variant sequences include those sequences wherein one or more nucleotides of the sequence have been substituted, deleted, and/or inserted. The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Fragments and variants of 2-phenylethanol dehydrogenase and phenylalanine decarboxylase of the present invention can be generated as described herein and tested for the presence of enzymatic function using standard techniques known in the art. For example, for testing fragments and/or variants of a 2-phenylethanol dehydrogenase, the conversion of phenylacetaldehyde to 2-phenylethanol can be assayed according to the present invention. Thus, an ordinarily skilled artisan can readily prepare and test fragments and variants of a 2-phenylethanol dehydrogenase of the invention and determine whether the fragment or variant retains functional enzymatic activity relative to full-length or a wildtype plant 2-phenylethanol dehydrogenase. Similarly, an assay for the conversion of phenylalanine to phenethylamine can be used to assess enzymatic activity of fragments and/or variants of phenylalanine decarboxylase of the present invention.

Polynucleotides and polypeptides contemplated within the scope of the subject invention can also be defined in terms of more particular identity and/or similarity ranges with those sequences of the invention specifically exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

$$Tm=81.5\ C+16.6\ \text{Log}\ [\text{Na}+]+0.41(\%\ G+C)-0.61(\%\ \text{formamide})-600/\text{length of duplex in base pairs.}$$

Washes are typically carried out as follows:

(1) Twice at room temperature for 15 minutes in 1×SSPE, 0.1% SDS (low stringency wash).

(2) Once at Tm-20 C for 15 minutes in 0.2×SSPE, 0.1% SDS (moderate stringency wash).

As used herein, the terms "nucleic acid" and "polynucleotide" refer to a deoxyribonucleotide, ribonucleotide, or a mixed deoxyribonucleotide and ribonucleotide polymer in either single- or double-stranded form, and unless otherwise limited, would encompass known analogs of natural nucleotides that can function in a similar manner as naturally-occurring nucleotides. The polynucleotide sequences include the DNA strand sequence that is transcribed into RNA and the strand sequence that is complementary to the DNA strand that is transcribed. The polynucleotide sequences also include both full-length sequences as well as shorter sequences derived from the full-length sequences. Allelic variations of the exemplified sequences also fall within the scope of the subject invention. The polynucleotide sequence includes both the sense and antisense strands either as individual strands or in the duplex.

The subject invention also concerns cells transformed with a polynucleotide of the present invention encoding a 2-phenylethanol dehydrogenase of the invention. In one embodiment, the cell is transformed with a polynucleotide sequence comprising a sequence encoding the amino acid sequence shown in SEQ ID NO: 2, or an enzymatically active fragment or variant thereof. In a specific embodiment, the cell is transformed with a polynucleotide sequence shown in SEQ ID NO: 1, or a sequence encoding an enzymatically active fragment or variant of SEQ ID NO: 2. In one embodiment, the polynucleotide encoding the amino acid sequence shown in SEQ ID NO: 2 comprises nucleotides 172 to 1155 of the nucleotide sequence shown in SEQ ID NO: 1. In another embodiment, a cell is transformed with a polynucleotide sequence comprising a sequence encoding the amino acid shown in SEQ ID NO: 11, or an enzymatically active fragment or variant thereof. In a specific embodiment, a plant is transformed with a polynucleotide sequence shown in SEQ ID NO: 10, or a sequence encoding an enzymatically active fragment or variant of SEQ ID NO: 11. In one embodiment, the polynucleotide encoding the amino acid sequence shown in SEQ ID NO: 11 comprises nucleotides 1 to 990 of the nucleotide sequence shown in SEQ ID NO: 10.

The subject invention also concerns cells transformed with a polynucleotide of the present invention encoding a phenylalanine decarboxylase of the invention. In one embodiment, the cell is transformed with a polynucleotide sequence comprising a sequence encoding the amino acid sequence shown in SEQ ID NO: 5, 7, 9, or 13, or an enzymatically active fragment or variant thereof. In a specific embodiment, the cell is transformed with a polynucleotide sequence shown in SEQ ID NO: 4, 6, 8, or 12, or a sequence encoding an enzymatically active fragment or variant of SEQ ID NO: 5, 7, 9, or 13. In one embodiment, the polynucleotide encoding the amino acid sequence shown in SEQ ID NO: 5 comprises nucleotides 1 to 1395 of the nucleotide sequence shown in SEQ ID NO: 4. In another embodiment, the polynucleotide encoding the amino acid sequence shown in SEQ ID NO: 7, 9, or 13 comprises nucleotides 1 to 1413 of the nucleotide sequence shown in SEQ ID NO: 6, 8, or 12, respectively.

Preferably, the polynucleotide sequence is provided in an expression construct of the invention. The transformed cell can be a prokaryotic cell, for example, a bacterial cell such as *E. coli* or *B. subtilis*, or the transformed cell can be a eukaryotic cell, for example, a plant cell, including protoplasts, or an animal cell. Plant cells include, but are not limited to, dicotyledonous, monocotyledonous, and conifer cells. In one embodiment, the plant cell is a cell from tomato. In an exemplified embodiment, the plant cell is a cell from a petunia plant. Animal cells include human cells, mammalian cells, avian cells, and insect cells. Mammalian cells include, but are not limited to, COS, 3T3, and CHO cells.

Plants, plant tissues, and plant cells transformed with or bred to contain a polynucleotide of the invention are also contemplated by the present invention. Plants within the scope of the present invention include monocotyledonous plants, such as, for example, rice, wheat, barley, oats, sorghum, maize, sugarcane, pineapple, onion, bananas, coconut, lilies, grasses, and millet. Plants within the scope of the present invention also include dicotyledonous plants, such as, for example, tomato, peas, alfalfa, melon, chickpea, chicory, clover, kale, lentil, soybean, tobacco, potato, sweet potato, radish, cabbage, rape, grape, sunflower, lettuce, cucumber, watermelon, apple, citrus (e.g., orange, lemon, tangerine, grapefruit, lime), pear, plum, peach, fig, currant, muskmelon, squash, cherry, sugar beet, tea, strawberry, blackberry, blueberry, raspberry, loganberry, rose, chrysanthemum, sweet pepper, eggplant, and cotton; and conifers. Preferably, the plant, plant tissue, or plant cell is tomato. Ornamental and herb plants containing a polynucleotide of the invention are also contemplated within the scope of the invention. Ornamental plants include roses, petunias, carnations, orchids, tulips, gardenias, and the like. Herb plants include parsley, sage, rosemary, thyme, and the like. Techniques for transforming plant cells with a gene are known in the art and include, for example, *Agrobacterium* infection, biolistic methods, electroporation, calcium chloride treatment, etc. Transformed cells can be selected, redifferentiated, and grown into plants using standard methods known in the art. Thus, the subject invention also concerns transgenic plants, and tissue and cells thereof, that have a polynucleotide of the invention incorporated into their genome. The seeds and progeny of any transformed or transgenic plant cells or plants of the invention are also included within the scope of the present invention.

The subject invention also concerns methods for providing a plant with increased flavor or fragrance of fruit or flower by incorporating one or more polynucleotide of the present invention in the genome of the plant cells and expressing the polypeptide encoded by the polynucleotide. In one embodiment, a plant is grown from a transformed plant cell of the invention. Preferably, the polynucleotide encodes a 2-phenylethanol dehydrogenase or a phenylalanine decarboxylase derived from the same plant species as the plant. In one embodiment, the plant is tomato. In another embodiment, the plant is a rose or other scented ornamental. In those embodiments, where increased flavor of fruit is desired, preferably the polynucleotide(s) of the invention is expressed in the fruit. In those embodiments where increased or enhanced fragrance of fruit or flower is desired, preferably the polynucleotide(s) of the invention is expressed in the fruit and/or flower. In a specific embodiment, a polynucleotide encoding an amino acid sequence shown in SEQ ID NO: 2, or an enzymatically active fragment or variant thereof, is incorporated into a plant genome. In one embodiment, the plant is a tomato plant. In an exemplified embodiment, the plant is a petunia plant. In a specific embodiment, the polynucleotide comprises a nucleotide sequence shown in SEQ ID NO: 1, or a sequence encoding an enzymatically active fragment or variant of SEQ ID NO: 2. In one embodiment, the polynucleotide encoding the amino acid sequence shown in SEQ ID NO: 2 comprises nucleotides 172 to 1155 of the nucleotide sequence shown in SEQ ID NO: 1. In a specific embodiment, a polynucleotide encoding an amino acid sequence shown in SEQ ID NO: 11, or an enzymatically active fragment or variant thereof, is incorporated into a tomato plant genome. In a specific embodiment, the polynucleotide comprises a nucleotide sequence shown in SEQ ID NO: 10, or a sequence encoding an enzymatically active fragment or variant of SEQ ID NO: 11. In one embodiment, the polynucleotide encoding the amino acid sequence shown in SEQ ID NO: 11 comprises nucleotides 1 to 990 of the nucleotide sequence shown in SEQ ID NO: 10. In another specific embodiment, a polynucleotide encoding an amino acid sequence shown in SEQ ID NO: 5, 7, 9, or 13, or an enzymatically active fragment or variant thereof, is incorporated into a tomato plant genome. In a specific embodiment, the polynucleotide comprises a nucleotide sequence shown in SEQ ID NO: 4, 6, 8, or 12, or a sequence encoding an enzymatically active fragment or variant of SEQ ID NO: 5, 7, 9, or 13. In one embodiment, the polynucleotide encoding the amino acid sequence shown in SEQ ID NO: 5 comprises nucleotides 1 to 1395 of the nucleotide sequence shown in SEQ ID NO: 4. In another embodiment, the polynucleotide encoding the amino acid sequence shown in SEQ ID NO: 7 or 9 comprises nucleotides 1 to 1413 of the nucleotide sequence shown in SEQ ID NO: 6 or 8. The level of expression of a polynucleotide of the invention can be manipulated using standard methods known in the art, including the use of promoters that provide for low, intermediate or high levels of expression.

The subject invention also concerns methods for producing 2-phenylethanol. In one embodiment, recombinantly produced 2-phenylethanol dehydrogenase of the invention can be used to enzymatically convert a suitable substrate, such as phenylacetaldehyde, into 2-phenylethanol. In another embodiment, a microorganism, such as yeast or *E. coli*, can be transformed with and express a polynucleotide encoding a plant 2-phenylethanol dehydrogenase enzyme of the invention and, optionally, one or more enzymes, such as phenylalanine decarboxylase and phenylethylamine oxidase, that through their enzymatic reactions result in a suitable substrate (e.g., phenylacetaldehyde) for 2-phenylethanol dehydrogenase to convert to 2-phenylethanol. Transformed microorganisms can be grown and polynucleotides expressed constitutively or induced, and 2-phenylethanol isolated from the microorganisms.

The subject invention also concerns methods for producing phenethylamine. In one embodiment, recombinantly produced phenylalanine decarboxylase of the invention can be used to enzymatically convert a suitable substrate, such as phenylalanine, into phenethylamine. In another embodiment, a microorganism, such as yeast or *E. coli*, can be transformed with and express a polynucleotide encoding a plant phenylalanine decarboxylase of the invention and, optionally, one or more enzymes, that through their enzymatic reactions result in a suitable substrate (e.g., phenylalanine) for phenylalanine decarboxylase to convert to phenethylamine. Transformed microorganisms can be grown and polynucleotides expressed constitutively or induced, and phenethylamine isolated from the microorganisms.

All patents, patent applications, provisional applications, and publications referred to or cited herein are incorporated by reference in their entirety, including all figures and tables, to the extent they are not inconsistent with the explicit teachings of this specification.

Materials and Methods

Plant Material.

Tomato (*Lycopersicon esculentum* Mill. cv. M82) and *Lycopersicon pennellii* introgression lines 8-2 and 8-2-1 (Eshed and Zamir, 1994) were grown in the greenhouse or field under standard conditions. Petunia plants were grown in a greenhouse under standard conditions.

Volatile Collection.

Volatiles were collected from approximately 100 g of chopped ripe tomato fruit as described by Schmelz et al. (2003). Petunia volatiles were collected from five flowers from each plant harvested at dusk. Volatiles were separated on an Agilent DB-5 column and analyzed on an Agilent 6890N gas chromatograph.

Microarrays.

Tomato cDNA microarrays were as described in Moore et al. (2002). Total RNAs were isolated as described earlier (Clardi et al., 2000). Arrays were hybridized with Cy3 or Cy5 labeled cDNAs from M82 and introgression line 8-2-1 fruit. Arrays were performed multiple times and with dyes reversed to ensure accuracy of the expression data.

2-Phenylethanol Dehydrogenase Expression in *E. coli*.

A full-length 2-phenylethanol dehydrogenase cDNA was cloned by 5' RACE from tomato fruit cDNA using primer 5'-TCCTTGGCCCCACCAAGAGAAAGCAAGT-GCTGCGT-3' (SEQ ID NO: 3). Following sequence analysis the full-length cDNA was obtained by PCR. The coding region was cloned into vector pDEST15 containing a GST tag (Invitrogen) by recombination, and transformed into *E. coli* strain BL21-SI (Invitrogen) for inducible protein expression. Enzyme activity of crude *E. coli* extracts was determined by the method of Larroy et al. (2002) using phenylacetaldehyde, cinnamaldehyde or vanillin as a substrate.

Production of Transgenic Petunia Plants.

The full-length 2-phenylethanol dehydrogenase cDNA (SEQ ID NO: 1) was cloned in a vector under the control of the figwort mosaic virus 35S promoter (Richins et al., 1987) and followed by the *Agrobacterium* nopaline synthase (nos) 3' terminator. The transgene was introduced into *Petunia hybrida* cv. Mitchell Diploid by the method of Wilkinson et al. (1997) with kanamycin resistance as a selectable marker.

In Vivo Phenylalanine Decarboxylase Activity Assays.

Tomato (M82 or introgression line 8-2-1) fruit pericarp disks were incubated with 1 µCi universally-labeled $^{14}$C-phenylalanine for 8 hr. Production of $^{14}$C—$CO_2$ was measured by incubating the pericarp disk in a sealed flask with a 2N KOH filter paper disk suspended above the pericarp disk, followed by scintillation counting. $^{14}$C-phenylalanine and $^{14}$C-phenylethylamine were extracted from the pericarp disk and separated using an AG-1 (OH—) column in series with a BioRex-70 column as described by Rontein et al. (2001). Production of $^{14}$C-phenylethylamine was confirmed by thin layer chromatography.

Phenylalanine Decarboxylase Expression in *E. Coli*.

The full-length aromatic amino acid decarboxylase cDNAs were cloned by sequencing putative clones from the TIGR database. Following sequence analysis the full-length coding sequence was obtained by PCR, and cloned into vector pENTR/D-TOPO. The coding region was then cloned into vector pDEST15 containing a GST tag (Invitrogen) by recombination, and transformed into *E. coli* strain BL21-AI (Invitrogen) for inducible protein expression. Production of the recombinant protein was confirmed by protein blotting with anti-GST antibodies. Enzyme activity was determined by growing *E. coli* strains expressing the aromatic amino acid decarboxylases in media containing 19.4 mM phenylalanine. Volatile compounds were extracted from the cultures using an equal volume of hexanes. Extracts were concentrated and analyzed by gas chromatography on an Agilent DB-5 column on an Agilent 6890N gas chromatograph. Identification of phenethylamine was confirmed by GC-mass spectrometry as described by Schmelz et al. (2001).

Southern Blotting.

DNA from *L. esculentum* M82 or 8-2-1 or *L. pennellii* leaves was digested with EcoRI, EcoRV, DraI, HaeIII or ScaI. Southern blotting was performed as described by Sambrook et al. (1989).

Following are examples which illustrate procedures for practicing the invention. These examples should not be construed as limiting. All percentages are by weight and all solvent mixture proportions are by volume unless otherwise noted.

Example 1

Volatiles Analysis

Figures 1, 5A:
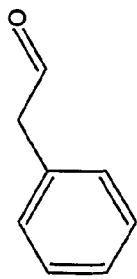
FIGS. 5A, 5B, and 5C show the result of alcohol dehydrogenase activities of 2-phenylethanol dehydrogenase on phenylacetaldehyde and related substrates. Activity is determined by the disappearance of substrate and a reduction in OD (340 nm). Highest activity levels are observed with phenylacetaldehyde as a substrate.
Figure 5A:
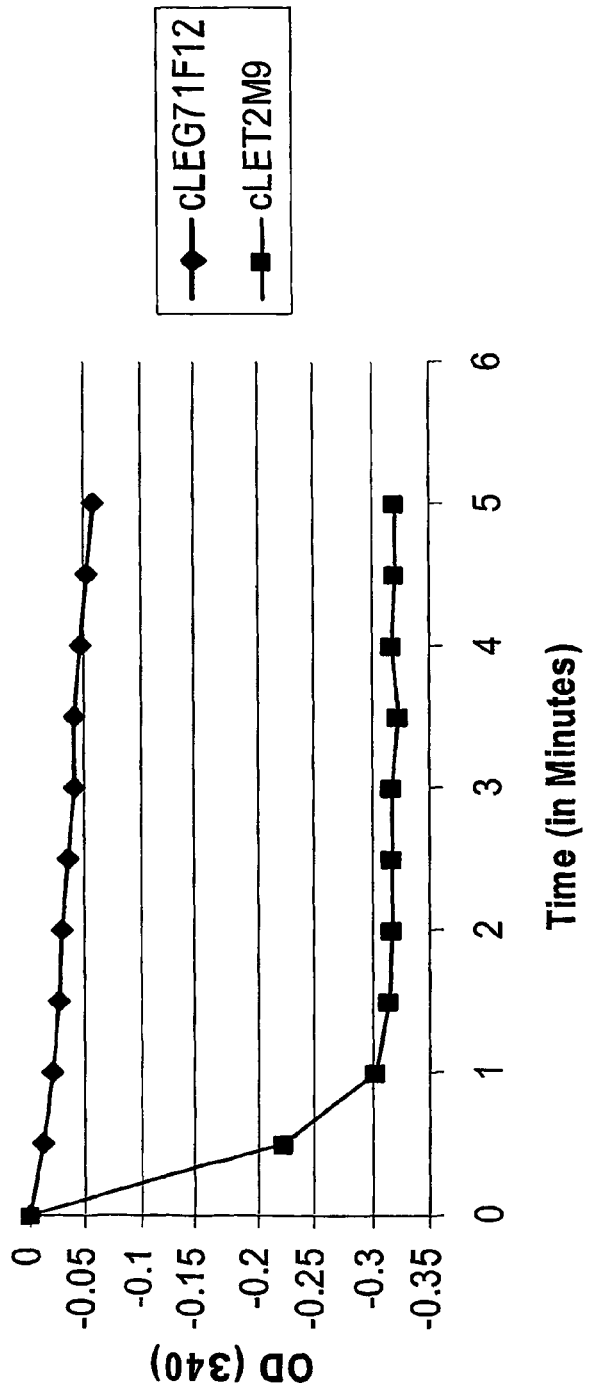
Figures 1, 5B:
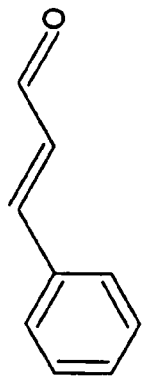
Figure 5B:
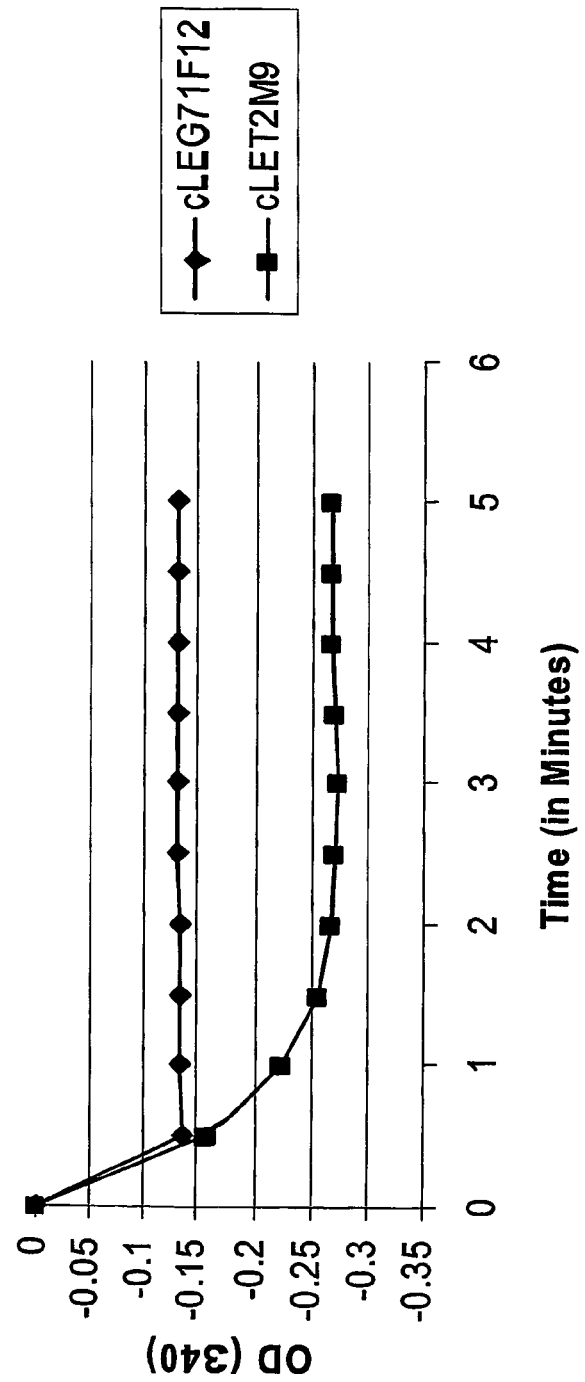
Figures 1, 5C:
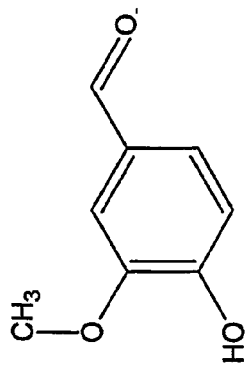
Figure 5C:
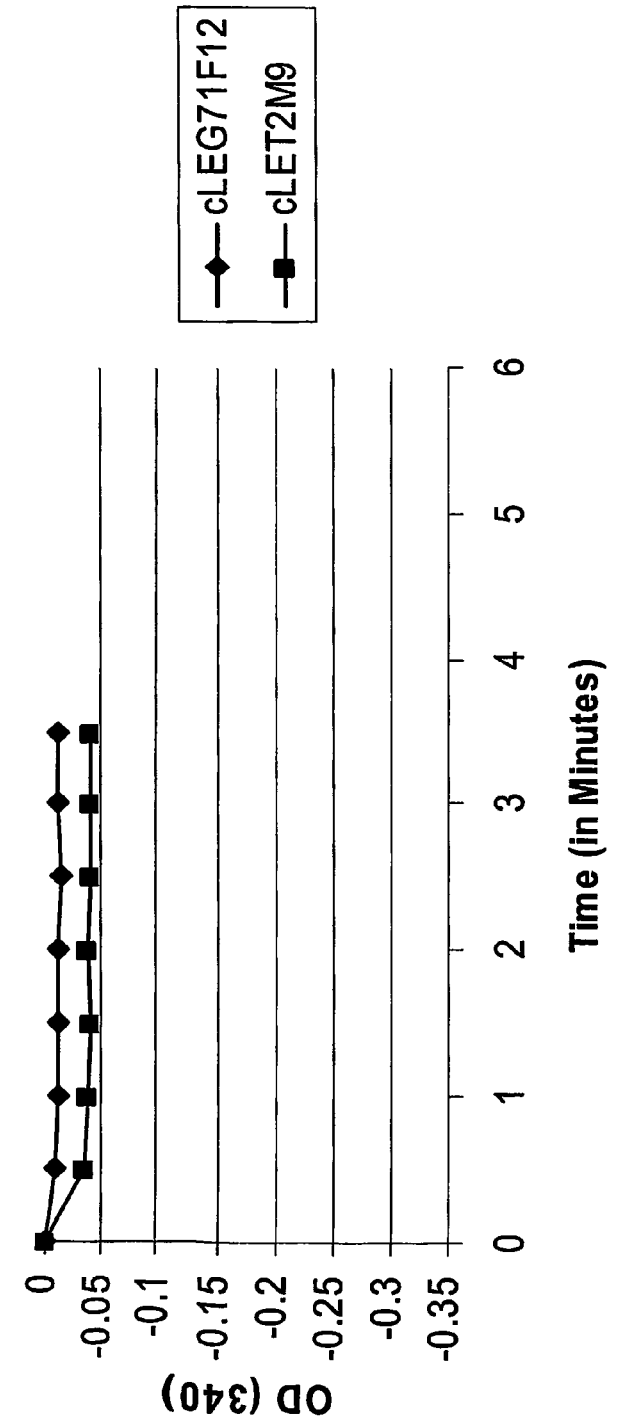

Volatiles analysis by GC on a DB5 column indicated high levels of phenylacetaldehyde and 2-phenylethanol in ripe fruit from *L. pennellii* introgression line (IL) 8-2-1. Levels of other tomato volatiles were similar to control M82 ripe fruit (FIG. 1). Levels of 2-phenylethanol were approximately 250× higher in 8-2-1 fruit than in M82 fruit. Phenylacetaldehyde levels in IL8-2-1 fruit were approximately 20× higher than in control fruit (FIG. 2). IL8-2-1 fruit had a distinct floral (rose-like) aroma consistent with the floral aromas of phenylacetaldehyde and 2-phenylethanol.

Example 2

Microarray Analysis

Microarrays containing approximately 3,000 tomato cDNAs indicated that an alcohol dehydrogenase gene (cLET2M9) was more highly expressed in IL8-2-1 fruit than in control M82 fruit; whereas, a related tomato alcohol dehydrogenase gene was not upregulated in IL8-2-1 fruit (Table 5).

TABLE 5

Microarray gene expression data for two alcohol dehydrogenase-like genes

| Microarray clone | Ratio |
|---|---|
| cLET2M9 | +2.2 |
| cLEG71F12 | −2.35 |

RNAs extracted from M82 and introgression line 8-2-1 fruit were compared using cDNA microarrays. Positive values indicate higher RNA expression levels in introgression line 8-2-1 fruit; negative values indicate higher expression in M82 fruit.

Figure 4:
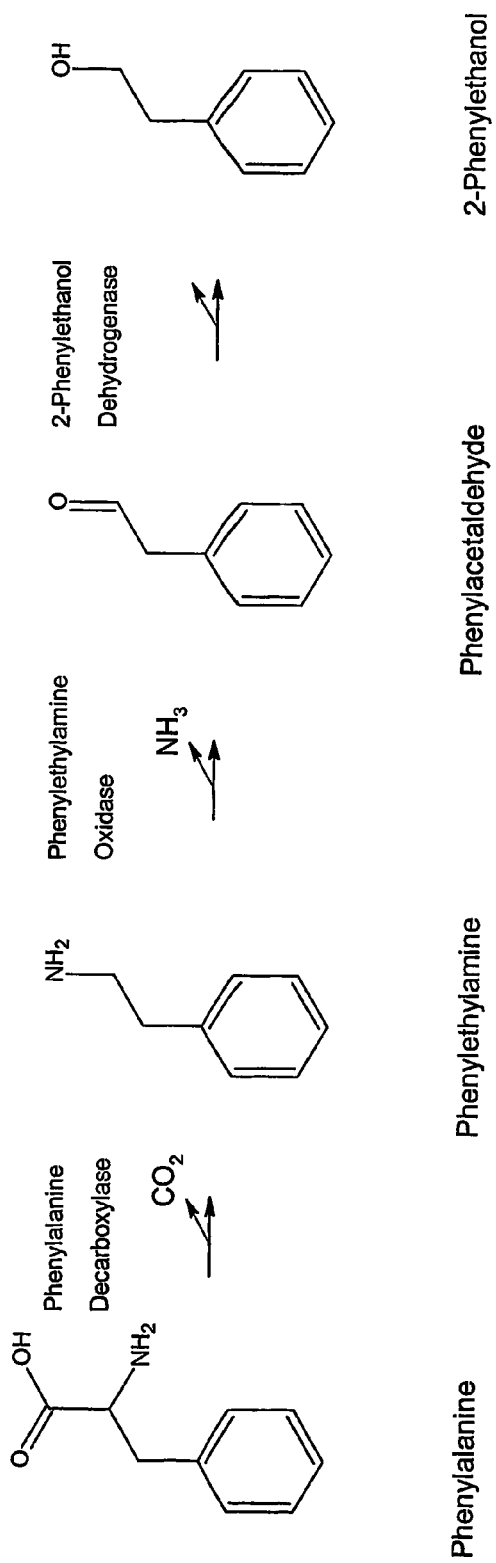
FIG. 4 shows a pathway for production of the volatiles phenylacetaldehyde and 2-phenylethanol in plants. Phenylalanine is decarboxylated by phenylalanine decarboxylase to form phenethylamine. Phenethylamine is then converted to phenylacetaldehyde by an amine oxidase, followed by conversion to 2-phenylethanol by 2-phenylethanol dehydrogenase.

Since clone cLET2M9 was only a partial cDNA, the full-length cDNA sequence for this clone was obtained by 5' RACE. The full-length cDNA sequence of 2-phenylethanol dehydrogenase was then obtained by PCR, and confirmed by sequence analysis (FIG. 3A). The deduced amino acid sequence of the 2-phenylethanol dehydrogenase is shown in FIG. 3B (SEQ ID NO: 2). In plants, a substrate such as phenylacetaldehyde can be converted to 2-phenylethanol by 2-phenylethanol dehydrogenase (FIG. 4).

Example 3

Enzyme Activity

The 2-phenylethanol dehydrogenase coding region of the full-length cLET2M9 and the related cLEG71F12 were cloned in vector pDEST15 with a GST tag and transformed into *E. coli* BL21-SI cells for inducible expression. The production of recombinant protein in *E. coli* was determined by Western blotting with an anti-GST antibody. Alcohol dehydrogenase activities on phenylacetaldehyde and several related substrates were determined spectrophotometrically by the reduction in levels of NADPH and a decrease in $OD_{340}$ (FIG. 5). The highest level of activity was observed with phenylacetaldehyde as a substrate. Lower activity levels were also observed with cinnamaldehyde as a substrate, whereas negligible activity was seen with vanillin as a substrate. Protein from cLEG71F12 expressed in *E. coli* showed very little activity on the three substrates tested.

Example 4

Expression of 2-Phenylethanol Dehydrogenase in Transgenic Petunia

Figure 6A:
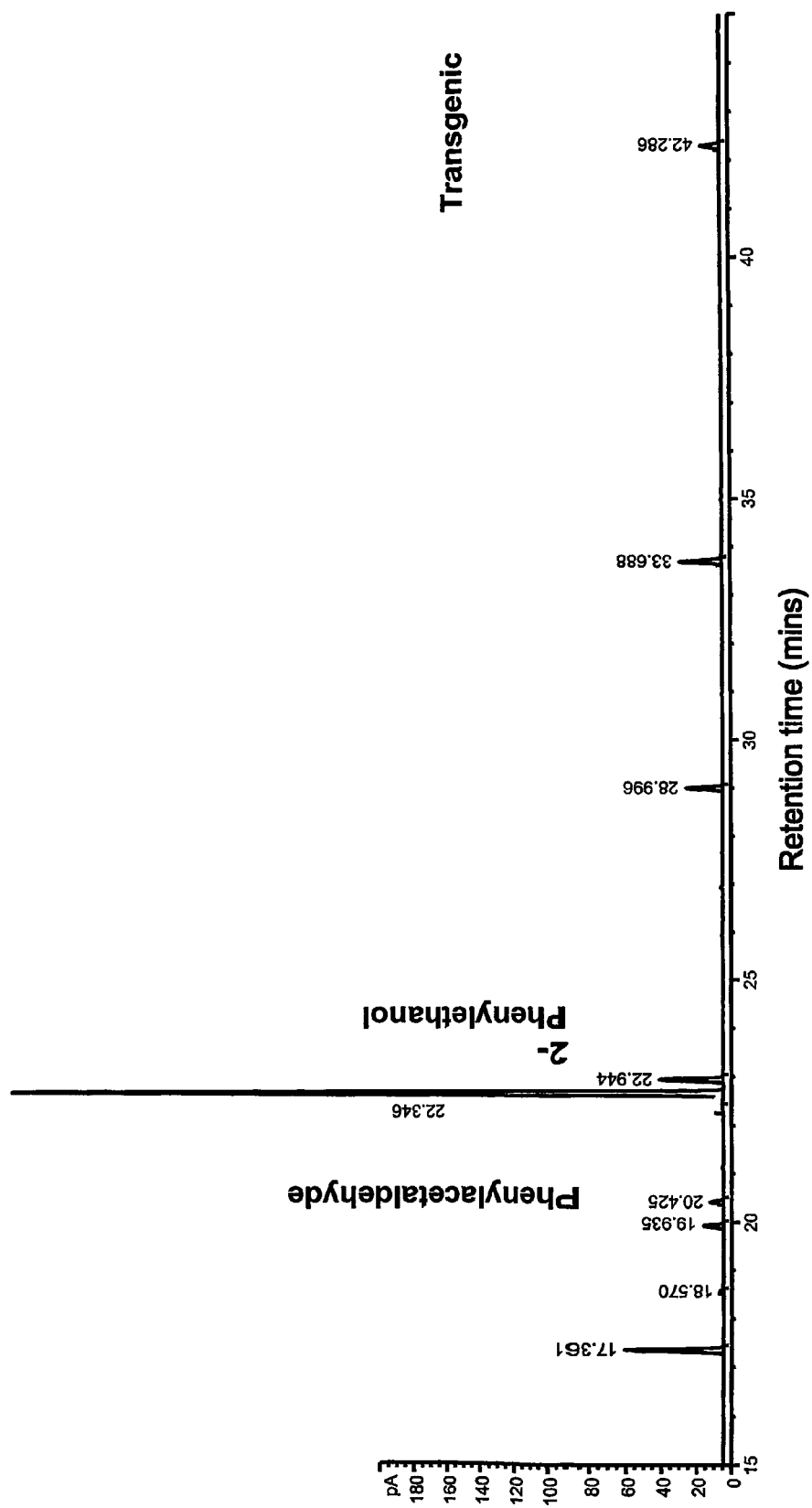
FIGS. 6A and 6B show the result of GC profiles of volatiles emitted from wild-type Mitchell Diploid (MD) petunia flowers and transgenic petunia flowers expressing a tomato 2-phenylethanol dehydrogenase gene. In transgenic flowers, higher levels of 2-phenylethanol and lower levels of phenylacetaldehyde are observed as compared to wild-type flowers.
Figure 6B:
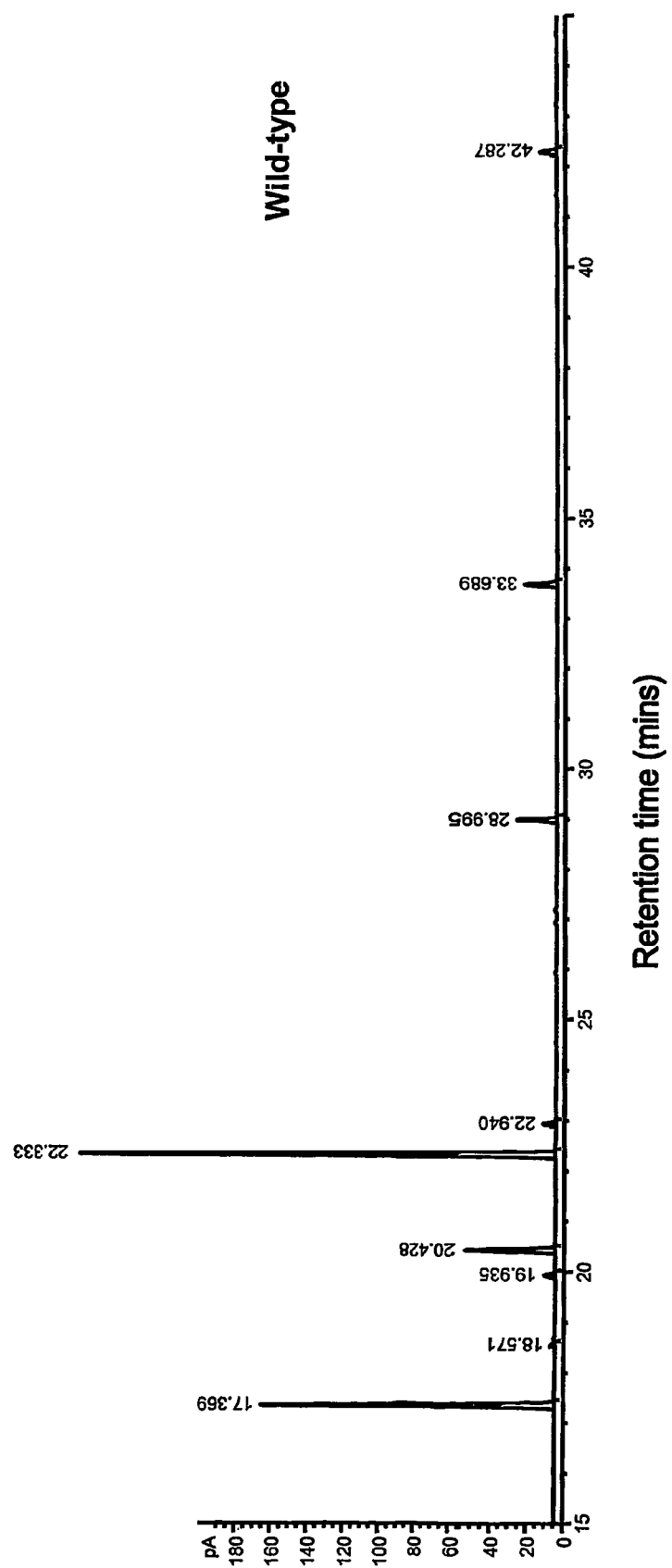
Figure 7:
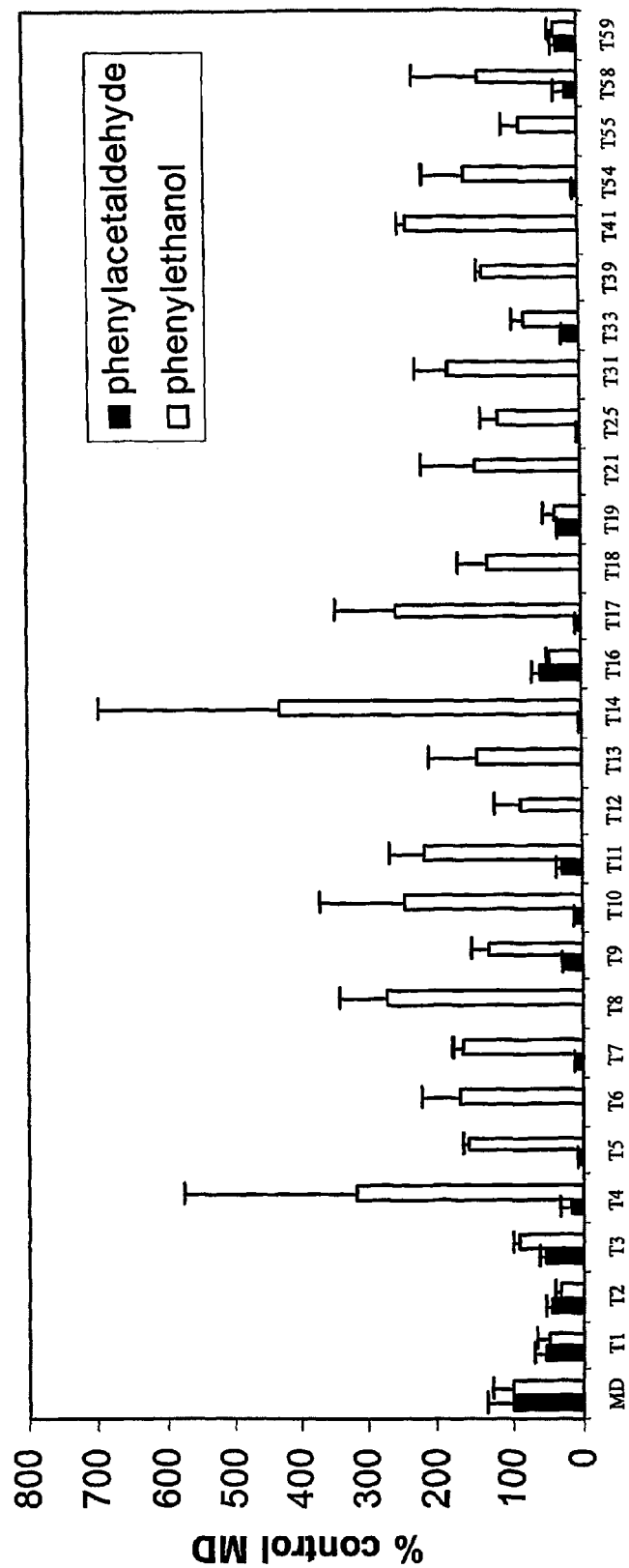
FIG. 7 is a graph of the levels of 2-phenylethanol and phenylacetaldehyde emitted from petunia flowers of wild-type Mitchell Diploid (MD) and transgenic lines expressing a tomato 2-phenylethanol dehydrogenase gene.

Full-length tomato 2-phenylethanol dehydrogenase cDNA was introduced into petunia (cv. Mitchell Diploid) under control of the constitutively expressed figwort mosaic virus promoter. Several transgenic petunia lines had high levels of expression of the tomato gene in flowers (data not shown). Wild-type petunia flowers emit relatively high levels of phenylacetaldehyde and lower levels of 2-phenylethanol. However, the transgenic petunia flowers expressing the polynucleotide encoding tomato 2-phenylethanol dehydrogenase have higher levels of 2-phenylethanol and lower levels of phenylacetaldehyde than wild-type flowers (FIG. 6). Levels of other petunia flower volatiles were similar to wild-type in the transgenic flowers. A range of phenylacetaldehyde and 2-phenylethanol levels were seen in the transgenic lines, however the majority of the lines had higher levels of 2-phenylethanol and lower levels of phenylacetaldehyde than wild-type flowers (FIG. 7). Overall, these data indicate that the introduction of the 2-phenylethanol dehydrogenase tomato transgene results in the conversion of phenylacetaldehyde to 2-phenylethanol in petunia flowers.

Example 5

Activity of 2-Phenylethanol Dehydrogenase on Various Substrates

Kin's for alcohol dehydrogenase activities of *E. coli* expressed LePEDH on phenylacetaldehyde and related substrates. The 2-phenylethanol dehydrogenase coding region of the full-length cLET2M9 was cloned in vector pDEST17 with a His tag and transformed into *E. coli* BL21-AI cells for inducible expression. Alcohol dehydrogenase activities on phenylacetaldehyde and several related substrates were determined. The highest level of activity was observed with phenylacetaldehyde as a substrate. Lower activity levels were also observed with cinnamaldehyde and benzaldehyde as substrates, whereas no detectable activity was seen with salicylaldehyde as a substrate.

TABLE 6

Substrate specificity of LePEDH

| Substrate | Km (µM) |
|---|---|
| Phenylacetaldehyde | 42.3 |
| Benzaldehyde | 240.1 |
| Cinnamaldehyde | 428.9 |
| NADPH | 54.2 |

Example 6

In Vivo Aromatic Amino Acid Decarboxylase Activity

A pathway for the formation of 2-phenylethanol in plants is shown in FIG. 4. In the pathway, phenylalanine is converted to phenethylamine by phenylalanine decarboxylase, followed by conversion of phenethylamine to phenylacetaldehyde by an amine oxidase. Phenylacetaldehyde is then converted to 2-phenylethanol by a 2-phenylethanol dehydrogenase. To establish the first step in this pathway, tomato fruit pericarp disks were incubated with $^{14}C$-phenylalanine. The formation of $^{14}C$-phenethylamine and $^{14}C$—$CO_2$, the products of the decarboxylase reaction were then determined (Table 7). Higher levels of both phenethylamine and $CO_2$ were formed in the IL8-2-1 pericarp disks than in the control M82 pericarp disks (Table 7), and correlate with the higher levels of phenylacetaldehyde and 2-phenylethanol in IL8-2-1 tomato fruit. These results indicate that phenethylamine can be an intermediate in the pathway to phenylacetaldehdye and 2-phenylethanol.

TABLE 7

Phenylalanine decarboxylase activity of M82 and IL8-2-1 tomato pericarp disks fed $^{14}C$ phenylalanine.

| Line | nCi $CO_2$ | nCi phenethylamine |
|---|---|---|
| M82 | 0.96 ± 0.05 | 0.36 ± 0.02 |
| 8-2-1 | 5.16 ± 2.36 | 2.08 ± 0.39 |

Pericarp disks were fed 1 µCi universally labeled $^{14}C$-phenylalanine for 8 hours, and amounts of $^{14}C$—$CO_2$ and $^{14}C$-phenethylamine produced were determined.

Example 7

Identification of Putative Aromatic Amino Acid Decarboxylase Genes

Conversion of phenylalanine to phenethylamine would be catalyzed by a phenylalanine decarboxylase. Therefore, the tomato sequence databases were searched for cDNAs with similarity to other aromatic amino acid decarboxylases. Several clones of L. esculentum cDNA sequences were identified, although two were more similar to histidine decarboxylases than aromatic amino acid decarboxylases. The full-length coding sequence of each of these genes was obtained by PCR, and confirmed by sequence analysis.

Example 8

Enzyme Activity

Figure 13A:
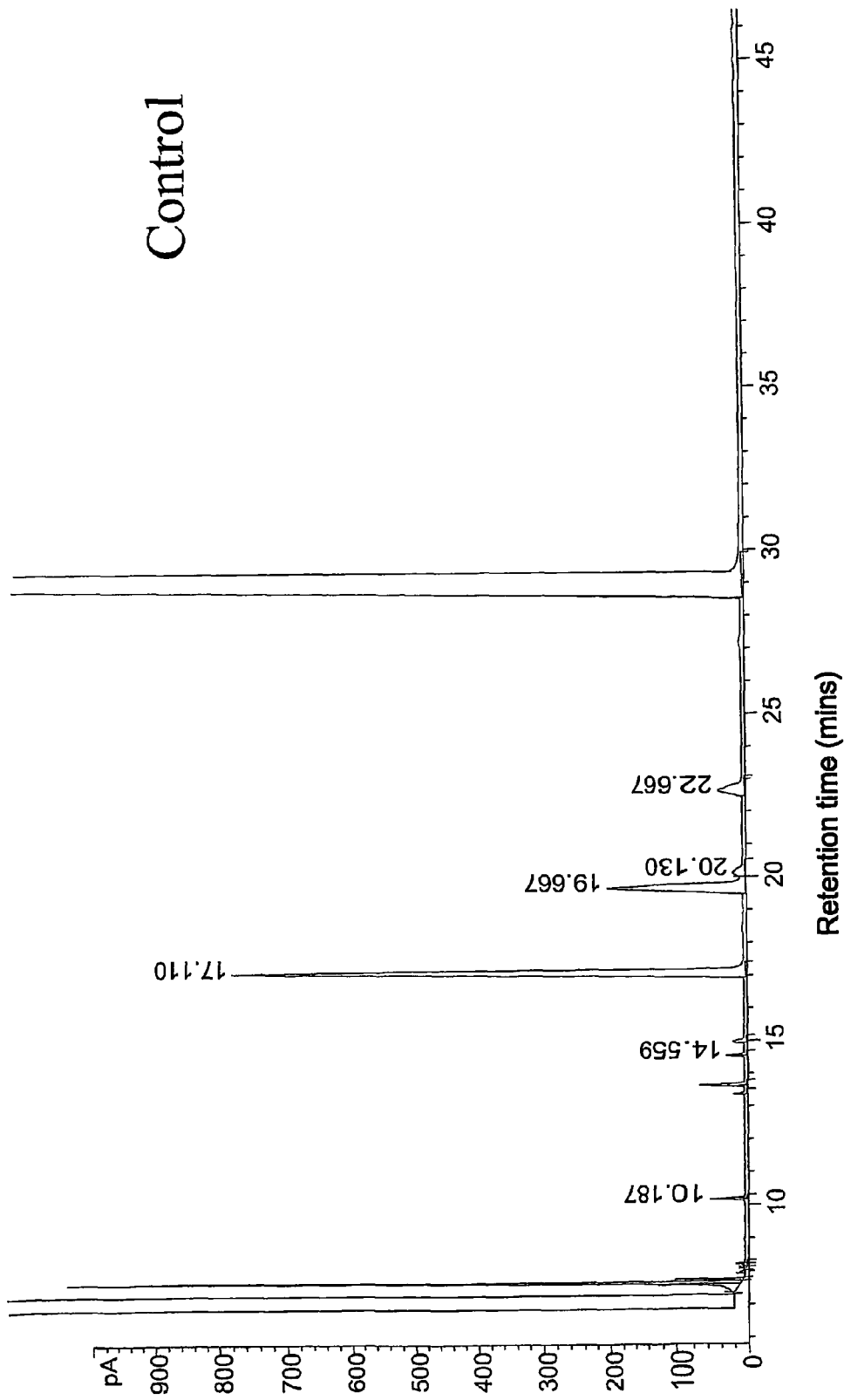
FIGS. 13A, 13B, and 13C show gas chromatography profiles of volatile compounds extracted from E. coli cultures expressing the tomato aromatic amino acid decarboxylase genes cLEC73K23 and cLEC75E21. E. coli expressing these tomato genes produce phenethylamine in media containing phenylalanine, while control E. coli cultures do not.
Figure 13B:
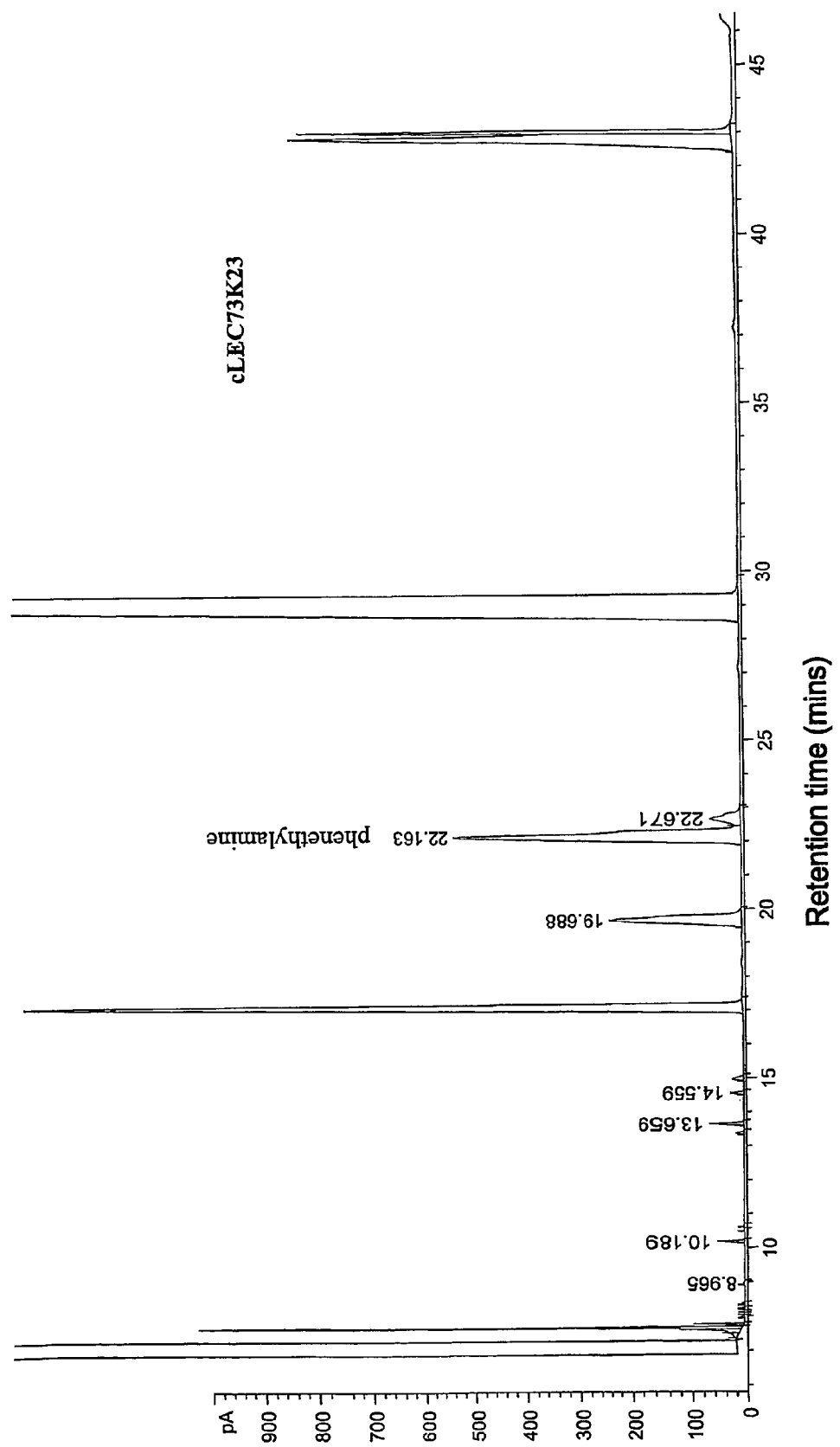
Figure 13C:
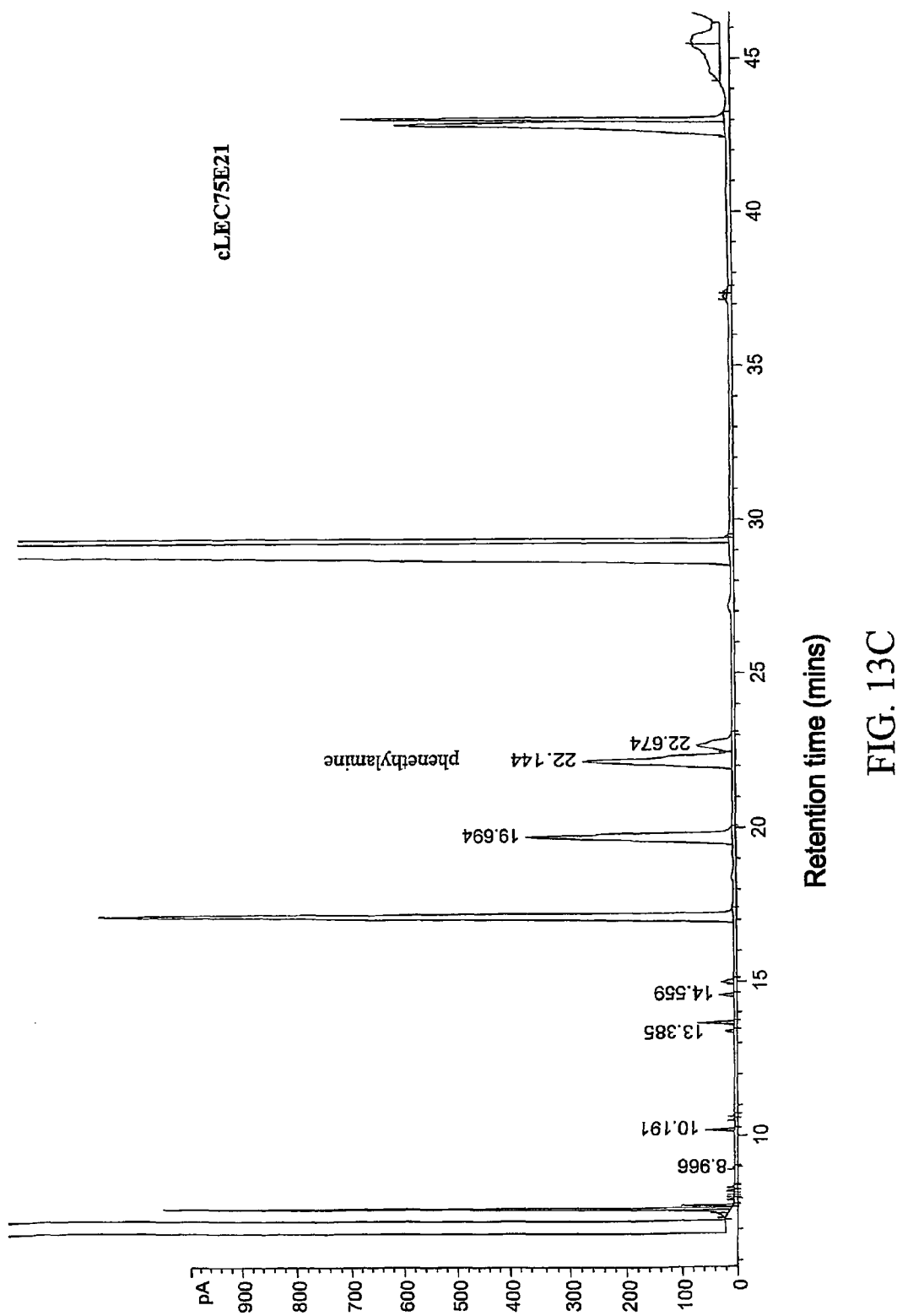

The coding regions of the full-length aromatic amino acid decarboxylases were cloned in vector pDEST15 with a GST tag and transformed into E. coli BL21-SI cells for inducible expression. The production of recombinant proteins in E. coli was confirmed by Western blotting with an anti-GST antibody. E. coli cultures expressing the putative aromatic amino acid decarboxylases were grown in the presence of phenylalanine. Volatile compounds were extracted from these cultures and analyzed by gas chromatography. E. coli cultures expressing two putative aromatic amino acid decarboxylases (cLEC73K23 and cLEC75E21) produced a compound with the same retention time as phenethylamine, while control cultures did not (FIG. 13). E. coli cultures expressing three other putative amino acid decarboxylases did not produce phenethylamine. The presence of phenethylamine in the samples was confirmed by GC-MS. The nucleic acid coding sequences and amino acid sequences of the phenylalanine decarboxylases are shown in FIGS. 8A-8B (SEQ ID NO: 4 and SEQ ID NO: 5) and FIGS. 9A-9B (SEQ ID NO: 6 and SEQ ID NO: 7). The cLEC73K23 and cLEC75E21 cDNA sequences exhibit 79% identity to one another, whereas the amino acid sequences are 85% similar and 81% identical to each other.

Example 9

Southern Blotting

Figure 10:
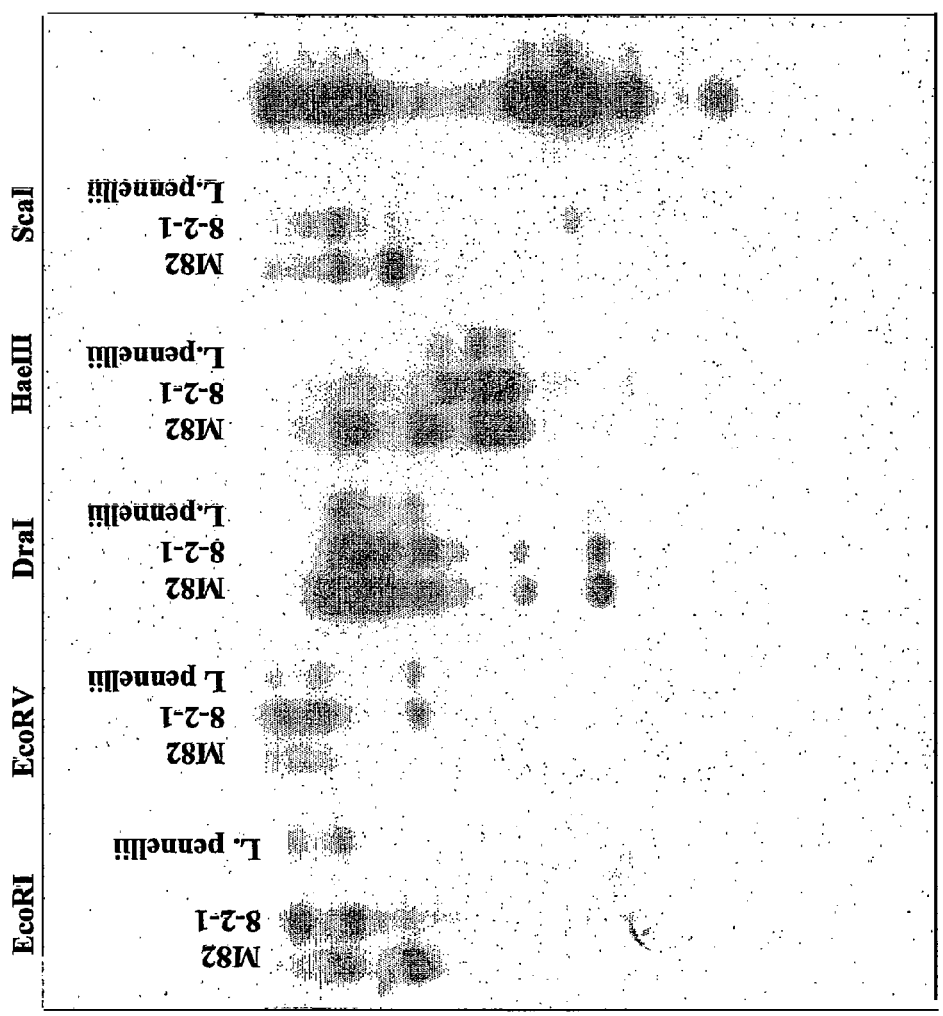
FIG. 10 is a Southern blot showing that cLEC73K23 is present on the L. pennellii introgression line (IL) 8-2-1 on tomato chromosome 8. Restriction patterns of L. pennellii and IL8-2-1 genomic DNA hybridized to the cLEC73K23 cDNA are identical, whereas L. esculentum M82 restriction patterns are different.

To determine if either of the genes with phenylalanine decarboxylase activity could be responsible for the altered levels of phenylalanine-derived volatiles in 8-2-1 fruit with the L. pennellii introgression on chromosome 8, Southern blots on M82, 8-2-1 and L. pennellii genomic DNA were performed using cLEC73K23 as a probe. Polymorphisms between M82 and L. pennellii were observed with EcoRI, EcoRV and ScaI (FIG. 10). With each of these enzymes the 8-2-1 restriction pattern was identical to L. pennellii, indicating that the cLEC73K23 gene in introgression line 8-2-1 came from the L. pennellii parent.

Example 10

Cloning of the L. pennellii cLEC73K23 Sequence

The nucleic acid coding sequence of the L. pennellii cLEC73K23 gene was obtained by PCR with primers from the 5' and 3' ends of the L. esculentum cLEC73K23. The correct 5' and 3' ends of the L. pennellii gene were then obtained by 5' and 3' RACE. The full-length coding sequence of this gene and the amino acid sequence are shown in FIGS. 11A-11B (SEQ ID NO: 8 and SEQ ID NO: 9). The L. pennellii and L. esculentum cLEC73K23 cDNA sequences are 95% identical, whereas the amino acid sequences are 98% similar and 97% identical. An amino acid alignment of the L. pennellii and L. esculentum cLEC73K23 sequences and the L. esculentum cLEC75E21 sequences are shown in FIG. 12.

It should be understood that the examples and embodiments described herein are for illustrative purposes only and that various modifications or changes in light thereof will be suggested to persons skilled in the art and are to be included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 5,106,739
U.S. Pat. No. 5,625,136
U.S. Pat. No. 5,034,322

U.S. Pat. No. 5,589,610
U.S. Pat. No. 5,639,948
U.S. Pat. No. 6,462,185
U.S. Pat. No. 6,528,701
U.S. Pat. No. 6,054,574
U.S. Pat. No. 6,118,049
U.S. Pat. No. 6,340,748
U.S. Pat. No. 6,127,179
U.S. Pat. No. 5,859,328
U.S. Pat. No. 5,652,354
U.S. Pat. No. 6,455,760
U.S. Pat. No. 6,696,623
Published U.S. Patent Application No. 20040078841
Published U.S. Patent Application No. 20040067506
Published U.S. Patent Application No. 20040019934
Published U.S. Patent Application No. 20030177536
Published U.S. Patent Application No. 20030084486
Published U.S. Patent Application No. 20040123349
Aharoni, A. et al. (2000) "Identification of the SAAT gene involved in strawberry flavor biogenesis by use of DNA microarrays" *Plant Cell* 12:647-661.
Altschul, S. F. et al. (1990) "Basic Local Alignment Search Tool" *J. Mol. Biol.* 215:402-410.
Altschul, S. F. et al. (1997) "Gapped BLAST and PSI-BLAST: A New Generation of Protein Database Search Programs" *Nucl. Acids Res.* 25:3389-3402.
Baldwin, E. A. et al. (2000) "Flavor trivia and tomato aroma: Biochemistry and possible mechanisms for control of important aroma components" *Hortscience* 35:1013-1022.
Bartley, G. et al. (1994) "Molecular biology of carotenoid biosynthesis in plants" *Annual Review of Plant Physiology & Plant Molecular Biology* Jones, R. L.; Somerville, C. R.: Eds. Annual Review of Plant Physiology and Plant Molecular Biology. 45: 287-301.
Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.
Blume, B. and Grierson, D. (1997) "Expression of ACC oxidase promoter-GUS fusions in tomato and *Nicotiana plumbaginifolia* regulated by developmental and environmental stimuli" *Plant J.* 12: 731-746.
Buttery, R. et al. (1988) "Quantitative studies on origins of fresh tomato aroma volatiles" *J. Agric. Food Chem.* 36:1247-1250.
Ciardi, J. A. et al. (2000) "Response to *Xanthomonas campestris* pv. *vesicatoria* in tomato involves regulation of ethylene receptor gene expression" *Plant Physiol.* 123:81-92.
Clancy, M. and Hannah, L. C. (2002) "Splicing of the maize Sh1 first intron is essential for enhancement of gene expression, and a T-rich motif increases expression without affecting splicing," *Plant Physiol.* 130(2):918-29.
de Boer, H. A., Comstock, L. J., Vasser, M. (1983) "The tac promoter: a functional hybrid derived from the trp and lac promoters" *Proc. Natl. Acad. Sci. USA* 80(1):21-25.
Deikman, J. et al. (1992) "Organization of ripening and ethylene regulatory regions in a fruit-specific promoter from tomato (*Lycopersicon esculentum*)" *Plant Physiol.* 100: 2013-2017.
Eshed, Y. and Zamir, D. (1994) "A genomic library of *Lycopersicon pennellii* in *L. esculentum*: A tool for fine mapping of genes" *Euphytica* 79:175-179.
Fray, R. and Grierson, D. (1993) "Identification and genetic analysis of normal and mutant phytoene synthase genes of tomato by sequencing, complementation, and co-suppression" *Plant Mol. Biol.* 22:589-602.

Giovannoni, J. (2001) "Molecular Regulation of Fruit Ripening" *Ann. Rev. Plant Physiol. Plant Molec. Biol.* 52:725-749.
Giovannoni, J. et al. (2002) "A MADS-box gene necessary for fruit ripening at the tomato ripening-inhibitor (rin) locus" *Science* 296(5566):275-276.
Giovannoni, J. et al. (1999) "Analysis of gene expression and mutants influencing ethylene responses and fruit development in tomato" In *Biology and Biotechnology of the Plant Hormone Ethylene II*, (Kanellis, A. ed.) Kluwer Academic Publishers, pp. 119-127.
Giovannoni, J. et al. (1989) "Expression of a chimeric polygalacturonase gene in transgenic rin (ripening inhibitor) tomato fruit results in polyuronide degradation but not fruit softening" *Plant Cell* 1:53-63.
Good, X. et al. (1994) "Reduced ethylene synthesis by transgenic tomatoes expressing S-adenosylmethionine hydrolase." *Plant Molec. Biol.* 26:781-790.
Gray, J. E. et al. (1994) "The use of transgenic and naturally occurring mutants to understand and manipulate tomato fruit ripening" Plant, *Cell and Environment* 17:557-571.
Hamilton, A. et al. (1990) "Antisense gene that inhibits synthesis of the hormone ethylene in transgenic plants" *Nature* 346:284-287.
Hobson, G. and Grierson, D. (1993) "Tomato" In: Seymour G B, Taylor J E, Tucker G A (eds) Biochemistry of Fruit Ripening. Chapman and Hall, London pp 405-442.
Karlin S. and Altschul, S. F. (1990) "Methods for Assessing the Statistical Significance of Molecular Sequence Features by Using General Scoring Schemes" *Proc. Natl. Acad. Sci. USA* 87:2264-2268.
Karlin S. and Altschul, S. F. (1993) "Applications and Statistics for Multiple High-Scoring Segments in Molecular Sequences" *Proc. Natl. Acad. Sci. USA* 90:5873-5877.
Klee, H. J. et al. (1991) "Control of ethylene synthesis by expression of a bacterial enzyme in transgenic tomato plants" *Plant Cell* 3:1187-1193.
Kramer, M. et al. (1990) "Field evaluation of tomatoes with reduced polygalacturonase by antisense RNA" In Horticultural Biotechnology. Bennett, A. and O. Neill, S. (eds.) Alan R. Liss. pp. 347-355.
Lanahan, M. B. et al. (1994) "The Never Ripe mutation blocks ethylene perception in tomato" *Plant Cell* 6:521-530.
Larroy, C. et al. (2002) "Characterization of the *Saccharomyces cervisiae* YMR318C (ADH6) gene product as a broad specificity NADPH-dependent alcohol dehydrogenase: relevance in aldehyde reduction" *Biochem. J.* 361:163-172.
Lashbrook, C. et al. (1998) "Transgenic analysis of tomato endo-beta-1,4-glucanase gene function. Role of CEL1 in floral abscission" *Plant J.* 13:303-310.
Lelievre, J. et al. (1998) "Ethylene and fruit ripening" *Plant Physiol.* 101:727-739.
Lewin, B. (1985) *Genes II*, John Wiley & Sons, Inc., p. 96.
Lincoln, J. et al. (1987) "Regulation of gene expression by ethylene during *Lycopersicon esculentum* (tomato) fruit development" *Proc. Nat. Acad. Sci. USA*. 84:2793-2797.
Maniatis, T., E. F. Fritsch, J. Sambrook (1982) "Nuclease Bal31" *Molecular Cloning: A Laboratory Manual*, Cold Spring Harbor Laboratory, Cold Spring Harbor, N.Y.
Maunders, M. et al. (1987) "Ethylene stimulates the accumulation of ripening-related mRNAs in tomatoes" *Plant Cell Environ.* 10:177-184.
Moore, S. et al. (2002) "Use of genomics tools to isolate key ripening genes and analyse fruit maturation in tomato" *J. Exp. Bot.* 53:2023-2030.

Nakatsuka, A. et al. (1998) "Differential expression and internal feedback regulation of 1-aminocyclopropane-1-carboxylate synthase, of 1-aminocyclopropane-1-carboxylate oxidase, and ethylene receptor genes in tomato during development and ripening" *Plant Physiol.* 118:1295-1305.

Oeller, P. W. et al. (1991) "Reversible inhibition of tomato fruit senescence by antisense 1-aminocyclopropane-1-carboxylate synthase" *Science* 254:427-439.

Payton, S. et al. (1996) "Ethylene receptor expression is regulated during fruit ripening, flower senescence and abscission" *Plant Molecular Biology* 31:1227-1231.

Picton, S. et al. (1993) "Altered fruit ripening and leaf senescence in tomatoes expressing an antisense ethylene-forming enzyme transgene" *Plant J.* 3:469-481.

Rhodes, M. J. C. (1980) "The maturation and ripening of fruits" In: K V Thimann (ed) Senescence in Plants. CRC Press, Boca Raton, Fla., pp. 157-205.

Richins, R. D. et al. (1987) Sequence of the figwort mosaic virus DNA (caulimovirus group)" *Nucl. Acids Res.* 15:8451-8466.

Riley, J. and Thompson, J. (1997) "Subcellular generation and distribution of lipid-derived volatiles in the ripe tomato" *J. Plant Physiol.* 149-150:546-551.

Ronen, G. et al. (1999) "Regulation of carotenoid biosynthesis during tomato fruit development: Expression of the gene for lycopene epsilon-cyclase is down-regulated during ripening and is elevated in the mutant Delta" *Plant J.* 17: 341-351.

Rontein, D. et al. (2001) "Plants synthesize ethanolamine by direct decarboxylation of serine using a pyridoxal phosphate enzyme" *J. Biol. Chem.* 276:35523-35529.

Sambrook, J. et al. (1989) *Molecular Cloning: A Laboratory Manual*, 2nd ed. (Cold Spring Harbor, N.Y., Cold Spring Harbor Laboratory).

Schmelz, E. A. et al. (2001) "The influence of intact-plant and excised-leaf bioassay designs on volicitin- and jasmonic acid-induced sesquiterpene volatile release in *Zea mays*" *Planta* 214:171-179.

Schmelz, E. A. et al. (2003) "Qualitative relationships between induced jasmonic acid levels and volatile emission in *Zea mays* during *Spodoptera exigua* herbivory" *Planta* 216:665-673.

Schwartz, S. et al. (2001) "Characterization of a novel carotenoid cleavage dioxygenase from plants" *J. Biol. Chem.* 276:25208-25211.

Smith, C. et al. (1988) "Antisense RNA inhibition of polygalacturonase gene expression in transgenic tomatoes" *Nature* 334:724-726.

Tan, B. et al. (1997) "Genetic Control of Abscisic Acid Biosynthesis in Maize" *Proc. Nat. Acad. Sci. USA* 94:12235-12240.

Tanksley, S. et al. (1992) "High density molecular linkage maps of the tomato and potato genomes" *Genetics* 132:1141-1160.

Theologis, A. (1993) "Use of a tomato mutant constructed with reverse genetics to study fruit ripening, a complex developmental process" *Dev. Genetics* 14:282-259.

Tucker, G. A. and Brady, C. J. (1987) "Silver ions interrupt tomato fruit ripening" *J. Plant Physiol.* 127:165-169.

Vrebalov, J. et al. (2002) "A MADS-box gene necessary for fruit ripening at the tomato ripening-inhibitor (rin) locus" *Science* 296:343-346.

Wilkinson, J. Q. et al. (1997) "A dominant mutant receptor from *Arabidopsis* confers ethylene insensitivity in heterologous plants" *Nature Biotechnol.* 15: 444-447.

Wilkinson, J. et al. (1995) "An ethylene-inducible component of signal transduction encoded by Never-ripe" *Science* 270:1807-1809.

Xu, D., McElroy, D., Thornburg, R. W., Wu, R. et al. (1993) "Systemic induction of a potato pint promoter by wounding, methyl jasmonate, and abscisic acid in transgenic rice plants" *Plant Molecular Biology* 22:573-588.

Yang, S. F. (1985) "Biosynthesis and action of ethylene" *HortScience* 20:41-45.

Yang, T. T. et al. (1996) "Optimized Codon Usage and Chromophore Mutations Provide Enhanced Sensitivity with the Green Fluorescent Protein" *Nucleic Acid Research* 24(22): 4592-4593.

Yen, H. et al. (1997) "The tomato high pigment (hp) locus maps to chromosome 2 and influences plastome copy number and fruit quality" *Theoretical and Applied Genetics* 95:1069-1079.

Yen, H. et al. (1995) "The tomato Never-ripe locus regulates ethylene-inducible gene expression and is linked to a homologue of the *Arabidopsis* ETR1 gene" *Plant Physiology* 107:1343-1353.

---

We claim:

1. A polynucleotide expression construct comprising:
a polynucleotide sequence encoding a plant aromatic amino acid decarboxylase, or an enzymatically active fragment thereof, wherein said decarboxylase comprises the amino acid sequence shown in SEQ ID NO: 5, SEQ ID NO: 7, SEQ ID NO: 9, or SEQ ID NO: 13, or an enzymatically active fragment thereof, or said decarboxylase has 70% or greater sequence identity with the amino acid sequence shown in SEQ ID NO: 5, SEQ ID NO: 7, SEQ ID NO: 9, or SEQ ID NO: 13, and exhibits aromatic amino acid decarboxylase enzymatic activity, and wherein said expression construct comprises a heterologous promoter that is functional in a plant cell.

2. A cell transformed with:
a polynucleotide encoding a plant aromatic amino acid decarboxylase, or an enzymatically active fragment thereof, wherein said decarboxylase comprises the amino acid sequence shown in SEQ ID NO: 5, SEQ ID NO: 7, SEQ ID NO: 9, or SEQ ID NO: 13, or an enzymatically active fragment thereof, or said decarboxylase has 70% or greater sequence identity with the amino acid sequence shown in SEQ ID NO: 5, SEQ ID NO: 7, SEQ ID NO: 9, or SEQ ID NO: 13, and exhibits aromatic amino acid decarboxylase enzymatic activity.

3. The cell according to claim 2, wherein said polynucleotide is provided in a polynucleotide expression construct.

4. A plant, plant tissue, or plant cell transformed with or bred to contain:
a polynucleotide encoding a plant aromatic amino acid decarboxylase, or an enzymatically active fragment thereof, wherein said decarboxylase comprises the amino acid sequence shown in SEQ ID NO: 5, SEQ ID NO: 7, SEQ ID NO: 9, or SEQ ID NO: 13, or an enzymatically active fragment thereof, or said decarboxylase has 70% or greater sequence identity with the amino acid sequence shown in SEQ ID NO: 5, SEQ ID NO: 7, SEQ ID NO: 9, or SEQ ID NO: 13, and exhibits aromatic amino acid decarboxylase enzymatic activity.

5. A method for providing a plant with increased flavor or fragrance, said method comprising incorporating in said plant:
a polynucleotide encoding a plant aromatic amino acid decarboxylase, or an enzymatically active fragment thereof, wherein said decarboxylase comprises the amino acid sequence shown in SEQ ID NO: 5, SEQ ID NO: 7, SEQ ID NO: 9, or SEQ ID NO: 13, or an enzymatically active fragment thereof, or said decarboxylase has 70% or greater sequence identity with the amino acid sequence shown in SEQ ID NO: 5, SEQ ID NO: 7, SEQ ID NO: 9, or SEQ ID NO: 13, and exhibits aromatic amino acid decarboxylase enzymatic activity;
and expressing the polypeptide encoded by said polynucleotide.

6. A transgenic plant, plant tissue, or plant cell, wherein said plant, plant tissue or plant cell comprises incorporated in the genome of said plant, plant tissue, or plant cell:
- a polynucleotide encoding a plant aromatic amino acid decarboxylase, or an enzymatically active fragment thereof, wherein said decarboxylase comprises the amino acid sequence shown in SEQ ID NO: 5, SEQ ID NO: 7, SEQ ID NO: 9, or SEQ ID NO: 13, or an enzymatically active fragment thereof, or said decarboxylase has 70% or greater sequence identity with the amino acid sequence shown in SEQ ID NO: 5, SEQ ID NO: 7, SEQ ID NO: 9, or SEQ ID NO: 13, and exhibits aromatic amino acid decarboxylase enzymatic activity.

7. The expression construct according to claim 1, wherein said decarboxylase comprises the amino acid sequence shown in SEQ ID NO: 5, or an enzymatically active fragment thereof.

8. The expression construct according to claim 1, wherein said decarboxylase comprises the amino acid sequence shown in SEQ ID NO: 7, or an enzymatically active fragment thereof.

9. The expression construct according to claim 1, wherein said decarboxylase comprises the amino acid sequence shown in SEQ ID NO: 9, or an enzymatically active fragment thereof.

10. The expression construct according to claim 1, wherein said decarboxylase comprises the amino acid sequence shown in SEQ ID NO: 13, or an enzymatically active fragment thereof.

11. The expression construct according to claim 1, wherein said polynucleotide comprises the nucleotide sequence shown in SEQ ID NO: 4, SEQ ID NO: 6, SEQ ID NO: 8, or SEQ ID NO: 12, or said polynucleotide comprises a nucleotide sequence that hybridizes under stringent hybridization conditions with the nucleotide sequence shown in SEQ ID NO: 4, SEQ ID NO: 6, SEQ ID NO: 8, or SEQ ID NO: 12, or the complement thereof, and said polynucleotide encodes a polypeptide having aromatic amino acid decarboxylase enzymatic activity.

12. The expression construct according to claim 1, wherein said polynucleotide comprises the nucleotide sequence shown in SEQ ID NO: 4.

13. The expression construct according to claim 1, wherein said polynucleotide comprises the nucleotide sequence shown in SEQ ID NO: 6.

14. The expression construct according to claim 1, wherein said polynucleotide comprises the nucleotide sequence shown in SEQ ID NO: 8.

15. The expression construct according to claim 1, wherein said polynucleotide comprises the nucleotide sequence shown in SEQ ID NO: 12.

16. The expression construct according to claim 1, wherein said expression construct further comprises one or more regulatory elements operably linked to said polynucleotide.

17. The expression construct according to claim 16, wherein said regulatory element is one or more of a promoter, transcription termination sequence, translation termination sequence, enhancer, or a polyadenylation sequence.

18. The expression construct according to claim 1, wherein said promoter is a seed-specific promoter, a tissue-specific promoter, a constitutive promoter, a developmentally-regulated promoter, or an inducible promoter.

19. The expression construct according to claim 18, wherein said constitutive promoter is a CaMV promoter, ubiquitin promoter, actin promoter, or NOS promoter.

20. The expression construct according to claim 18, wherein said tissue-specific promoter is a fruit-specific promoter.

21. The expression construct according to claim 20, wherein said fruit-specific promoter is an E8 promoter, a hybrid E4/E8 promoter, an LeExp-1 promoter, or a polygalacturonase-β subunit promoter.

22. The expression construct according to claim 18, wherein said tissue-specific promoter is a flower organ-specific promoter.

23. The plant, plant tissue, or plant cell according to claim 4, wherein said polynucleotide is provided in a polynucleotide expression construct.

24. The plant, plant tissue, or plant cell according to claim 4, wherein said decarboxylase comprises the amino acid sequence shown in SEQ ID NO: 5, or an enzymatically active fragment thereof.

25. The plant, plant tissue, or plant cell according to claim 4, wherein said decarboxylase comprises the amino acid sequence shown in SEQ ID NO: 7, or an enzymatically active fragment thereof.

26. The plant, plant tissue, or plant cell according to claim 4, wherein said decarboxylase comprises the amino acid sequence shown in SEQ ID NO: 9, or an enzymatically active fragment thereof.

27. The plant, plant tissue, or plant cell according to claim 4, wherein said decarboxylase comprises the amino acid sequence shown in SEQ ID NO: 13, or an enzymatically active fragment thereof.

28. The plant, plant tissue, or plant cell according to claim 4, wherein said plant is a tomato, pea, alfalfa, melon, chickpea, chicory, clover, kale, lentil, soybean, tobacco, potato, sweet potato, radish, cabbage, rape, grape, sunflower, lettuce, cucumber, watermelon, apple, citrus, orange, lemon, tangerine, grapefruit, lime, pear, plum, peach, fig, currant, muskmelon, squash, cherry, sugar beet, tea, strawberry, blackberry, blueberry, raspberry, loganberry, rose, chrysanthemum, sweet pepper, eggplant, cotton, rice, wheat, barley, oats, sorghum, maize, sugarcane, pineapple, onion, bananas, coconut, lilies, grasses, millet, rose, petunia, carnation, orchid, tulip, or gardenia.

29. The method according to claim 5, wherein said polynucleotide is provided in a polynucleotide expression construct.

30. The method according to claim 5, wherein said decarboxylase comprises the amino acid sequence shown in SEQ ID NO: 5, or an enzymatically active fragment thereof.

31. The method according to claim 5, wherein said decarboxylase comprises the amino acid sequence shown in SEQ ID NO: 7, or an enzymatically active fragment thereof.

32. The method according to claim 5, wherein said decarboxylase comprises the amino acid sequence shown in SEQ ID NO: 9, or an enzymatically active fragment thereof.

33. The method according to claim 5, wherein said decarboxylase comprises the amino acid sequence shown in SEQ ID NO: 13, or an enzymatically active fragment thereof.

34. The method according to claim 5, wherein said plant is a tomato, pea, alfalfa, melon, chickpea, chicory, clover, kale, lentil, soybean, tobacco, potato, sweet potato, radish, cabbage, rape, grape, sunflower, lettuce, cucumber, watermelon, apple, citrus, orange, lemon, tangerine, grapefruit, lime, pear, plum, peach, fig, currant, muskmelon, squash, cherry, sugar beet, tea, strawberry, blackberry, blueberry, raspberry, loganberry, rose, chrysanthemum, sweet pepper, eggplant, cotton, rice, wheat, barley, oats, sorghum, maize, sugarcane, pineapple, onion, bananas, coconut, lilies, grasses, millet, rose, petunia, carnation, orchid, tulip, or gardenia.

35. The transgenic plant, plant tissue, or plant cell according to claim 6, wherein said polynucleotide is provided in a polynucleotide expression construct.

36. The transgenic plant, plant tissue, or plant cell according to claim 6, wherein said decarboxylase comprises the amino acid sequence shown in SEQ ID NO: 5, or an enzymatically active fragment thereof.

37. The transgenic plant, plant tissue, or plant cell according to claim 6, wherein said decarboxylase comprises the amino acid sequence shown in SEQ ID NO: 7, or an enzymatically active fragment thereof.

38. The transgenic plant, plant tissue, or plant cell according to claim 6, wherein said decarboxylase comprises the amino acid sequence shown in SEQ ID NO: 9, or an enzymatically active fragment thereof.

39. The transgenic plant, plant tissue, or plant cell according to claim 6, wherein said decarboxylase comprises the amino acid sequence shown in SEQ ID NO: 13, or an enzymatically active fragment thereof.

40. The transgenic plant, plant tissue, or plant cell according to claim 6, wherein said plant is a tomato, pea, alfalfa, melon, chickpea, chicory, clover, kale, lentil, soybean, tobacco, potato, sweet potato, radish, cabbage, rape, grape, sunflower, lettuce, cucumber, watermelon, apple, citrus, orange, lemon, tangerine, grapefruit, lime, pear, plum, peach, fig, currant, muskmelon, squash, cherry, sugar beet, tea, strawberry, blackberry, blueberry, raspberry, loganberry, rose, chrysanthemum, sweet pepper, eggplant, cotton, rice, wheat, barley, oats, sorghum, maize, sugarcane, pineapple, onion, bananas, coconut, lilies, grasses, millet, rose, petunia, carnation, orchid, tulip, or gardenia.

41. The expression construct according to claim 1, wherein said polynucleotide is complementary deoxyribonucleic acid (cDNA).

* * * * *

UNITED STATES PATENT AND TRADEMARK OFFICE
CERTIFICATE OF CORRECTION

PATENT NO. : 8,709,811 B2  
APPLICATION NO. : 10/574124  
DATED : April 29, 2014  
INVENTOR(S) : Harry J. Klee and Denise Tieman Page 1 of 1

It is certified that error appears in the above-identified patent and that said Letters Patent is hereby corrected as shown below:

In the Specification

Column 10,
Line 65, "from a (1-phaseolin)" should read --from a β-phaseolin--

Column 26,
Line 23, "Clardi" should read --Ciardi--

Column 28,
Line 56, "Kin's" should read --Km's--

Column 34,
Line 27, "pint promoter" should read --pin2 promoter--

Signed and Sealed this
Thirtieth Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,709,811 B2 Page 1 of 1
APPLICATION NO. : 10/574124
DATED : April 29, 2014
INVENTOR(S) : Klee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2160 days.

Signed and Sealed this

Twenty-ninth Day of September, 2015

Michelle K. Lee
*Director of the United States Patent and Trademark Office*

SEQUENCE LISTING

```
<160> NUMBER OF SEQ ID NOS: 13

<210> SEQ ID NO 1
<211> LENGTH: 1367
<212> TYPE: DNA
<213> ORGANISM: Lycopersicon esculentum

<400> SEQUENCE: 1
gcccttctaa tacgactcac tatagggcaa gcagtggtaa caacgcagag tacgcggggg      60
aaggataatc tctcaaatta ctttcttttt ttttcctatc aattctttat accaaaataa     120
tattattgtt tttttctcct ctgtttctgc ttcgtatttt tgctgagaga aatgagtgtg     180
acagcgaaaa cagtgtgtgt aacaggagct tcaggttaca tagcttcatg gctagtcaaa     240
ttcttgctac atagtggtta caatgtgaag gcttctgttc gtgatccaaa tgatcccaag     300
aaaacgcagc acttgctttc tcttggtggg gccaaggaga ggcttcactt gttcaaagca     360
aacctattag aagaaggttc atttgatgct gtagttgatg gatgtgaagg tgtattccat     420
```

```
acagcgtctc cttttactacta ctctgttaca gacccacagg ctgaattact tgatcctgct    480
gttaagggaa cactcaatct tctcgggtca tgtgccaaag caccatcagt aaaacgagtt    540
gttttaacgt cttccatagc tgcagttgct tacagtggtc agcctcggac acctgaggtt    600
gtggttgatg agagctggtg gaccagtcca gactactgca agaaaaaca gctctggtat    660 gtcctctcaa agacattggc tgaggatgct gcgtggaagt ttgtgaagga aaaggcatt    720 gatatggttg tagtaaaccc tgctatggtt attggtcctc tgttacagcc tacacttaat    780
accagttctg ctgcagtctt gagcttggta aatggtgctg agacataccc aaattcctct    840
tttgggtggg ttaacgtgaa agatgttgca atgcacata ttcttgcatt tgagaaccct    900
tcagctaatg ggagatactt aatggttgag agggttgcac actattctga tatattgaag    960
atattgcgtg acctttatcc tactatgcaa cttccagaaa agtgtgctga tgacaaccca   1020
ttgatgcaaa attatcaagt atcaaaggag aaggcaaaaa gcttgggtat tgagtttact   1080
acccttgaag aaagcatcaa agaaactgtt gaaagtttga aggaaaagaa gttttttgga   1140
ggttcatctt ctatgtaaaa ggcttctcaa agcttttatg gttttgttga acaatactac   1200
ccaccccacc ctaccctaca cacttttttt ttttacttct tttagctaat tatagaatca   1260
agaagtcgaa tggtatatcc gttaataaat ttcgatcaga tgaggttgaa atttgttcta   1320
tatctagaga ttttacagac ctggtttgat agaaaaaaaa aaaaaaa                    1367
```

<210> SEQ ID NO 2
<211> LENGTH: 328
<212> TYPE: PRT
<213> ORGANISM: Lycopersicon esculentum

<400> SEQUENCE: 2

```
Met Ser Val Thr Ala Lys Thr Val Cys Val Thr Gly Ala Ser Gly Tyr
1               5                   10                  15

Ile Ala Ser Trp Leu Val Lys Phe Leu Leu His Ser Gly Tyr Asn Val
            20                  25                  30

Lys Ala Ser Val Arg Asp Pro Asn Asp Pro Lys Lys Thr Gln His Leu
        35                  40                  45

Leu Ser Leu Gly Gly Ala Lys Glu Arg Leu His Leu Phe Lys Ala Asn
    50                  55                  60

Leu Leu Glu Glu Gly Ser Phe Asp Ala Val Val Asp Gly Cys Glu Gly
65                  70                  75                  80

Val Phe His Thr Ala Ser Pro Phe Tyr Tyr Ser Val Thr Asp Pro Gln
                85                  90                  95

Ala Glu Leu Leu Asp Pro Ala Val Lys Gly Thr Leu Asn Leu Leu Gly
            100                 105                 110

Ser Cys Ala Lys Ala Pro Ser Val Lys Arg Val Val Leu Thr Ser Ser
        115                 120                 125

Ile Ala Ala Val Ala Tyr Ser Gly Gln Pro Arg Thr Pro Glu Val Val
    130                 135                 140

Val Asp Glu Ser Trp Trp Thr Ser Pro Asp Tyr Cys Lys Glu Lys Gln
145                 150                 155                 160

Leu Trp Tyr Val Leu Ser Lys Thr Leu Ala Glu Asp Ala Ala Trp Lys
                165                 170                 175

Phe Val Lys Glu Lys Gly Ile Asp Met Val Val Asn Pro Ala Met
            180                 185                 190

Val Ile Gly Pro Leu Leu Gln Pro Thr Leu Asn Thr Ser Ser Ala Ala
        195                 200                 205
```

```
Val Leu Ser Leu Val Asn Gly Ala Glu Thr Tyr Pro Asn Ser Ser Phe
        210                 215                 220

Gly Trp Val Asn Val Lys Asp Val Ala Asn Ala His Ile Leu Ala Phe
225                 230                 235                 240

Glu Asn Pro Ser Ala Asn Gly Arg Tyr Leu Met Val Glu Arg Val Ala
                245                 250                 255

His Tyr Ser Asp Ile Leu Lys Ile Leu Arg Asp Leu Tyr Pro Thr Met
            260                 265                 270

Gln Leu Pro Glu Lys Cys Ala Asp Asp Asn Pro Leu Met Gln Asn Tyr
        275                 280                 285

Gln Val Ser Lys Glu Lys Ala Lys Ser Leu Gly Ile Glu Phe Thr Thr
        290                 295                 300

Leu Glu Glu Ser Ile Lys Glu Thr Val Glu Ser Leu Lys Glu Lys Lys
305                 310                 315                 320

Phe Phe Gly Gly Ser Ser Ser Met
                325

<210> SEQ ID NO 3
<211> LENGTH: 35
<212> TYPE: DNA
<213> ORGANISM: Artificial sequence
<220> FEATURE:
<223> OTHER INFORMATION: PCR primer

<400> SEQUENCE: 3
tccttggccc caccaagaga aagcaagtgc tgcgt                                35

<210> SEQ ID NO 4
<211> LENGTH: 1398
<212> TYPE: DNA
<213> ORGANISM: Lycopersicon esculentum

<400> SEQUENCE: 4
atgggaagtt tatcatttga aaggattttt gagccatcag caattactcc aagaggatta     60
gcaccacctg gattaattgt aaatggtgat tttggtgaaa tgatgagact taaggtgtca    120
tcaacaccaa caacaccaag aaaaaacttg aatctttcag tgacggagcc aggaaaaaat    180
gatggaccta gtttggattg tacattgatg aatttatattg atacactcac ccaacgtatc    240
aactatcata tcggttatcc agttaacata tgttatgagc actatgctaa tttagcccca    300
cttttacaat ttcatttaaa taattgtggt gatccatttc ttcaaaatac tgtggatttt    360
cattcaaagg attttgaagt ggctgtttta aattggtttg ctgatttatg ggaaattgaa    420
agagatcaat attggggcta tgtaacaaat ggtggtactg aaggaaattt acatggcatt    480
ttggttggga gagaattgtt tccagatgga attttatatg catcaaaaga ctctcattac    540
tcagtggcta aggcagcaat gatgtataga atggattttg aaaatattaa cgcatcaata    600
aatggagaaa tcgattattc tgatttgaaa gttaaattac ttcaaaacaa gggaaaacca    660
gcgataatta atgttacaat tggcactact tttaaaggag ctgttgatga tcttgatgtt    720
attcttcaaa tacttgaaga gtgtggttac acacgagatc aatttttatat tcattgtgat    780 gcagcactaa atggacttat tattccttttt attaaaaata tgattacttt caagaagcca    840
attggaagtg tgacaatttc tggtcacaag ttttttggat gtccaatgcc ttgtggagtt    900
caaataacaa ggaaaagtta cattaataac ctttcgagaa gagtcgaata tattgcttct    960
gtggatgcta caatttctgg aagtcgaaat ggtttgactc cgatcttctt atggtacagt   1020
ataagtgcta aaggtcaaat tggttttcag aaagacgtta agagatgttt tgacaatgct   1080
```

```
aagtacttga aagaccgtct tcagcaagca ggaatcagcg tcatgctgaa tgagcttagc    1140
atcatagttg tcctcgagag gcctcgtgac catgaattcg ttcgtcgttg caattatct    1200 tgtgtgagag atatggcaca tgttattgtt atgccaggca taactagaga aactcttgat    1260
ggttttatta atgatttgct tcaacaaagg aaaaaatggt atcaagatgg aagaattagc    1320
cctccttgtg ttgcaaatga tattggtgct caaaattgtg cttgctctta tcataaaatt    1380
gattacatta ttgcttag                                                 1398
```

<210> SEQ ID NO 5
<211> LENGTH: 465
<212> TYPE: PRT
<213> ORGANISM: Lycopersicon esculentum

<400> SEQUENCE: 5

```
Met Gly Ser Leu Ser Phe Glu Lys Asp Phe Glu Pro Ser Ala Ile Thr
1               5                   10                  15

Pro Arg Gly Leu Ala Pro Pro Gly Leu Ile Val Asn Gly Asp Phe Gly
            20                  25                  30

Glu Met Met Arg Leu Lys Val Ser Ser Thr Pro Thr Thr Pro Arg Lys
        35                  40                  45

Asn Leu Asn Leu Ser Val Thr Glu Pro Gly Lys Asn Asp Gly Pro Ser
    50                  55                  60

Leu Asp Cys Thr Leu Met Asn Tyr Ile Asp Thr Leu Gln Arg Ile
65                  70                  75                  80

Asn Tyr His Ile Gly Tyr Pro Val Asn Ile Cys Tyr Glu His Tyr Ala
                85                  90                  95

Asn Leu Ala Pro Leu Leu Gln Phe His Leu Asn Asn Cys Gly Asp Pro
            100                 105                 110

Phe Leu Gln Asn Thr Val Asp Phe His Ser Lys Asp Phe Glu Val Ala
        115                 120                 125

Val Leu Asn Trp Phe Ala Asp Leu Trp Glu Ile Glu Arg Asp Gln Tyr
    130                 135                 140

Trp Gly Tyr Val Thr Asn Gly Gly Thr Glu Gly Asn Leu His Gly Ile
145                 150                 155                 160

Leu Val Gly Arg Glu Leu Phe Pro Asp Gly Ile Leu Tyr Ala Ser Lys
                165                 170                 175

Asp Ser His Tyr Ser Val Ala Lys Ala Ala Met Met Tyr Arg Met Asp
            180                 185                 190

Phe Glu Asn Ile Asn Ala Ser Ile Asn Gly Glu Ile Asp Tyr Ser Asp
        195                 200                 205

Leu Lys Val Lys Leu Leu Gln Asn Lys Gly Lys Pro Ala Ile Ile Asn
    210                 215                 220

Val Thr Ile Gly Thr Thr Phe Lys Gly Ala Val Asp Asp Leu Asp Val
225                 230                 235                 240

Ile Leu Gln Ile Leu Glu Glu Cys Gly Tyr Thr Arg Asp Gln Phe Tyr
                245                 250                 255

Ile His Cys Asp Ala Ala Leu Asn Gly Leu Ile Ile Pro Phe Ile Lys
            260                 265                 270

Asn Met Ile Thr Phe Lys Lys Pro Ile Gly Ser Val Thr Ile Ser Gly
        275                 280                 285

His Lys Phe Leu Gly Cys Pro Met Pro Cys Gly Val Gln Ile Thr Arg
    290                 295                 300

Lys Ser Tyr Ile Asn Asn Leu Ser Arg Arg Val Glu Tyr Ile Ala Ser
305                 310                 315                 320
```

```
Val Asp Ala Thr Ile Ser Gly Ser Arg Asn Gly Leu Thr Pro Ile Phe
            325                 330                 335

Leu Trp Tyr Ser Ile Ser Ala Lys Gly Gln Ile Gly Phe Gln Lys Asp
            340                 345                 350

Val Lys Arg Cys Phe Asp Asn Ala Lys Tyr Leu Lys Asp Arg Leu Gln
            355                 360                 365

Gln Ala Gly Ile Ser Val Met Leu Asn Glu Leu Ser Ile Ile Val Val
            370                 375                 380

Leu Glu Arg Pro Arg Asp His Glu Phe Val Arg Arg Trp Gln Leu Ser
385                 390                 395                 400

Cys Val Arg Asp Met Ala His Val Ile Val Met Pro Gly Ile Thr Arg
            405                 410                 415

Glu Thr Leu Asp Gly Phe Ile Asn Asp Leu Leu Gln Gln Arg Lys Lys
            420                 425                 430

Trp Tyr Gln Asp Gly Arg Ile Ser Pro Pro Cys Val Ala Asn Asp Ile
            435                 440                 445

Gly Ala Gln Asn Cys Ala Cys Ser Tyr His Lys Ile Asp Tyr Ile Ile
            450                 455                 460

Ala
465

<210> SEQ ID NO 6
<211> LENGTH: 1416
<212> TYPE: DNA
<213> ORGANISM: Lycopersicon esculentum

<400> SEQUENCE: 6
atgggtagtc tctcacttga aatggatttt gagccatcac ccatgacacc cagaagttta      60
gcagcgatga cacctagaag tttagcgcga cgacgattgt ttccgaacgt ggacaacaag     120
aaacagaaaa tggcacaacc aggtgcagga ccaaggaaga acttggaact tgaggtcatg     180
gagcctgcat tgaagaatga tggtccttct ttggacacta tcttggttaa ttatttggac     240
acacttacac aacgagtcaa ttatcattta ggttatccag tcaacatatg ttatgatcac     300
tatgcaacgc tagcaccact tttgcagttt cacctaaaca attgtggtga tccttttccta    360 caaaatactg tcgatttcca ttctaaagac tttgaagtgg ctgttttgaa ttggtttgca     420
aaactttggg aaattgaaaa ggatcaatat tggggatatg ttaccaatgg tggcaccgaa     480
ggcaatctcc atggtatttt gttagggaga gagctacttc ctgaaggaat attatatgca     540
tcaaaagact ctcattactc agtattcaaa gctgcaagaa tgtatagaat ggattcagaa     600
acaatcaaca catcagtaaa tggagagatg gattattcag atttaagagc aaagttactt     660
caaaataagg ataaaccagc tattataaat gtcacaattg aactacatt caaaggagca      720 atcgatgacc tggatgttat tcttgaaata ctcaaagaat gtggctattc acaagatcga     780
ttttacattc actgtgatgc agcactatgt ggtcttatga cccctttat aaacaatatg     840 attagtttca gaagccaat tggaagtgtc acaattctg acacaagtt tttgggatgt       900 ccaatgcctt gtggtgtcca ataacaaga aaaagctaca tcaataatct ctcaacaaat     960
gtggaataca ttgcttctgt ggatgccact atttctggta gccgtaacgg tttaactcca    1020
attttcttat ggtatagctt gagcgcaaaa ggtcaagttg acttcaaaa ggatgttaaa    1080 agatgtctcg acaatgccaa atatttgaaa gatcgtcttc aacaagcagg gataagtgtc   1140
atgctgaatg agctaagcat catagttgta cttgaaaggc ctcgtgacca tgaatttgtg   1200
cgtcgttggc aactctcatg cgtcaaggat atggcacatg ttattgtgat gccaggaatc   1260
```

-continued

```
acacgagaaa tgcttgacaa cttcatgagt gaattagtgc aacaaagaaa agtatggtat    1320
caaaatggaa agactgatcc tccttgtgtt ggagaggata ttggtgctca aaattgtgca    1380
tgctcttatc ataagattga ctacatctgt ccttag                              1416
```

<210> SEQ ID NO 7
<211> LENGTH: 471
<212> TYPE: PRT
<213> ORGANISM: Lycopersicon esculentum

<400> SEQUENCE: 7

```
Met Gly Ser Leu Ser Leu Glu Met Asp Phe Glu Pro Ser Pro Met Thr
1               5                   10                  15

Pro Arg Ser Leu Ala Ala Met Thr Pro Arg Ser Leu Ala Arg Arg Arg
            20                  25                  30

Leu Phe Pro Asn Val Asp Asn Lys Gln Lys Met Ala Gln Pro Gly
        35                  40                  45

Ala Gly Pro Arg Lys Asn Leu Glu Leu Glu Val Met Glu Pro Ala Leu
    50                  55                  60

Lys Asn Asp Gly Pro Ser Leu Asp Thr Ile Leu Val Asn Tyr Leu Asp
65                  70                  75                  80

Thr Leu Thr Gln Arg Val Asn Tyr His Leu Gly Tyr Pro Val Asn Ile
                85                  90                  95

Cys Tyr Asp His Tyr Ala Thr Leu Ala Pro Leu Leu Gln Phe His Leu
            100                 105                 110

Asn Asn Cys Gly Asp Pro Phe Leu Gln Asn Thr Val Asp Phe His Ser
        115                 120                 125

Lys Asp Phe Glu Val Ala Val Leu Asn Trp Phe Ala Lys Leu Trp Glu
130                 135                 140

Ile Glu Lys Asp Gln Tyr Trp Gly Tyr Val Thr Asn Gly Gly Thr Glu
145                 150                 155                 160

Gly Asn Leu His Gly Ile Leu Leu Gly Arg Glu Leu Leu Pro Glu Gly
                165                 170                 175

Ile Leu Tyr Ala Ser Lys Asp Ser His Tyr Ser Val Phe Lys Ala Ala
            180                 185                 190

Arg Met Tyr Arg Met Asp Ser Glu Thr Ile Asn Thr Ser Val Asn Gly
        195                 200                 205

Glu Met Asp Tyr Ser Asp Leu Arg Ala Lys Leu Leu Gln Asn Lys Asp
    210                 215                 220

Lys Pro Ala Ile Ile Asn Val Thr Ile Gly Thr Thr Phe Lys Gly Ala
225                 230                 235                 240

Ile Asp Asp Leu Asp Val Ile Leu Glu Ile Leu Lys Glu Cys Gly Tyr
                245                 250                 255

Ser Gln Asp Arg Phe Tyr Ile His Cys Asp Ala Ala Leu Cys Gly Leu
            260                 265                 270

Met Thr Pro Phe Ile Asn Asn Met Ile Ser Phe Lys Lys Pro Ile Gly
        275                 280                 285

Ser Val Thr Ile Ser Gly His Lys Phe Leu Gly Cys Pro Met Pro Cys
    290                 295                 300

Gly Val Gln Ile Thr Arg Lys Ser Tyr Ile Asn Asn Leu Ser Thr Asn
305                 310                 315                 320

Val Glu Tyr Ile Ala Ser Val Asp Ala Thr Ile Ser Gly Ser Arg Asn
                325                 330                 335

Gly Leu Thr Pro Ile Phe Leu Trp Tyr Ser Leu Ser Ala Lys Gly Gln
            340                 345                 350
```

```
Val Gly Leu Gln Lys Asp Val Lys Arg Cys Leu Asp Asn Ala Lys Tyr
            355                 360                 365
Leu Lys Asp Arg Leu Gln Gln Ala Gly Ile Ser Val Met Leu Asn Glu
        370                 375                 380
Leu Ser Ile Ile Val Leu Glu Arg Pro Arg Asp His Glu Phe Val
385                 390                 395                 400
Arg Arg Trp Gln Leu Ser Cys Val Lys Asp Met Ala His Val Ile Val
                405                 410                 415
Met Pro Gly Ile Thr Arg Glu Met Leu Asp Asn Phe Met Ser Glu Leu
                420                 425                 430
Val Gln Gln Arg Lys Val Trp Tyr Gln Asn Gly Lys Thr Asp Pro Pro
                435                 440                 445
Cys Val Gly Glu Asp Ile Gly Ala Gln Asn Cys Ala Cys Ser Tyr His
            450                 455                 460
Lys Ile Asp Tyr Ile Cys Pro
465                 470

<210> SEQ ID NO 8
<211> LENGTH: 1416
<212> TYPE: DNA
<213> ORGANISM: Lycopersicon pennellii

<400> SEQUENCE: 8
atgggtagtc tctcacttga atggatttt gagccatcac ctatgacacc cagaagttta      60
gcagcgatga cacctagaag tttagcgcgg cgaagattgt tcccaatgt ggacaacaaa    120 aaacaaaagg tgcaacaatc aggtgcaggg ccaaggaaga acttacaact tgaagtcatg    180
gaacctgcat tgaacaatgc tggtccctct ttggacacta tattggtcaa ttatttagac    240
acacttacac aacgagtcaa ttatcattta ggttatccag tcaacatttg ttatgatcac    300
tatgcaactt tagcaccact tttacagttt cacctaaaca attgtggtga tcctttccta    360
caaaacactg tcgatttcca ttctaaagac tttgaagtgg ctgttttgaa ttggtttgca    420
aaactatggg aaattgaaaa ggatcaatac tggggatatg ttaccaatgg tggcaccgaa    480
ggcaatctcc atggtatttt gttagggaga gagctacttc ctgatggaat attatatgcg    540
tcaaaagact ctcactattc ggtcttcaaa gctgcaagaa tgtatagaat ggattcagaa    600
acaatcaaca catcagtaaa cggagagatg gattattcag atttaagagc aaagttactt    660
caaaataagg ataaaccagc tattataaat gtcacaattg aactacgtt caaaggagca    720 atcgatgacc tggatgttat tcttgaaaca ctcaaagaat gtggctattc gcaagatagg    780
ttttacatcc actgtgatgc tgcactatgt ggtcttatga ccccttttat aaacaatatg    840
attagtttca agaagccaat tggaagtgtc acaatttctg acacaagtt tttgggatgt    900 ccaatgcctt gtggtgtcca aattacaaga aagagttaca tcaataatct ctcaacaaat    960
gtggaataca ttgcttctgt cgatgccact atttctggca gccgtaacgg tttaactcca   1020
attttcttgt ggtatagctt gagcgcaaaa ggtcaagttg acttcaaaa ggatgttaaa   1080 agatgtctcg acaatgccaa atatttgaaa gatcgtcttc aaaaagcagg aataagtgtc   1140
atgttaaatg agcttagcat catagttgta cttgaaaggc ctcgtgacca tgaatttgtc   1200
cgtcgttggc aactctcatg cgtcaaggat atggcacatg ttattgtaat gccaggcatc   1260
acacgagaaa tgcttgacaa tttcacgagt gaattagtgc aacaaagaaa gtatggtat   1320 caaaatggac agaccaatcc tccttgtgtt ggagaggata ttggtgctca aaattgtgca   1380
tgctcttatc ataagattga ctacatctgt ccttag                              1416
```

<210> SEQ ID NO 9
<211> LENGTH: 471
<212> TYPE: PRT
<213> ORGANISM: Lycopersicon pennellii

<400> SEQUENCE: 9

```
Met Gly Ser Leu Ser Leu Glu Met Asp Phe Glu Pro Ser Pro Met Thr
 1               5                  10                  15

Pro Arg Ser Leu Ala Ala Met Thr Pro Arg Ser Leu Ala Arg Arg Arg
             20                  25                  30

Leu Phe Pro Asn Val Asp Asn Lys Lys Gln Lys Val Gln Gln Ser Gly
         35                  40                  45

Ala Gly Pro Arg Lys Asn Leu Gln Leu Glu Val Met Glu Pro Ala Leu
     50                  55                  60

Asn Asn Ala Gly Pro Ser Leu Asp Thr Ile Leu Val Asn Tyr Leu Asp
 65                  70                  75                  80

Thr Leu Thr Gln Arg Val Asn Tyr His Leu Gly Tyr Pro Val Asn Ile
                 85                  90                  95

Cys Tyr Asp His Tyr Ala Thr Leu Ala Pro Leu Leu Gln Phe His Leu
            100                 105                 110

Asn Asn Cys Gly Asp Pro Phe Leu Gln Asn Thr Val Asp Phe His Ser
        115                 120                 125

Lys Asp Phe Glu Val Ala Val Leu Asn Trp Phe Ala Lys Leu Trp Glu
    130                 135                 140

Ile Glu Lys Asp Gln Tyr Trp Gly Tyr Val Thr Asn Gly Gly Thr Glu
145                 150                 155                 160

Gly Asn Leu His Gly Ile Leu Leu Gly Arg Glu Leu Leu Pro Asp Gly
                165                 170                 175

Ile Leu Tyr Ala Ser Lys Asp Ser His Tyr Ser Val Phe Lys Ala Ala
            180                 185                 190

Arg Met Tyr Arg Met Asp Ser Glu Thr Ile Asn Thr Ser Val Asn Gly
        195                 200                 205

Glu Met Asp Tyr Ser Asp Leu Arg Ala Lys Leu Leu Gln Asn Lys Asp
    210                 215                 220

Lys Pro Ala Ile Ile Asn Val Thr Ile Gly Thr Thr Phe Lys Gly Ala
225                 230                 235                 240

Ile Asp Asp Leu Asp Val Ile Leu Glu Thr Leu Lys Glu Cys Gly Tyr
                245                 250                 255

Ser Gln Asp Arg Phe Tyr Ile His Cys Asp Ala Ala Leu Cys Gly Leu
            260                 265                 270

Met Thr Pro Phe Ile Asn Asn Met Ile Ser Phe Lys Lys Pro Ile Gly
        275                 280                 285

Ser Val Thr Ile Ser Gly His Lys Phe Leu Gly Cys Pro Met Pro Cys
    290                 295                 300

Gly Val Gln Ile Thr Arg Lys Ser Tyr Ile Asn Asn Leu Ser Thr Asn
305                 310                 315                 320

Val Glu Tyr Ile Ala Ser Val Asp Ala Thr Ile Ser Gly Ser Arg Asn
                325                 330                 335

Gly Leu Thr Pro Ile Phe Leu Trp Tyr Ser Leu Ser Ala Lys Gly Gln
            340                 345                 350

Val Gly Leu Gln Lys Asp Val Lys Arg Cys Leu Asp Asn Ala Lys Tyr
        355                 360                 365

Leu Lys Asp Arg Leu Gln Lys Ala Gly Ile Ser Val Met Leu Asn Glu
    370                 375                 380
```

```
Leu Ser Ile Ile Val Leu Glu Arg Pro Arg Asp His Glu Phe Val
385                 390                 395                 400

Arg Arg Trp Gln Leu Ser Cys Val Lys Asp Met Ala His Val Ile Val
            405                 410                 415

Met Pro Gly Ile Thr Arg Glu Met Leu Asp Asn Phe Thr Ser Glu Leu
            420                 425                 430

Val Gln Gln Arg Lys Val Trp Tyr Gln Asn Gly Gln Thr Asn Pro Pro
            435                 440                 445

Cys Val Gly Glu Asp Ile Gly Ala Gln Asn Cys Ala Cys Ser Tyr His
            450                 455                 460

Lys Ile Asp Tyr Ile Cys Pro
465                 470
```

<210> SEQ ID NO 10
<211> LENGTH: 993
<212> TYPE: DNA
<213> ORGANISM: Lycopersicon esculentum

<400> SEQUENCE: 10

```
atgagtagtg tggcagcgac aaaaacagta tgtgtaacag gagcatcagg atacatagca      60
tcatggcttg tcaatttctt gcttcaacgt ggttacactg ttaaagcctc cgttcgtgac     120
cccaatgatc ccaagaaaac acagcatttg atctcgttag gtggggccaa ggagaggctt     180
cacttgttca agcaaacctt ttagaagag gttcctttg atgctgtggt tgatggatgt       240
gaaggtgtat tccatacagc atcacctttt tactactctg ttacagaccc acaggctgaa     300
ttacttgatc agctgttaa ggggacactc aatcttctcg gttcatgtgc caaagcacca     360
tcagtaaaac gtgtggtttt aacatcttcc atagctgcag ttgcttatag tggtgagcct     420
cggacacctg aggttgtggt tgatgagagt tggtggacta gtccagacta ctgcagagaa     480
aagcagctct ggtatgttct ctcaaagaca ttagctgagg atgctgcctg gaagtttgtg     540
aaggagaaag gcattgatat ggttgcaata aatcctgcta tggttattgg tccttttgtta   600
cagcctaccc ttaataccag ttctgctgca gtcttgaact tggtaaatgg tgccgagaca     660
tacccaaatg ctacctttgg gtgggttaat gtcaaagatg ttgcaaatgc acatattctt     720
gcatttgaga cccttcagc taatgggaga tatttgatgg ttgagagagt tgcacactat     780
tctgatatac tgaagatatt acgtgaactt atcctacaa tgcgacttcc agaaaagtgt     840
gctgatgaca tccattgat gcaaaactat caagtatcaa agaaagggc aaaaagcttg      900
ggcgttgaat ttactcccct tgaagaaagc atcaaagaaa ctgttgaaag cttgaaggaa     960
aagaagtttt ttggaggctc atctgctatg tga                                 993
```

<210> SEQ ID NO 11
<211> LENGTH: 330
<212> TYPE: PRT
<213> ORGANISM: Lycopersicon esculentum

<400> SEQUENCE: 11

```
Met Ser Ser Val Ala Ala Thr Lys Thr Val Cys Val Thr Gly Ala Ser
1               5                   10                  15

Gly Tyr Ile Ala Ser Trp Leu Val Asn Phe Leu Leu Gln Arg Gly Tyr
            20                  25                  30

Thr Val Lys Ala Ser Val Arg Asp Pro Asn Asp Pro Lys Lys Thr Gln
            35                  40                  45

His Leu Ile Ser Leu Gly Gly Ala Lys Glu Arg Leu His Leu Phe Lys
        50                  55                  60
```

```
Ala Asn Leu Leu Glu Glu Gly Ser Phe Asp Ala Val Val Asp Gly Cys
 65                  70                  75                  80

Glu Gly Val Phe His Thr Ala Ser Pro Phe Tyr Ser Val Thr Asp
             85                  90                  95

Pro Gln Ala Glu Leu Leu Asp Pro Ala Val Lys Gly Thr Leu Asn Leu
            100                 105                 110

Leu Gly Ser Cys Ala Lys Ala Pro Ser Val Lys Arg Val Leu Thr
            115                 120                 125

Ser Ser Ile Ala Ala Val Ala Tyr Ser Gly Glu Pro Arg Thr Pro Glu
130                 135                 140

Val Val Val Asp Glu Ser Trp Trp Thr Ser Pro Asp Tyr Cys Arg Glu
145                 150                 155                 160

Lys Gln Leu Trp Tyr Val Leu Ser Lys Thr Leu Ala Glu Asp Ala Ala
                165                 170                 175

Trp Lys Phe Val Lys Glu Lys Gly Ile Asp Met Val Ala Ile Asn Pro
                180                 185                 190

Ala Met Val Ile Gly Pro Leu Leu Gln Pro Thr Leu Asn Thr Ser Ser
            195                 200                 205

Ala Ala Val Leu Asn Leu Val Asn Gly Ala Glu Thr Tyr Pro Asn Ala
210                 215                 220

Thr Phe Gly Trp Val Asn Val Lys Asp Val Ala Asn Ala His Ile Leu
225                 230                 235                 240

Ala Phe Glu Asn Pro Ser Ala Asn Gly Arg Tyr Leu Met Val Glu Arg
                245                 250                 255

Val Ala His Tyr Ser Asp Ile Leu Lys Ile Leu Arg Glu Leu Tyr Pro
            260                 265                 270

Thr Met Arg Leu Pro Glu Lys Cys Ala Asp Asp Asn Pro Leu Met Gln
275                 280                 285

Asn Tyr Gln Val Ser Lys Glu Arg Ala Lys Ser Leu Gly Val Glu Phe
            290                 295                 300

Thr Pro Leu Glu Glu Ser Ile Lys Glu Thr Val Glu Ser Leu Lys Glu
305                 310                 315                 320

Lys Lys Phe Phe Gly Gly Ser Ser Ala Met
                325                 330

<210> SEQ ID NO 12
<211> LENGTH: 1416
<212> TYPE: DNA
<213> ORGANISM: Lycopersicon esculentum

<400> SEQUENCE: 12
atgggtagcc tcacacttga atggattttt gagccatcac ctatgacacc cagaagttta      60
gcagcgatga cacccaaaag tttagcacga cgaagattgt ttccaaatgt ggacaacaaa     120
aaacagaagg tggaacaatc aggcgcaggg ccaaggaaaa acttacaact tgaagtcatg     180
gaaccttctt tgaacaataa tggtccttct ttggacacta tcttggtcaa ttatttggac     240
acacttactc aacgagtcaa ttatcattta ggttatccag tcaacatatg ttatgatcac     300
tatgcatctt tagcaccact tttgcagttt cacctaaaca attgtggtga tccttttccta    360 caaaacactg tcgatttcca ttcaaaagac tttgaagtgg ctgttttgga ttggtttgca     420
aaactatggg aaattgaaaa ggatcaatat ggggatatg ttaccaatgg tgcaccgaa       480 ggcaatctcc atggtatttt gttagggaga gagttacttc ctgaaggaat attatatgca     540 tcaaagact ctcactactc agtcttcaaa gctgcaagaa tgtatagaat ggattcagaa      600
acaatcaaca catcagtgac tggggagatg gattattcag atttaagagc aaagttactt    660
```

```
caaaataagg acaaccagc tattataaat gtcacaattg aactacgtt caaaggagca    720
atcgatgacc tggatgttat tcttgaaaca ctcaaagaat gtggctattc acaagatagg   780
ttttacatcc attgtgatgc agcactatgt ggtcttatga cccctttat aaacaatatg    840
attagtttca agaagccaat tggaagtgtc acaatttctg gtcacaagtt cttaggatgc    900
ccaatgcctt gtggtgtcca aataacaaga aaaagctaca tcaataatct ctcaacaaat    960
gtggaataca ttgcttctgt cgatgccact atttctggta gtcgtaacgg tttgactcca   1020
atttttcttat ggtatagctt aagcgcaaaa ggtcaagttg gacttcaaaa ggatgttaaa   1080
agatgtctcg acaatgccaa atatttgaaa atcgccttc aacaagcagg aataagtgtc    1140
atgttaaatg agcttagcat catagttgta cttgaaaggc ctcgtgacca tgaatttgtg   1200
cgtcgttggc aactttcatg cgtcaaagat atggcacatg ttattgttat gccaggcatc   1260
acccgagaaa tgcttgacaa tttcgtcagt gaactagttc aacaaagaaa acaatggtac   1320
cgagatggaa aagcagaggc tccttgtgtt ggggaggata ttggtgctca aaattgtgca   1380
tgctcttatc ataagattga ttatattggt ccttag                             1416
```

<210> SEQ ID NO 13
<211> LENGTH: 471
<212> TYPE: PRT
<213> ORGANISM: Lycopersicon esculentum

<400> SEQUENCE: 13

```
Met Gly Ser Leu Thr Leu Glu Met Asp Phe Glu Pro Ser Pro Met Thr
1               5                   10                  15

Pro Arg Ser Leu Ala Ala Met Thr Pro Lys Ser Leu Ala Arg Arg Arg
            20                  25                  30

Leu Phe Pro Asn Val Asp Asn Lys Gln Lys Val Glu Gln Ser Gly
        35                  40                  45

Ala Gly Pro Arg Lys Asn Leu Gln Leu Glu Val Met Glu Pro Ser Leu
    50                  55                  60

Asn Asn Asn Gly Pro Ser Leu Asp Thr Ile Leu Val Asn Tyr Leu Asp
65                  70                  75                  80

Thr Leu Thr Gln Arg Val Asn Tyr His Leu Gly Tyr Pro Val Asn Ile
                85                  90                  95

Cys Tyr Asp His Tyr Ala Ser Leu Ala Pro Leu Leu Gln Phe His Leu
            100                 105                 110

Asn Asn Cys Gly Asp Pro Phe Leu Gln Asn Thr Val Asp Phe His Ser
        115                 120                 125

Lys Asp Phe Glu Val Ala Val Leu Asp Trp Phe Ala Lys Leu Trp Glu
    130                 135                 140

Ile Glu Lys Asp Gln Tyr Trp Gly Tyr Val Thr Asn Gly Gly Thr Glu
145                 150                 155                 160

Gly Asn Leu His Gly Ile Leu Leu Gly Arg Glu Leu Leu Pro Glu Gly
                165                 170                 175

Ile Leu Tyr Ala Ser Lys Asp Ser His Tyr Ser Val Phe Lys Ala Ala
            180                 185                 190

Arg Met Tyr Arg Met Asp Ser Glu Thr Ile Asn Thr Ser Val Thr Gly
        195                 200                 205

Glu Met Asp Tyr Ser Asp Leu Arg Ala Lys Leu Leu Gln Asn Lys Asp
    210                 215                 220

Lys Pro Ala Ile Ile Asn Val Thr Ile Gly Thr Thr Phe Lys Gly Ala
225                 230                 235                 240
```

```
Ile Asp Asp Leu Asp Val Ile Leu Glu Thr Leu Lys Glu Cys Gly Tyr
            245             250             255

Ser Gln Asp Arg Phe Tyr Ile His Cys Asp Ala Ala Leu Cys Gly Leu
            260             265             270

Met Thr Pro Phe Ile Asn Asn Met Ile Ser Phe Lys Lys Pro Ile Gly
            275             280             285

Ser Val Thr Ile Ser Gly His Lys Phe Leu Gly Cys Pro Met Pro Cys
            290             295             300

Gly Val Gln Ile Thr Arg Lys Ser Tyr Ile Asn Asn Leu Ser Thr Asn
305             310             315             320

Val Glu Tyr Ile Ala Ser Val Asp Ala Thr Ile Ser Gly Ser Arg Asn
            325             330             335

Gly Leu Thr Pro Ile Phe Leu Trp Tyr Ser Leu Ser Ala Lys Gly Gln
            340             345             350

Val Gly Leu Gln Lys Asp Val Lys Arg Cys Leu Asp Asn Ala Lys Tyr
            355             360             365

Leu Lys Asn Arg Leu Gln Gln Ala Gly Ile Ser Val Met Leu Asn Glu
            370             375             380

Leu Ser Ile Ile Val Val Leu Glu Arg Pro Arg Asp His Glu Phe Val
385             390             395             400

Arg Arg Trp Gln Leu Ser Cys Val Lys Asp Met Ala His Val Ile Val
            405             410             415

Met Pro Gly Ile Thr Arg Glu Met Leu Asp Asn Phe Val Ser Glu Leu
            420             425             430

Val Gln Gln Arg Lys Gln Trp Tyr Arg Asp Gly Lys Ala Glu Ala Pro
            435             440             445

Cys Val Gly Glu Asp Ile Gly Ala Gln Asn Cys Ala Cys Ser Tyr His
            450             455             460

Lys Ile Asp Tyr Ile Gly Pro
465             470
```